US012797234B2

(12) United States Patent
Shah et al.

(10) Patent No.: US 12,797,234 B2
(45) Date of Patent: Nov. 17, 2026

(54) DUAL PURPOSE ORTHODONTIC APPLIANCE FOR ALIGNMENT, BRUXISM, AND SLEEP APNEA WITH SMART SENSORS AND CONTROL MODULE SYSTEM

(71) Applicant: Real 3D Polymers, LLC, Troy, MI (US)

(72) Inventors: Sureshkumar Shah, Troy, MI (US); Dinesh Shah, Troy, MI (US); Prasanna-Kumar Shivapuja, Roseville, MI (US); Shail Chokhavatia, Paramus, NJ (US); Bruce Bennett, II, Auburn Hills, MI (US)

(73) Assignee: Real 3D Polymers, LLC, Troy, MI (US)

(*) Notice: Subject to any disclaimer, the term of this patent is extended or adjusted under 35 U.S.C. 154(b) by 168 days.

(21) Appl. No.: 17/977,717

(22) Filed: Oct. 31, 2022

(65) Prior Publication Data

US 2023/0181350 A1 Jun. 15, 2023

Related U.S. Application Data

(63) Continuation-in-part of application No. 16/248,430, filed on Jan. 15, 2019, now Pat. No. 11,484,390, (Continued)

(51) Int. Cl.
*A61F 5/56* (2006.01)
*A61B 5/00* (2006.01)
(Continued)

(52) U.S. Cl.
CPC ............ *A61F 5/566* (2013.01); *A61B 5/4836* (2013.01); *A61B 5/682* (2013.01); *A61C 7/08* (2013.01);
(Continued)

(58) Field of Classification Search
CPC ......... A61F 5/66; A61B 5/4836; A61B 5/682; A61C 7/08; A61C 7/36
See application file for complete search history.

(56) References Cited

U.S. PATENT DOCUMENTS 6,542,774 B2 * 4/2003 Hill ...................... A61N 1/3962 607/9
7,954,494 B1 * 6/2011 Connor .................. A61F 5/566 128/848
(Continued)

OTHER PUBLICATIONS

Erin Hunter, "Electrical Stimulation May Improve Sleep Apnea, Daytime Sleepiness Better Than CPAP", Pharmacy Times, Aug. 7, 2023.
(Continued)

*Primary Examiner* — Nicholas D Lucchesi
(74) *Attorney, Agent, or Firm* — MaxGoLaw PLLC

(57) ABSTRACT

A dual-purpose Oral Appliances having smart sensors and control module for treating sleep apnea and simultaneously straightening the teeth or reducing the bruxism or reducing the TMJ disorder are disclosed. The appliance contains upper and or lower teeth trays with or without air passageway. The appliance can be with or without external housing. The episodes of sleep apnea are reducing by one or combination of several mechanisms such as mandibular advancement (MAD), air stimulation by control of inhaled air flow bypassing the tongue and or micro-holes in air passageways, neuro/muscle electric stimulation of tongue and sleep position training. The sensors located inside or outside of the mouth, measure physiological and or biological and or chemical aspects of the patients. The sensors are connected to control module system consists of battery, microprocessor, and data transmission technologies.

8 Claims, 63 Drawing Sheets

Related U.S. Application Data which is a continuation-in-part of application No. 15/062,043, filed on Mar. 4, 2016, now Pat. No. 10,179,035.

(60) Provisional application No. 62/128,450, filed on Mar. 4, 2015.

(51) Int. Cl.

| | |
|---|---|
| ***A61C 7/08*** | (2006.01) |
| ***A61C 7/36*** | (2006.01) |
| ***A61M 16/00*** | (2006.01) |
| ***A61N 1/36*** | (2006.01) |

(52) U.S. Cl.

CPC ........... *A61C 7/36* (2013.01); *A61M 16/0066* (2013.01); *A61N 1/3601* (2013.01); *A61F 2005/563* (2013.01)

(56) References Cited

U.S. PATENT DOCUMENTS

| | | | | |
|---|---|---|---|---|
| 2015/0190630 | A1* | 7/2015 | Kent | A61N 1/3601 128/848 |
| 2016/0199215 | A1* | 7/2016 | Kopelman | A61F 5/566 128/848 |
| 2016/0199216 | A1* | 7/2016 | Cam | A61F 5/566 128/848 |
| 2016/0367188 | A1* | 12/2016 | Malik | G16H 40/67 |
| 2017/0312117 | A1* | 11/2017 | Shah | A61B 5/01 |
| 2017/0347956 | A1* | 12/2017 | Zegarelli | A61B 5/01 |
| 2018/0000563 | A1* | 1/2018 | Shanjani | A61C 7/002 |
| 2018/0078344 | A1* | 3/2018 | Falkel | A61C 7/36 |
| 2019/0380863 | A1* | 12/2019 | Mauclaire | A61F 5/566 |
| 2022/0167876 | A1* | 6/2022 | Kaltenbach | A61B 5/1114 |
| 2022/0331065 | A1* | 10/2022 | Shah | A61B 5/02055 |

OTHER PUBLICATIONS

Ratneswaran, et al., "Domiciliary transcutaneous electrical stimulation in patients with obstructive sleep apnoea and limited adherence to continuous positive airway pressure therapy: a single-centre, open-label, randomised, controlled phase III trial," www.the lancet.com, vol. 62, Aug. 2023, pp. 1-11.

* cited by examiner

DUAL PURPOSE ORTHODONTIC APPLIANCE FOR ALIGNMENT, BRUXISM, AND SLEEP APNEA WITH SMART SENSORS AND CONTROL MODULE SYSTEM

RELATED APPLICATIONS

This continuation-in-part (CIP) patent application claims the benefit of priority to U.S. patent application Ser. No. 16/248,430 to Shivapuja et al., filed Jan. 15, 2019 and now U.S. Pat. No. 11,484,390, which in turn claims priority to U.S. patent application Ser. No. 15/062,043 to Shivapuja et al., filed Mar. 4, 2016, now U.S. Pat. No. 10,179,035, which in turn claims priority to U.S. Provisional Patent Application No. 62/128,450 to Shivapuja et al., filed Mar. 4, 2015, all of these incorporated by reference herein in their entireties.

TECHNOLOGY FIELD

The present invention is in the field of dual-purpose orthodontic appliances for simultaneously treating sleep apnea and straightening the teeth (desired movement of teeth) or reducing bruxism (teeth grinding) or reducing TMJ using smart sensors and smart sensors connected to a microprocessor/control module system having the capability of wireless communication. Teeth trays are defined as "aligners" or "bite splint" or "night guard" or "mouthguard". The appliance has one or several sensors mounted at specific locations inside the mouth on teeth trays and or externally on detachable housing which is connected to teeth trays. There are different types of sensors such as physical sensors, chemical sensors, biosensors, positional sensors, accelerometers, gyroscope, pressure sensors, touch sensors, pulse oximeter, temperature sensors are attached at difference location of the appliance depending on the function(s) desired to treat sleep apnea and for aligning the teeth or reducing the bruxism or teeth grinding. The smart sensors are mounted on control module or and are connected to control module system. The present invention is also in the field of a computer aided design procedure for preparing a customized teeth trays designs, software, and control module with microprocessor having flash drive and manufacturing technologies of orthodontic appliances. The appliance is manufactured by 3D printings (additive manufacturing) technologies or other plastics manufacturing technologies.

The subject matter is directed to orthodontia, and specifically to 3D printing technologies applied to direct manufacture of orthodontic aligners for straightening teeth with innovative anchors to be placed on the teeth in conjunction with the aligners. The subject matter is also directed to aligner designs, materials, 3D support structures and finishes to be used in additive manufacturing processes for making the orthodontic aligners and anchors. The subject matter is also directed to additive manufacturing processes for making complex and very thin aligner designs. Modified aligners for correcting bite or as a splint to treat temporomandibular disorder (TMD) or to treat sleep apnea with or without mandibular advancement or as a functional appliance to promote growth of the lower jaw are also described.

BACKGROUND

Currently, there are two main systems in the market for correcting the position of teeth. The first system is a braces scenario that may include traditional self-ligating orthodontic brackets with a steel tight bracket, a straight wire application, or a traditional Tweed appliance. The second system is a clear aligner system, in which aligners are interchangeable by the patient during treatment. The clinician may prescribe a series of aligners, which are generally placed over, but are not themselves adhesively secured or otherwise attached to, the patient's teeth, to move one or more teeth from their original position to their aesthetically pleasing or functionally corrected position. Typically, a series of aligners is required to fully treat the patient because the degree of movement produced by a given single aligner is limited. One such aligner system is the INVISALIGN aligner system (Align Technology, Inc., San Jose, CA). Each aligner is responsible for moving the teeth toward their final pre-determined or aesthetically/functionally correct position.

The INVISALIGN aligners are fabricated by physical and computer-aided molding processes. The conventional process begins by taking an impression of the patent's dentition, or using intra-oral scanner for teeth impression, followed by creating a denture model of the teeth on computer. This CAD file, for example an .STL file, is used to 3D-print the physical teeth models and molds. Finally, clear plastic which will form the aligner, such as a polyurethane, is molded (e.g., thermoformed) over the physical teeth model or mold of the tooth configuration to be implemented. Subsequent physical steps of the conventional process trim the molded aligner to remove sharp edges or portions which might contact and irritate the gingiva. In addition, the aligner surface and edges are typically smoothed via a process such as tumbling.

This conventional fabrication of aligners is a tedious process, which compounds both cost and time of treatment for the patient. Since such an orthodontic treatment may require, for example, 25 intermediate reset molds to represent 25 stages of treatment progress, the cost and time required for the necessary steps of mold making, aligner formation, and trimming, may be prohibitively high. The cost is additive, as each new stage in treatment or each change in treatment requires the production of a new mold. Likewise, the cost of storing a series of molds for each patient throughout treatment may be formidable. U.S. Pat. No. 5,975,893 to Align Technologies, Inc., is incorporated by reference herein in its entirety, to describe the processes elaborated above, as background information.

Treatment of malocclusion by aligners faces challenges other than the difficulty of manufacture. Specifically, aligners fastened with attachments may prove very difficult to install, as a result of the limited number of shapes that the attachment apertures on the aligner may take, consistent with the INVISALIGN manufacturing process. Specifically, the attachment apertures are formed by thermoforming over a stereolithographically-generated positive tooth model, which limits the type of apertures that may be made. Moreover, aligners may bind with the attachments and prove very difficult to remove. Furthermore, in many aligner patients, the presence of the aligner within the patient's mouth causes a change in the points of occlusion between the mandible and maxilla, and in particular, causes the guidance of occlusion to move to the rear molars. This opens the patient's bite and typically intrudes the rear molars as a consequence of the unbalanced occlusion force on the rear molars.

One result of this conventional unbalanced occlusion force can be TMJ injury after the removal of the aligner, because the force of the mandible is no longer resisted by the rear molars in the absence of the aligners. For many patients aligners fabricated manually or by thermoforming on a positive model are uncomfortable and can irritate the patient's gingiva and/or tongue to such an extent that the soft tissue becomes inflamed and can potentially bleed. This discomfort is generally caused because the aligner is trimmed inaccurately to the patient's gingival margin. The inaccuracy in trimming is generally caused by the minimum size of the trimming tool particularly on the anterior lingual side where the aligner interferes with the tongue. Other anatomy such as the incisive papilla, if not generally considered when trimming the aligner, can cause swelling or inflammation. In addition, the location where the aligner is trimmed can cause a sharp flange to be created at the base of the aligner near the gingival margin, particularly on the lingual side.

Due to disadvantages of thermoforming and to reduce the steps involved in conventional aligner manufacturing methods, as well as aligner design limitation of thermoforming process, an alternative method is needed to manufacture an aligner to configure better to the counters of the teeth and to provide better finishing of the appliance. This would reduce the inaccuracy of each step to provide better adaptation, better fit, and better finish.

An ideal alternative apparatus and methodology for realizing aligners configured to correspond to a series tooth configuration should be economical, reusable, reduce time consumption, reduce material waste, and in particular, should reduce the need for fabricating multiple casts of teeth arrangements for various stages in the orthodontic treatment.

Obstructive sleep apnea (OSA) is a sleep disorder with partial or complete cessation of breathing during one's sleep. This sleep disorder is currently treated by methods such as a surgery, oral appliance therapy, negative pressure to pull soft palate and tongue forward, implantable devices that keep the airway open during sleep by stimulating the hypoglossal nerve, strips for the nose for expiratory positive airway pressure, Positive Air Pressure (PAP) therapy, or a combination involving several methods. PAP therapies are also employed to treat other medical and respiratory disorders, such as Cheynes-Stokes respiration, congestive heart failure, and stroke. A common PAP device comprises a flow generator (e.g., a blower) that delivers gas via delivery conduit (hollow tube) to an individual interface. It is also known to deliver the PAP as a continuous positive airway pressure (CPAP), a variable airway pressure, such as bi-level pressure (Bi-PAP) that varies with the individual's respiratory cycle or an auto-titrating pressure (APAP) that varies with the monitored condition of the individual. Nasal, oral-nasal, and full-face masks are common interfaces utilized for delivering PAP to the individual's airway.

These masks can be uncomfortable due to improper fit, tight straps to hold mask in place, skin irritation at points of contact, dryness of throat, the feelings of claustrophobia, and excessive PAP pressure are major factors in individual therapy non-compliance. Also, the PAP machines can be noisy. Studies show individual compliance for PAP therapy is less than 50%. For patients who cannot tolerate CPAP machine therapy, oral appliance therapy is an effective treatment option for snoring and obstructive sleep apnea (OSA). A custom-fit oral sleep appliance known as a mandibular advancement device (MAD), can be effective for people who cannot tolerate CPAP devices. Worn only during sleep, an MAD oral appliance fits like a sports mouth guard or an orthodontic retainer. It supports the jaw in a forward position to help maintain an open upper airway. The devices snap over the upper and lower dental arches and have several designs/concepts for the lower jaw to be eased forward. Some, devices allow patient to control the degree of advancement. But there is no device on the market for children as well as adults to treat sleep apnea while they are going through the process of straightening teeth with aligners, except the combination of conventional aligners with conventional PAP devices, which is not a comfortable combination. Most importantly, treating both conditions is an advantage in preparation for definitive treatment with orthognathic surgery Gaw surgery).

DETAILED DESCRIPTION

Overview

Figure 1:
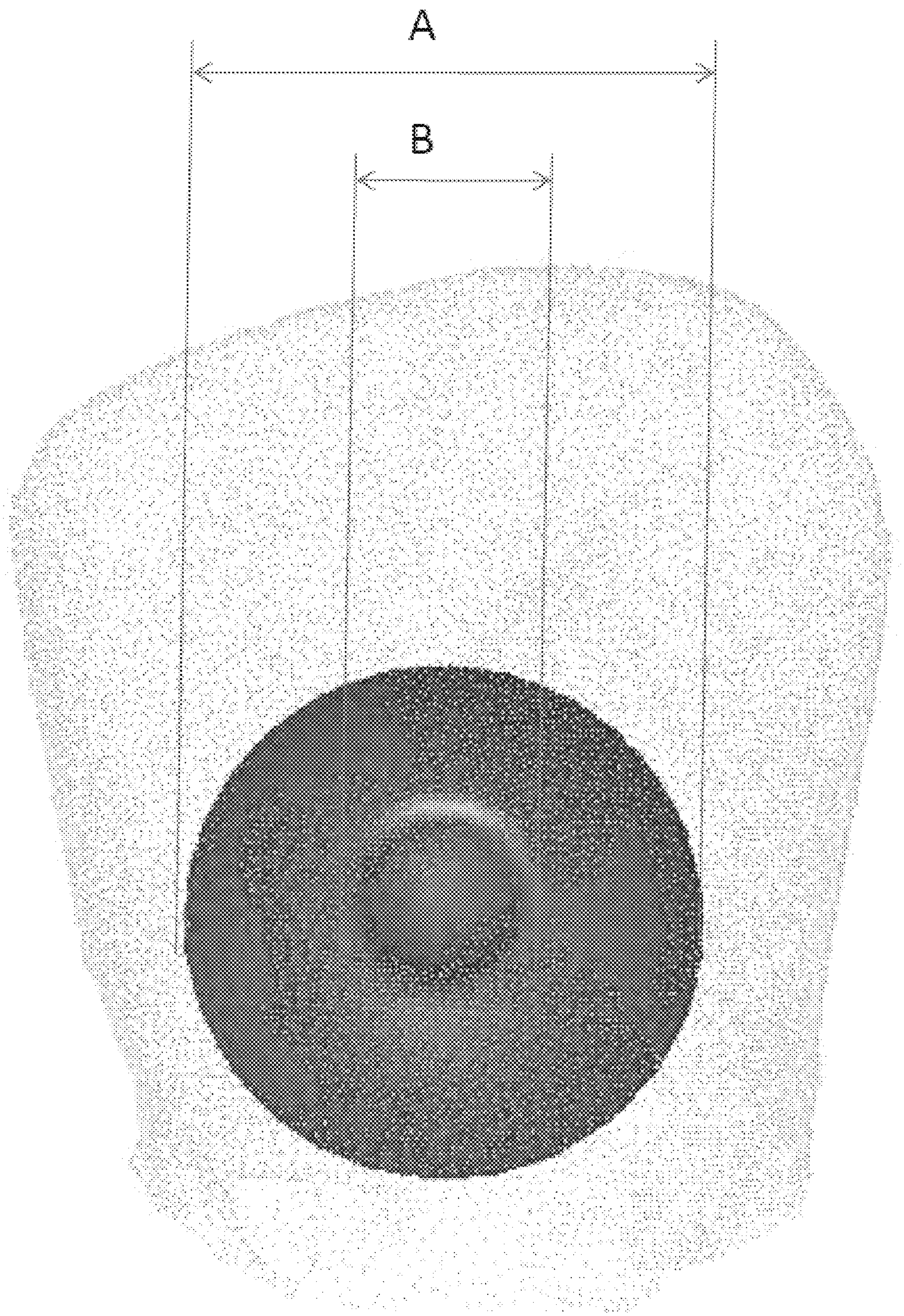
FIG. 1 is a diagram of an example divot anchor and a top view as mounted on teeth.

This disclosure describes direct 3D-printed orthodontic aligners with example torque, rotation, and full-control anchors, including systems, methods, and materials and support structures for manufacturing 3D-printed orthodontic appliances such as aligners, and also anchors, including novel "orthodontic divot anchors" (hereinafter, "divot anchors"). An example system can use divot anchors for correcting the rotation and torque control of anterior teeth, and for three-dimensional control of teeth in general.

An example process applies direct 3D-printing or additive manufacturing to create aligners and divot anchors that apply the design and mechanics concepts described herein. Example 3D-printing processes use medical-grade and medically approved materials, for example 3D-printable materials that are elastic in nature, to exert comfortable forces when a patient wears the 3D-printed aligners. Upon exertion of force, an example aligner may extend or stretch but then returns to original position to exert constant force, assisting in the programmatic movement of teeth. An example 3D-printing process prints thin, variable-thickness, hard, and hard-soft aligners, as well as aligners that may have different properties at different places or sections on the aligner, 3D-printing, for example, in a single step using an FDM process, an SLS process, a direct pellets fused deposition process, SLA, multi-jet photo cured polymer processes, HP Multi Jet Fusion technology, continuous liquid interface production technology (CLIP), and other 3D-printing processes.

The example systems and processes described herein provide unique anchoring designs on teeth, which work in conjunction with aligners and other hardware for improved tooth movement with less discomfort, reduced time of treatment, and easy placement and removal of the 3D-printed aligners and devices.

Currently, in the case of aligners, there are two main systems in the market for correcting the position of teeth. The first system is a braces scenario that may include traditional self-ligating orthodontic brackets with a steel tight bracket, a straight wire application, or a traditional Tweed appliance. The second system is a clear aligner system, in which aligners are interchangeable by the patient during treatment. There is no directly 3D printed aligner technology available in the market except the Applicant's own technology. Also, there are no directly 3D printable bite splints or nightguards to treat bruxism available in the market except the Applicant's technology. In this description, teeth trays are also called aligners or bite retainers or nightguards.

This description describes several concepts of treating sleep apnea and having sensors with a control module only on the teeth trays and or on both teeth trays and external housings. Various embodiments provide electric stimulation of the tongue and/or air stimulation of the tongue to keep the tongue relaxed, not allowing the tongue to fall back during sleep, thereby treating sleep apnea. The description also provides position control training to reduce episodes of sleep apnea.

Example Systems

The following paragraphs describe various embodiments of the subject matter. The subject matter is not intended to be limited by specific examples, and those skilled in the art can apply the principles described in ways not specifically disclosed, while remaining within the scope of the subject matter described.

In an implementation, an example system provides new orthodontic anchors, referred to herein as "divot anchors" for correcting the rotation and torque control of anterior teeth, and also three-dimensional control of teeth in general. The example divot anchors and 3D-printed aligners work in cooperation with each other to provide better and faster orthodontic realignment of teeth.

Example systems that directly 3D-print aligners and divot anchors use medically approved, orthodontic grade materials having, for example, elasticity by nature. These can exert comfortable force when worn by the patient. Upon exertion of a force the aligner may extend or stretch but returns to its original position to exert a constant force for effecting programmed teeth movement.

FIGS. 1-5 show example designs of divot anchors, including some spatial dimensions. FIGS. 6-12 show application of novel concepts as explained in context of the principles of Andrews' straight-wire appliance approach. These can provide three-dimensional control of teeth (i.e., straitening the teeth) with a removable, directly 3D-printed, series of plastic aligners (i.e., a series of aligners printed by additive manufacturing) utilizing anchor points and example divot anchors as described. FIGS. 13-17 show dynamics of example anchor geometry and placement.

FIGS. 18-29 show example concepts and dynamics of correcting rotation of teeth. Three example concepts are shown, including applying an innovative divot anchor with spacer to reduce resistance in an opposing direction, achieving rotation to create a couple with divot anchor, spacer, and soft reline, and using a suction cup with two divot anchors diagonally opposite on the tooth. FIGS. 30-36 show innovative design concepts for torque control of anterior teeth, with proposed improvements to create engagement of the aligner at the point of application of force, by making the aligner engage into the divot anchor on the buccal side towards the gingival margin, while creating spaces on the opposite side to reduce resistance.

Figure 37:
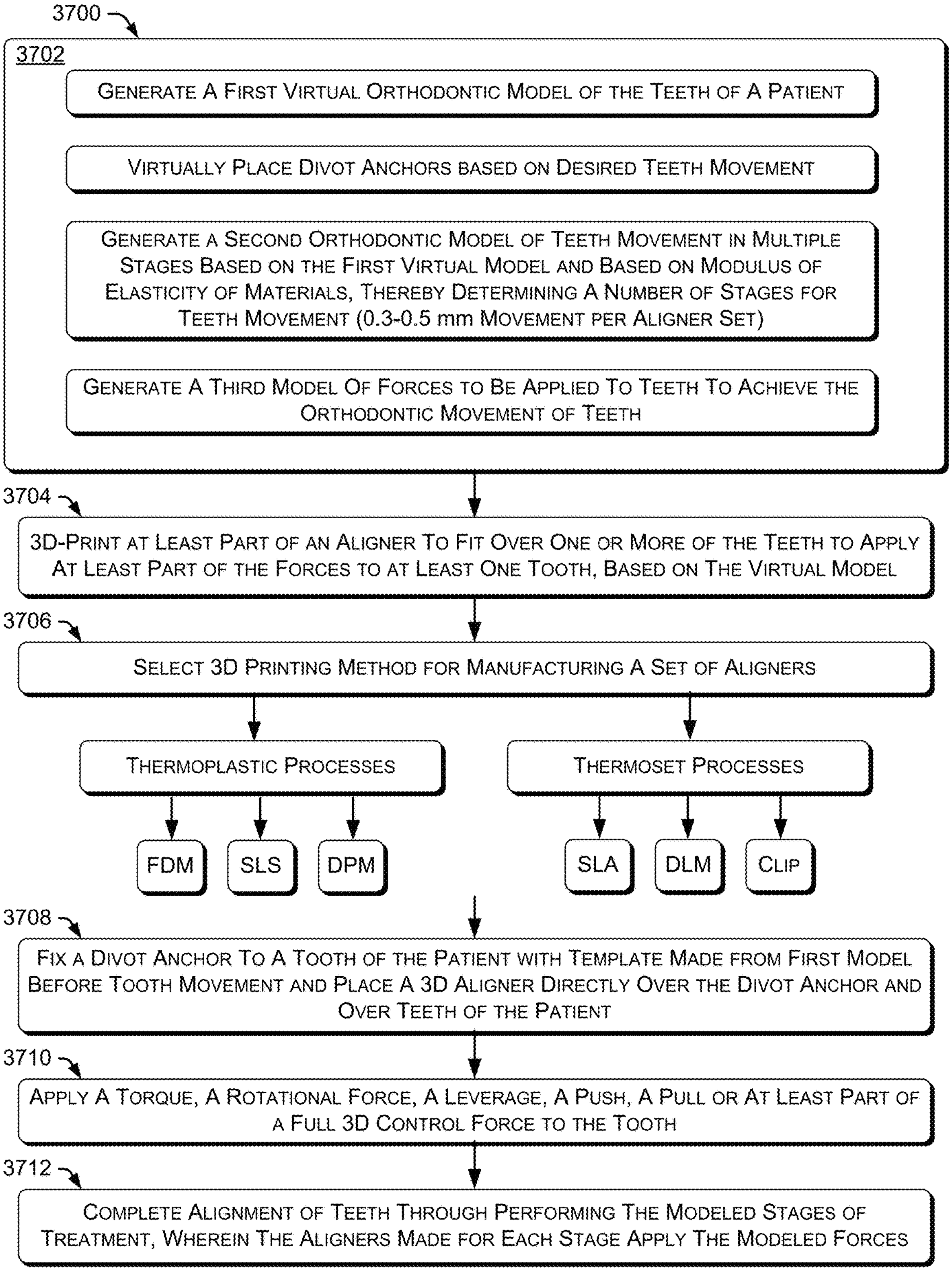
FIG. 37 is a diagram showing an example process of generating virtual models to generate 3D-printed aligners and to stage treatment using the 3D-printed aligners in combination with divot anchors.

FIG. 37 shows a flow diagram of a method of virtual modeling aligners for teeth correction, 3D printing of the aligners by several methods, and the treatment process.

FIGS. 38-41 show example designs and types of support structures for several 3D printing processes.

FIGS. 42-46 show example aligner designs for correcting bite and treating TMD.

FIGS. 48-52 show example modified designs of aligners to treat sleep apnea and snoring.

Example Divot Anchors

FIG. 1 shows an example divot anchor and top view as mounted on teeth. Dimension A is the width of the divot anchor, which is, for example, ⅔ of the width of the tooth. Dimension B is the width between two vertical peaks of elevation of the divot anchor, to be shown in next Figures.

Figure 2:
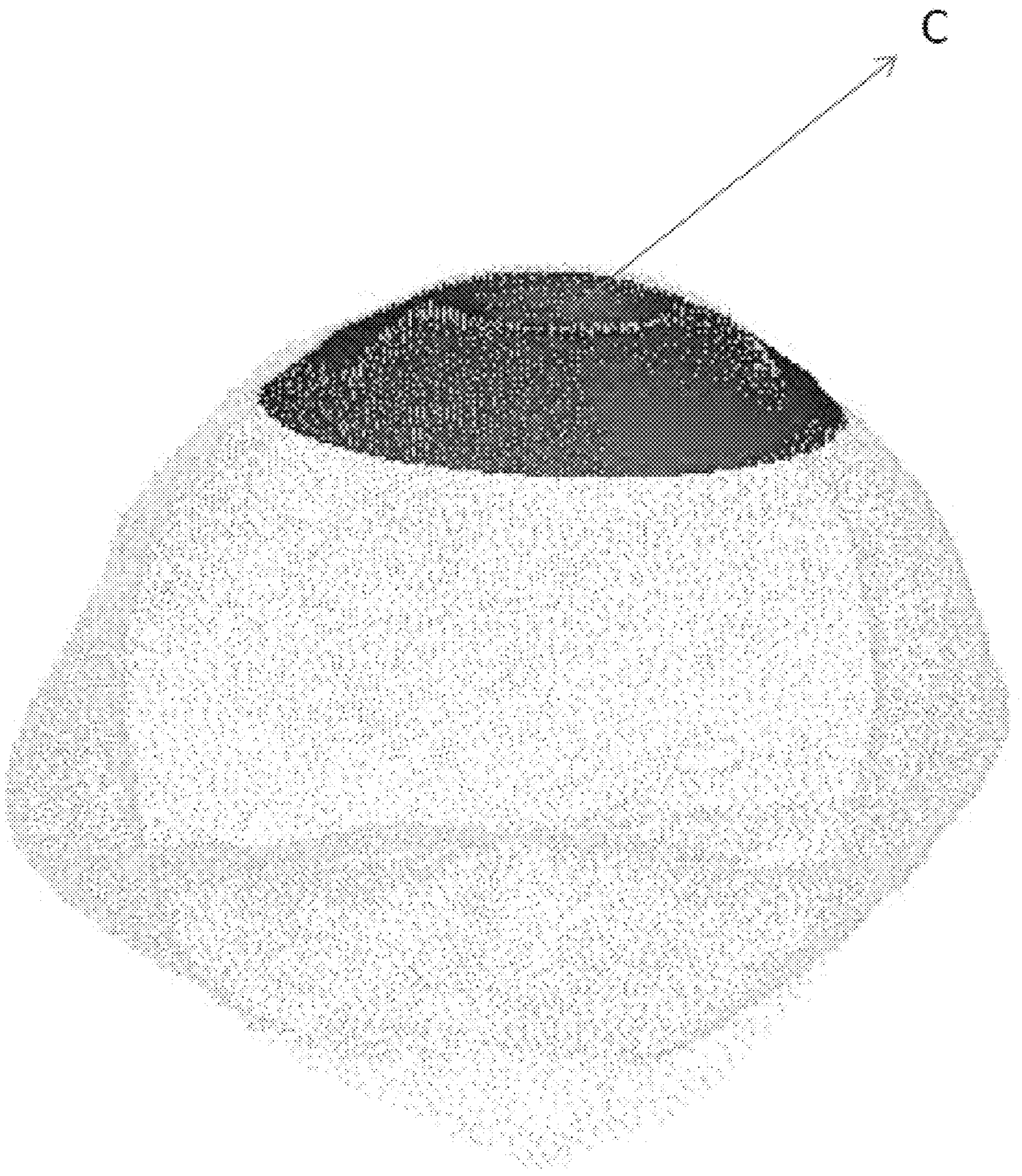
FIG. 2 is a diagram of a second view of the example divot anchor, showing an example depression in the divot anchor.

FIG. 2 shows another view of the example divot anchor, showing the divot, or depression. Dimension C is the depth of the valley, divot, or depression.

Figure 3:
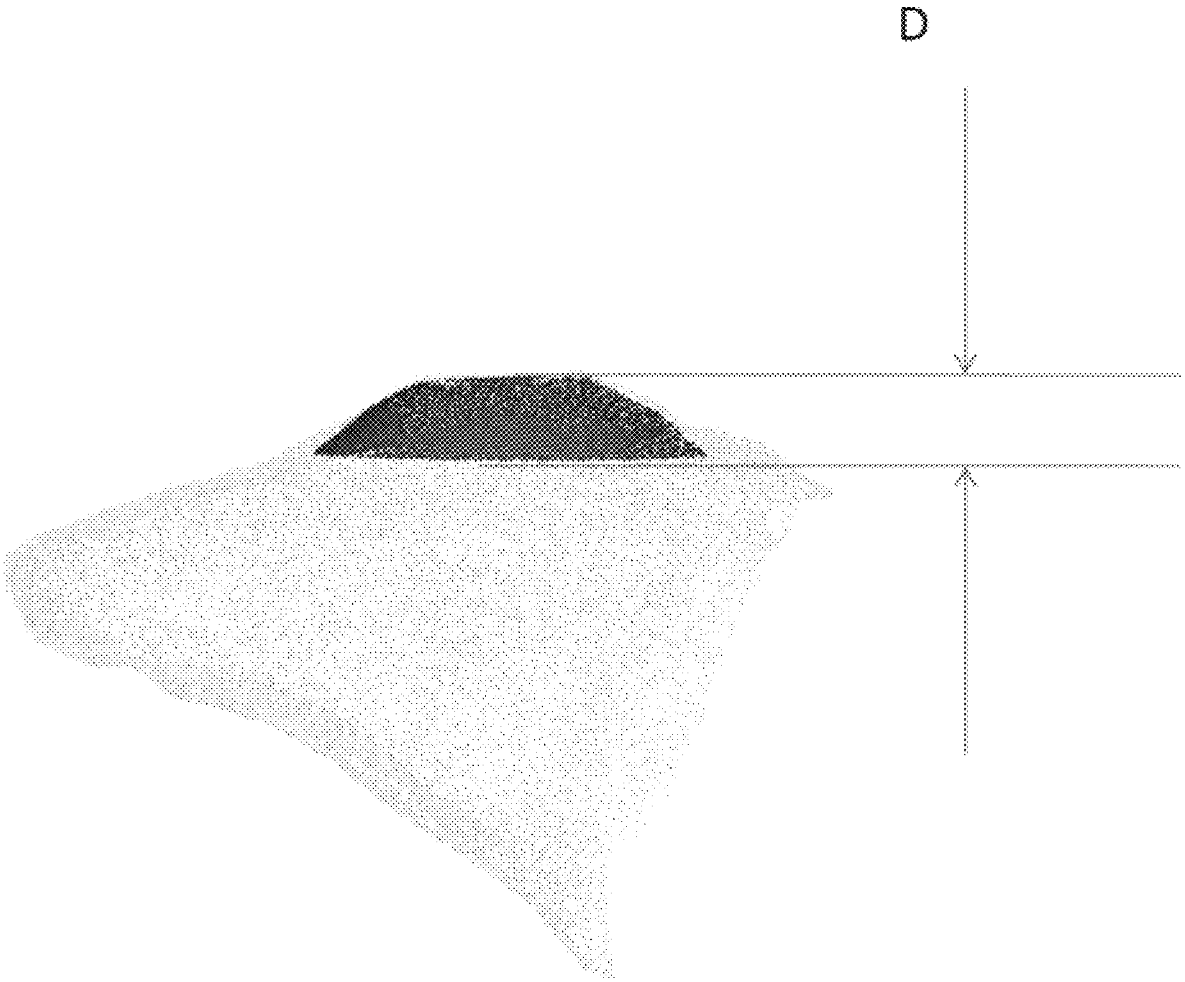
FIG. 3 is a diagram of another view of the example divot anchor, showing the height, for example.

FIG. 3 shows another view of the example divot anchor, showing dimension D, the height. An example 3D-printer aligner can fit on top of the divot anchor, and the divot, depression, or valley can be completely filled with plastic of the aligner. By contrast, it is not possible to make a conventional INVISALIGN or other thermoformed aligner fit into to such a depression or valley of the example divot anchor, as it is not possible to make a thermoformed aligner with predefined variable thicknesses (that is, predefined thick and thin sections) within the same aligner. But 3D-printing allows a manufacture of this kind, with divot anchors and matching aligners that take advantage of the divots for force leverage.

Figure 4:
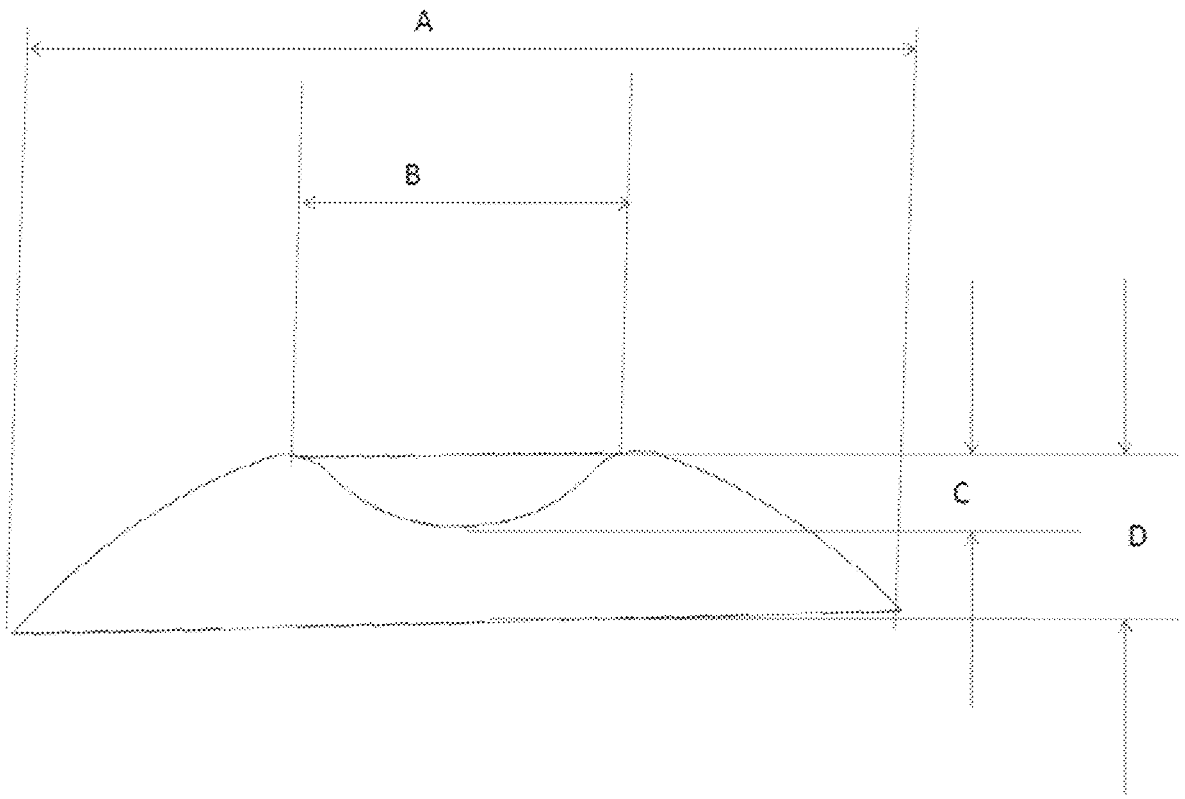
FIG. 4 is a diagram showing a two-dimensional cross section of the example divot anchor.

FIG. 4 shows a two-dimensional cross section of the example divot anchor. Dimension A is the width of the divot anchor, which in this case is ⅔ of the width of the tooth. Dimension B is the distance between the two peaks of elevation on either side of the divot, or depression. Dimension C is the depth of the divot, valley, or depression. The ratio of NB can vary from 5 to 2, while the ratio of B/C can vary from 8 to 3. The ratio of C/D can vary from 0.2 to 1.0.

Figure 5:
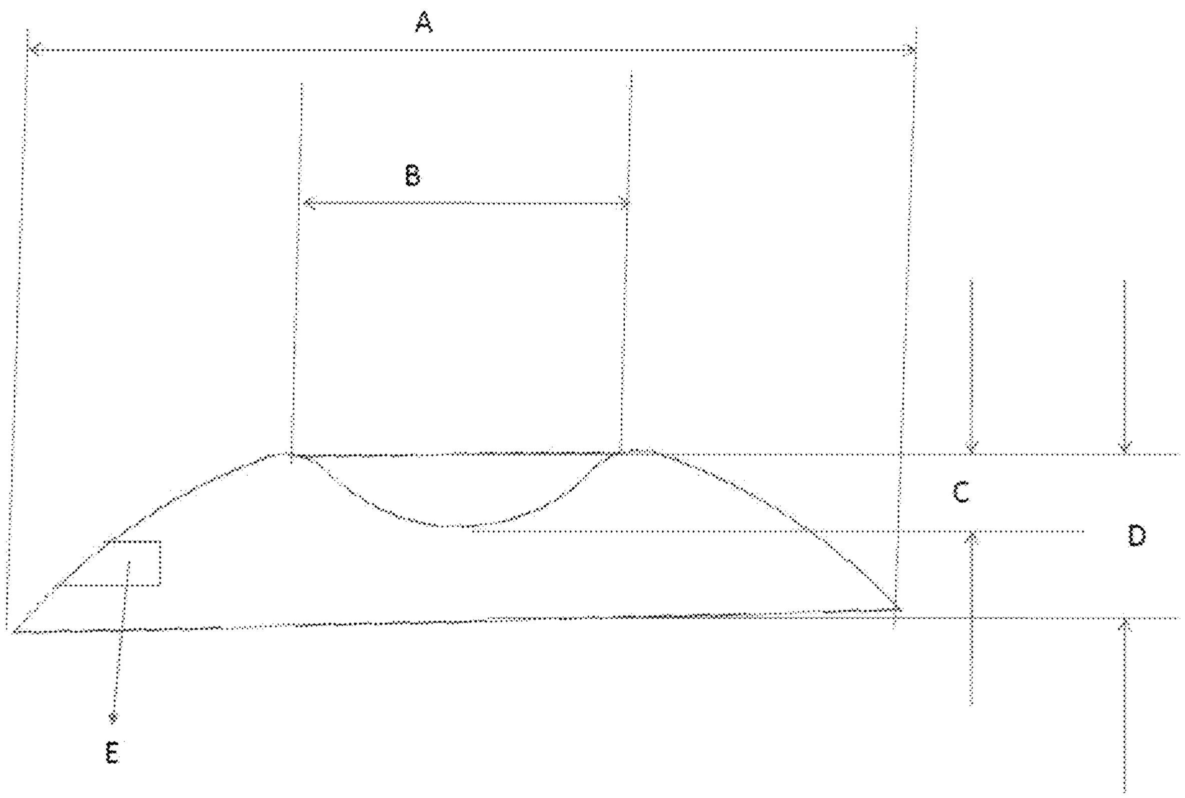
FIG. 5 is a diagram of an example divot anchor, showing a notch or channel for engaging an aligner and more anchoring design parameters for torque control and application of forces to a tooth.

FIG. 5 shows more example anchoring system designs of the divot anchor. In an implementation, the example divot anchor has a circular groove E as shown. In one embodiment, a hook design may also be incorporated into an aligner, which can be attached on the divot anchor to deliver force more effectively to where the force is needed on the teeth. Such is not feasible with current plastic aligners made by thermoforming or other conventional processes. Only 3D-printing allows the manufacture of such designs shown in FIG. 5.

Figure 6:
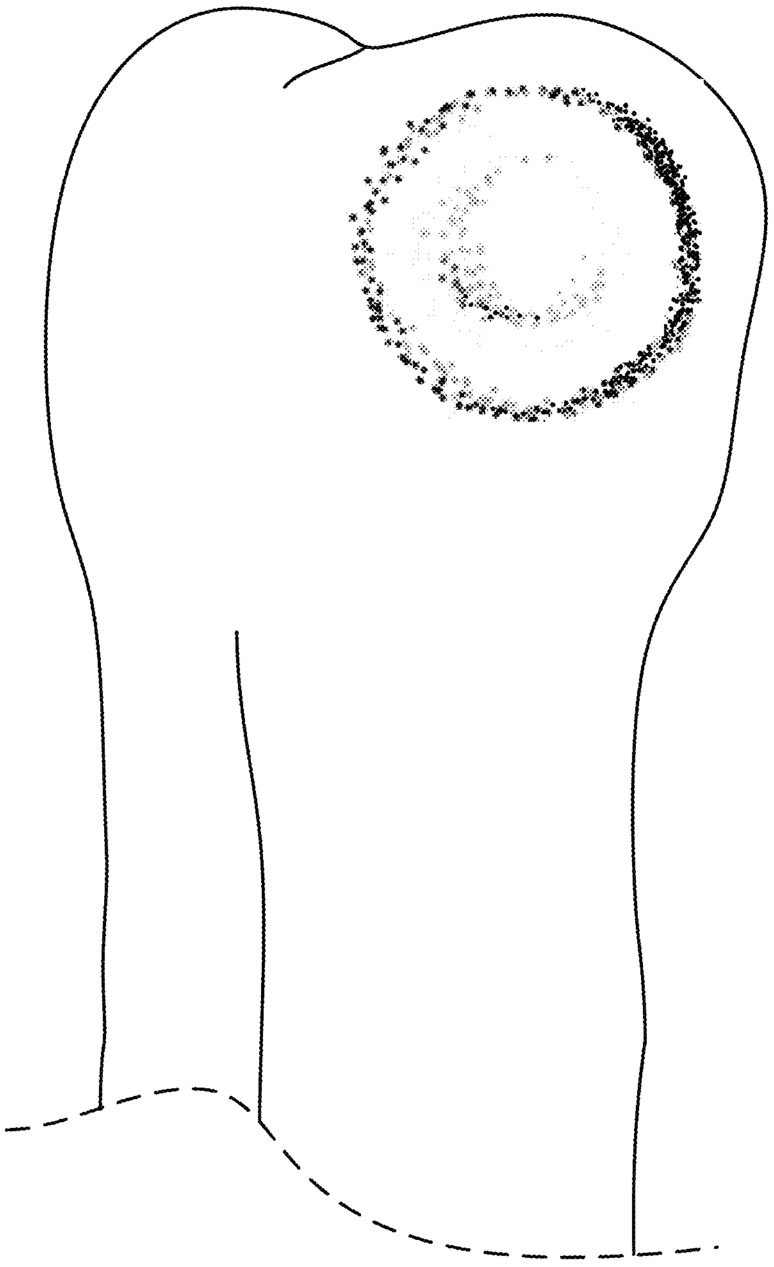
FIG. 6 is a diagram showing an example divot anchoring design mounted on single tooth for rotation control.

FIG. 6 shows an example divot anchoring design mounted on single tooth for rotation control.

Figure 7:
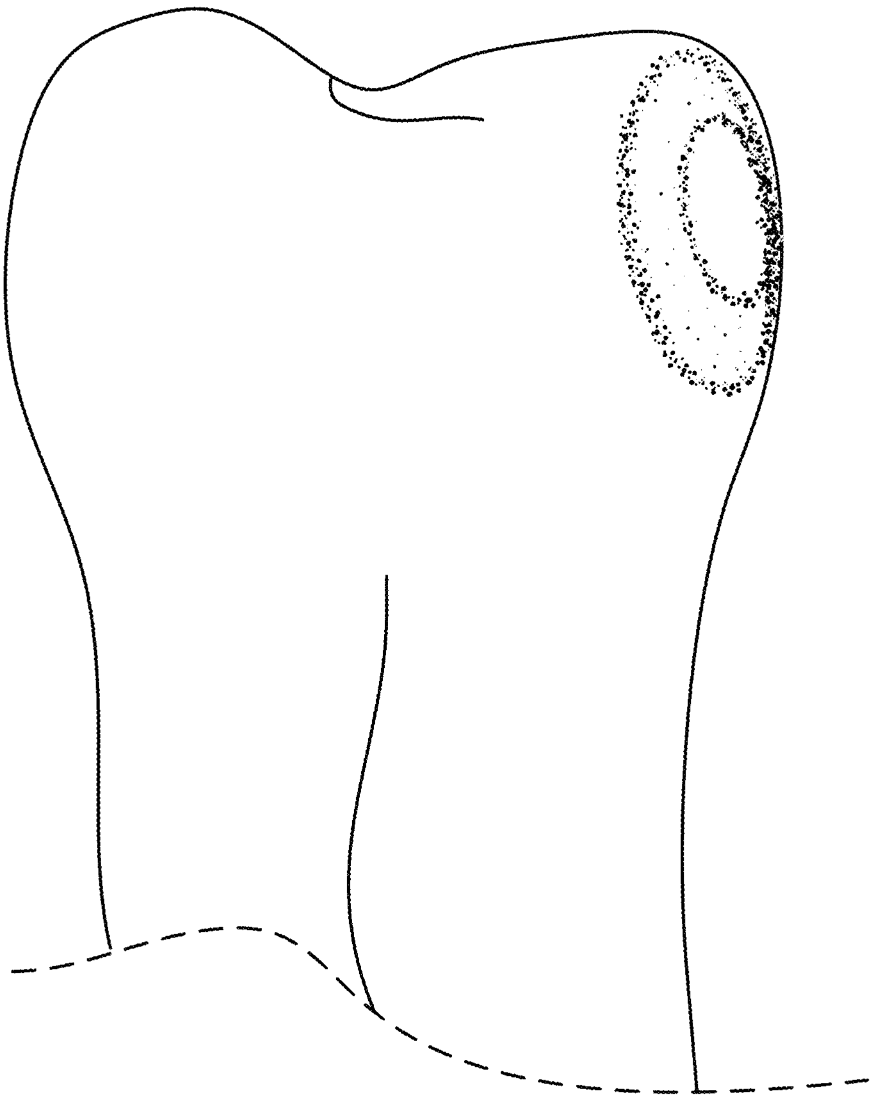
FIG. 7 is a diagram showing the example divot anchoring design of FIG. 6 from a different angle and view.

FIG. 7 shows then example divot anchoring design of FIG. 6 mounted on single tooth for rotation control, at different angle or view.

Figure 8:
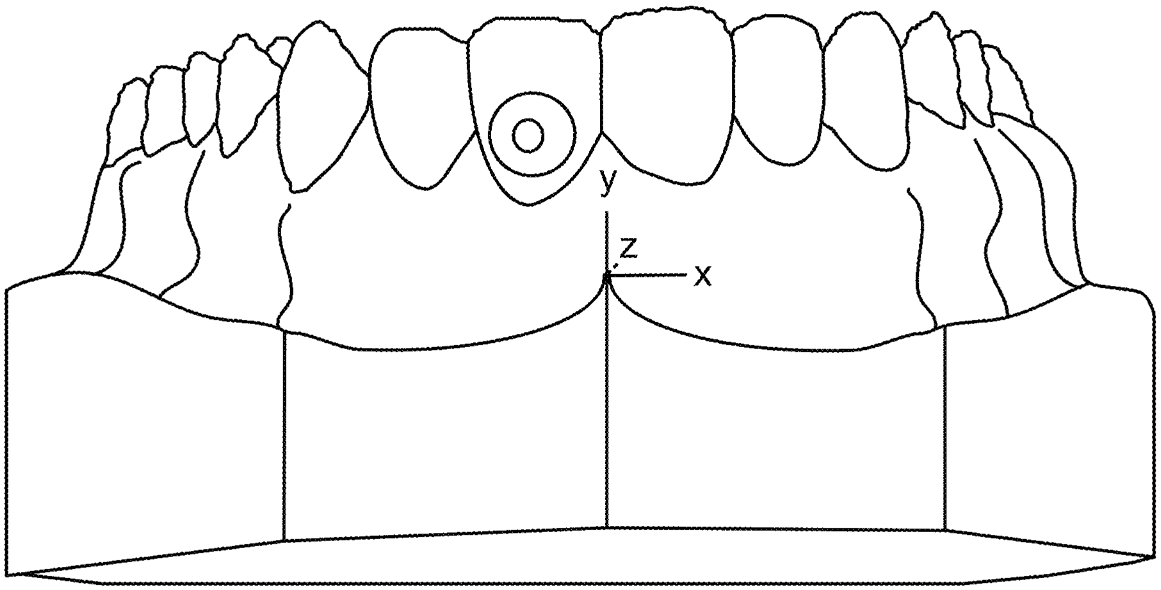
FIG. 8 is a diagram showing an example divot anchoring design mounted on single tooth for rotation control, in relation to an ideal teeth model.

FIG. 8 shows the example divot anchoring design mounted on single tooth for rotation control, shown in relation to the ideal teeth of an ideal dental model.

Figure 9:
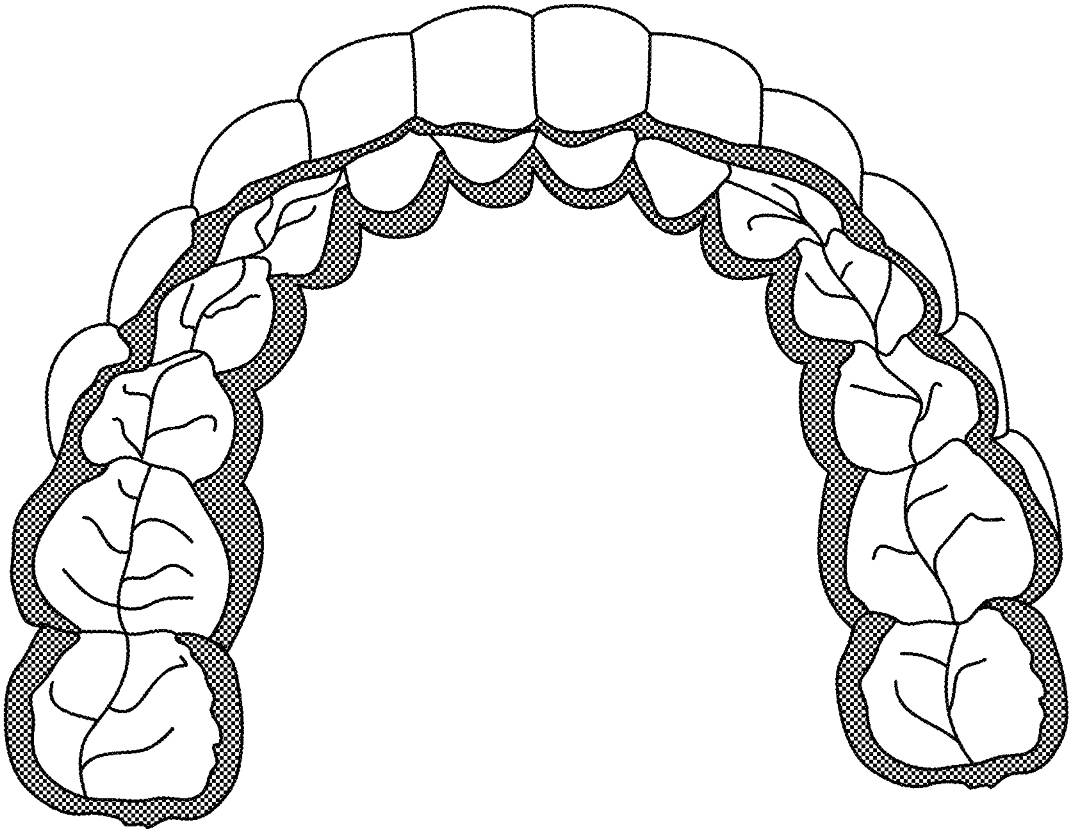
FIG. 9 is a diagram showing an example CAD file model of a 3D-printed aligner.

FIG. 9 shows a CAD design of an example 3D-printed aligner model.

Figure 10:
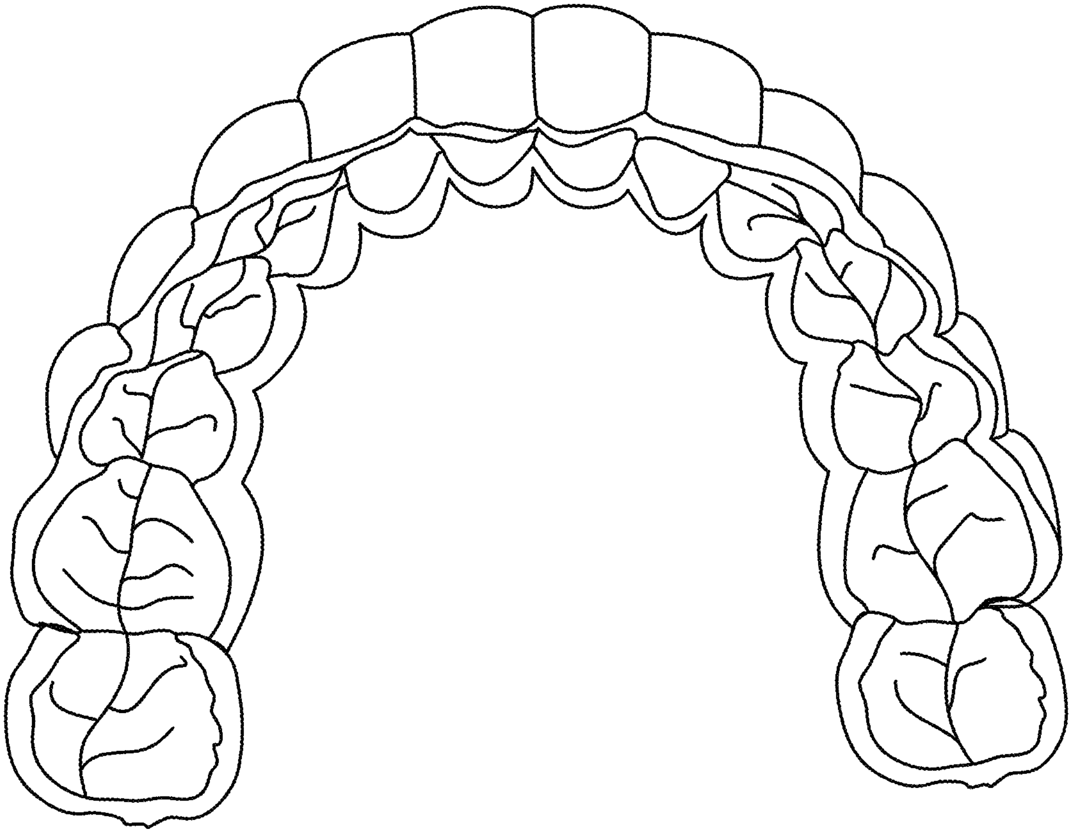
FIG. 10 is a diagram showing an example actual 3D-printed aligner, based on the generated CAD model of FIG. 9.

FIG. 10 shows an actual 3D-printed aligner manufactured from the CAD design of FIG. 9.

Figure 11:
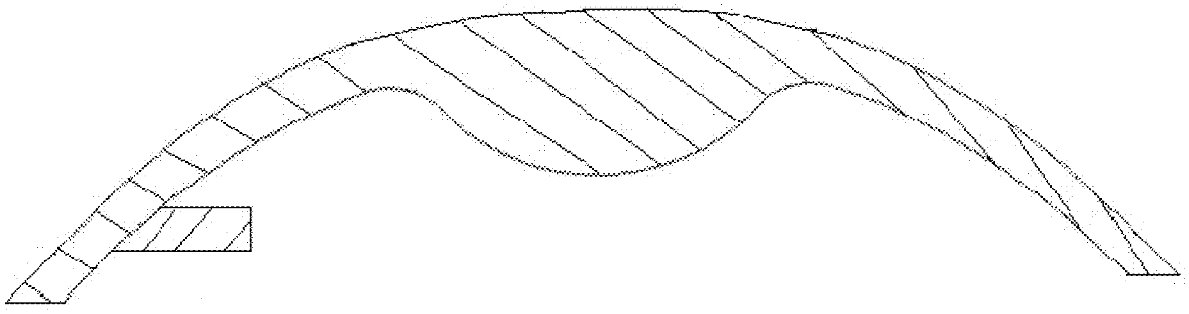
FIG. 11 is a diagram showing an example cross section of another design of an example aligner where the aligner fits into a groove of the divot anchor, and in which the aligner has a rib design or circular groove that is not possible to make by conventional thermoforming aligner manufacturing methods.

FIG. 11 shows a cross-section of an example aligner that has a piece, member, rib, or tab that fits into groove of the divot anchor, such as groove E in FIG. 5. The example aligner may have a rib design or a circular groove, which is not possible to manufacture by conventional thermoforming or conventional CAD/CAM methods. Only 3D-printing allows manufacture of the example aligners.

Figure 12:
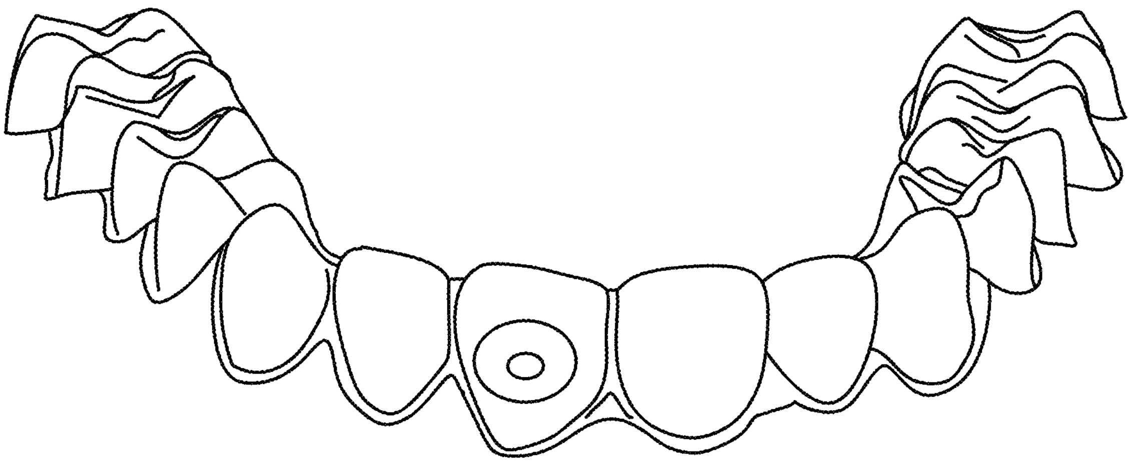
FIG. 12 is a diagram showing an example aligner appliance for use with the example divot anchor as mounted on a tooth.

FIG. 12 shows an example aligner for use in conjunction with an example divot anchor mounted on a tooth, such as that shown in FIG. 8.

Example Full Control Anchors

Example anchors can provide three-dimensional control for realignment of misaligned teeth. Current conventional designs of the INVISALIGN aligner cannot have three-dimensional control of the teeth due to their manufacturing methods and design limitations.

In an implementation, an example aligner is based on principles of the Andrews' straight-wire appliance. The principles provide three-dimensional control of misaligned teeth (straitening the teeth) with removable, directly 3D-printed (additive manufactured) plastic aligners utilizing anchor points as described below. The benefits compared with conventional braces with wires are: easily removal, ease of cleaning, more predictable alignment, and easier tasking by the orthodontist.

Figure 13:
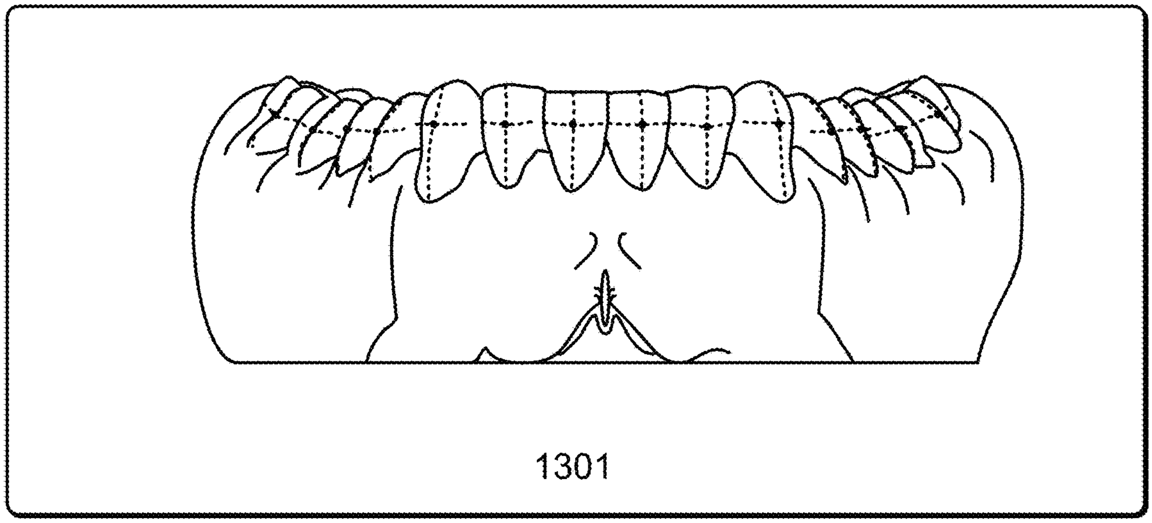
FIG. 13 is a diagram showing example front, left, and right views of an example reference point on each tooth, on the buccal or lingual surface, which when aligned makes the teeth come into alignment in three dimensional space, the reference point being referred to as a FA (Facial Axial) point.
Figure 13:
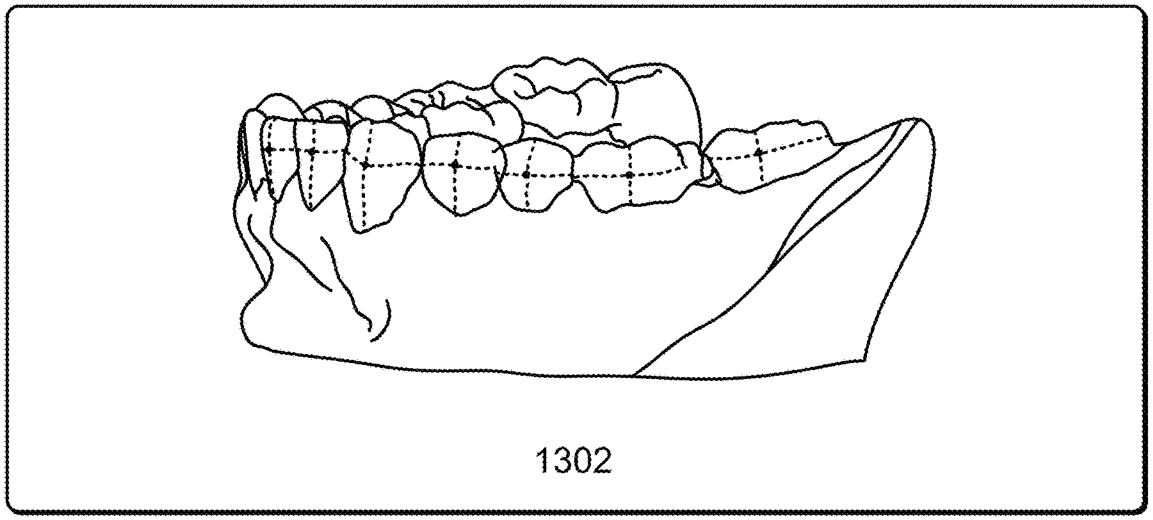
Figure 13:
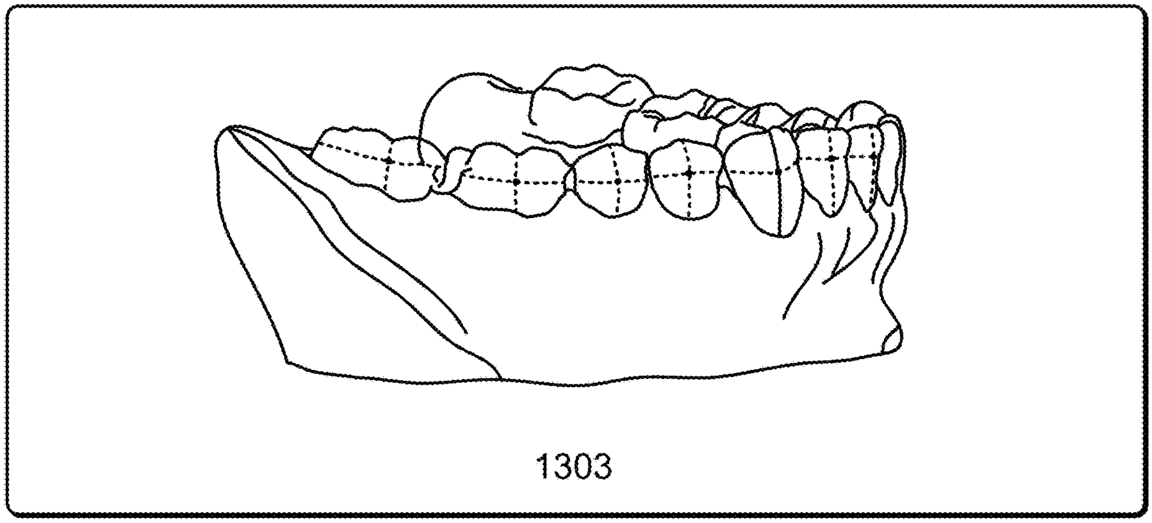

In an implementation, each tooth has a specific position in the arch and a relative position to the neighboring teeth. Each tooth can have a reference point on it, on the buccal or lingual surface, and when aligned makes the teeth come into alignment in three-dimensional space. This point is referred to as FA (Facial Axial) point by Dr. Andrews, as shown in FIG. 13 FIG. 13 shows the FA point view from front 1301, left 1302, and right 1303. These can be the primary reference points for placing the example anchors. The anchors are placed on this point or equidistance from this point either occlusal, gingival mesial, or distal on each tooth.

Figure 14:
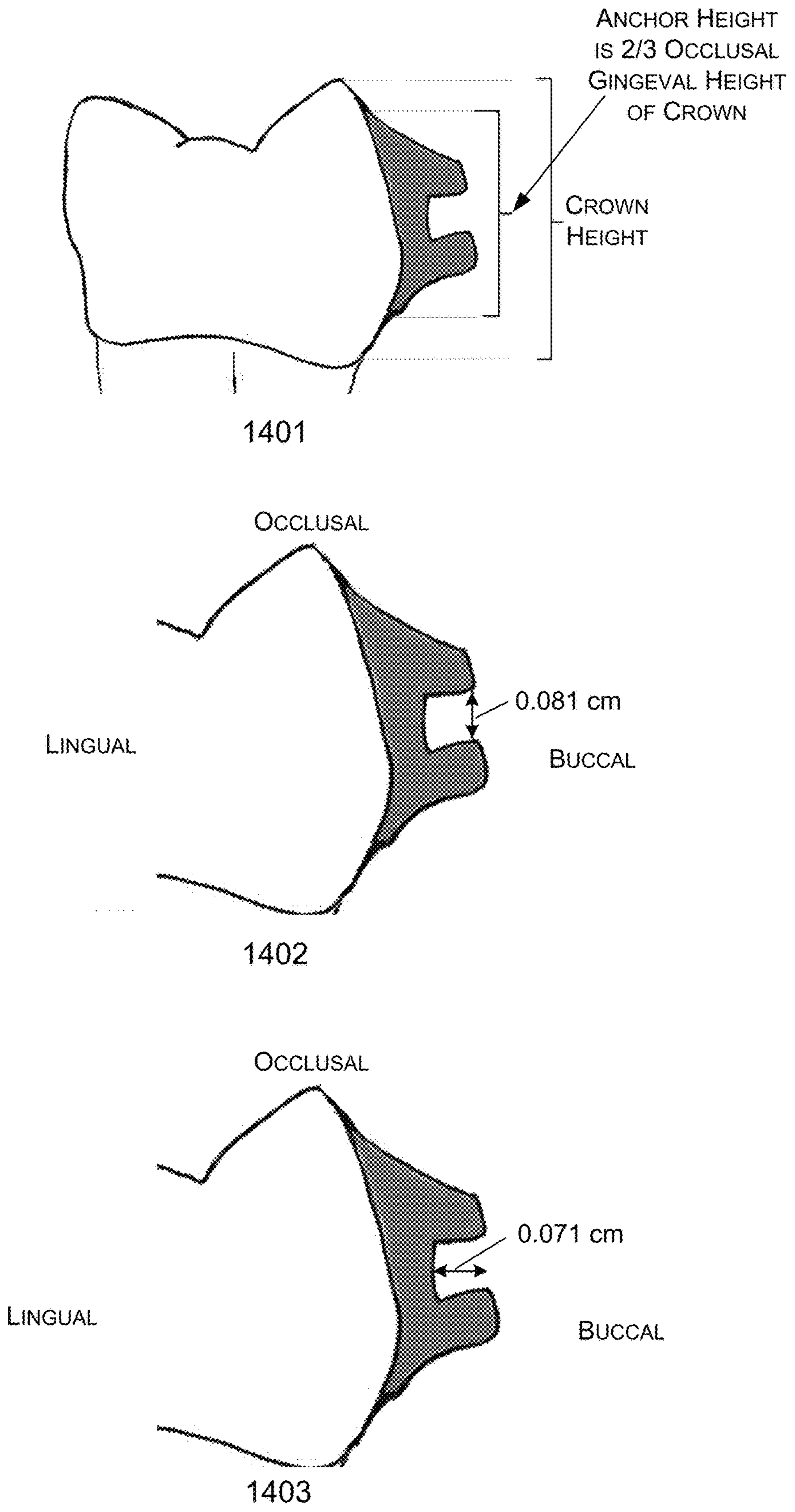
FIG. 14 is a diagram showing example anchor height, anchor slot height, and anchor slot depth parameters for example anchors for an example plastic aligner to fit onto.

FIG. 14 shows dimensions of an anchor, such as the anchor height 1401, anchor slot height 1402, and anchor slot depth 1403. The plastic aligner fits onto these anchors. Such aligner design is not feasible with current plastic aligners made by thermoforming or other conventional processes. Only 3D-printing allows the manufacture of such designs as shown in FIG. 14. In an implementation, the anchor height is ⅔ the occlusal gingival height 1401. The anchor slot height 1402 may be 0.81 cm. The anchor slot depth 1403 may be 0.71 cm.

Figure 15:
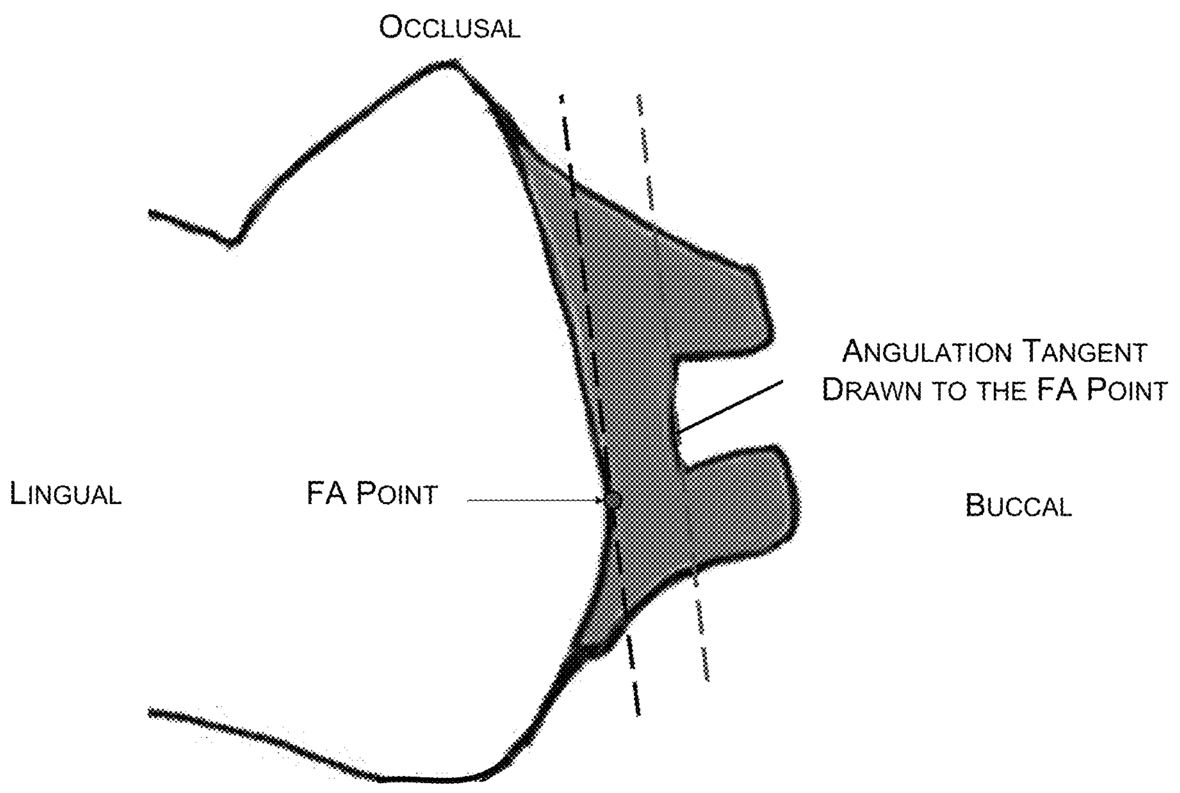
FIG. 15 is a diagram showing an example anchor slot angulation parallel to a tangent drawn on the buccal surface passing thru an FA Point introduced with respect to FIG. 13.

FIG. 15 shows anchor slot angulation: parallel to a tangent drawn on the buccal surface passing thru the FA point.

Figure 16:
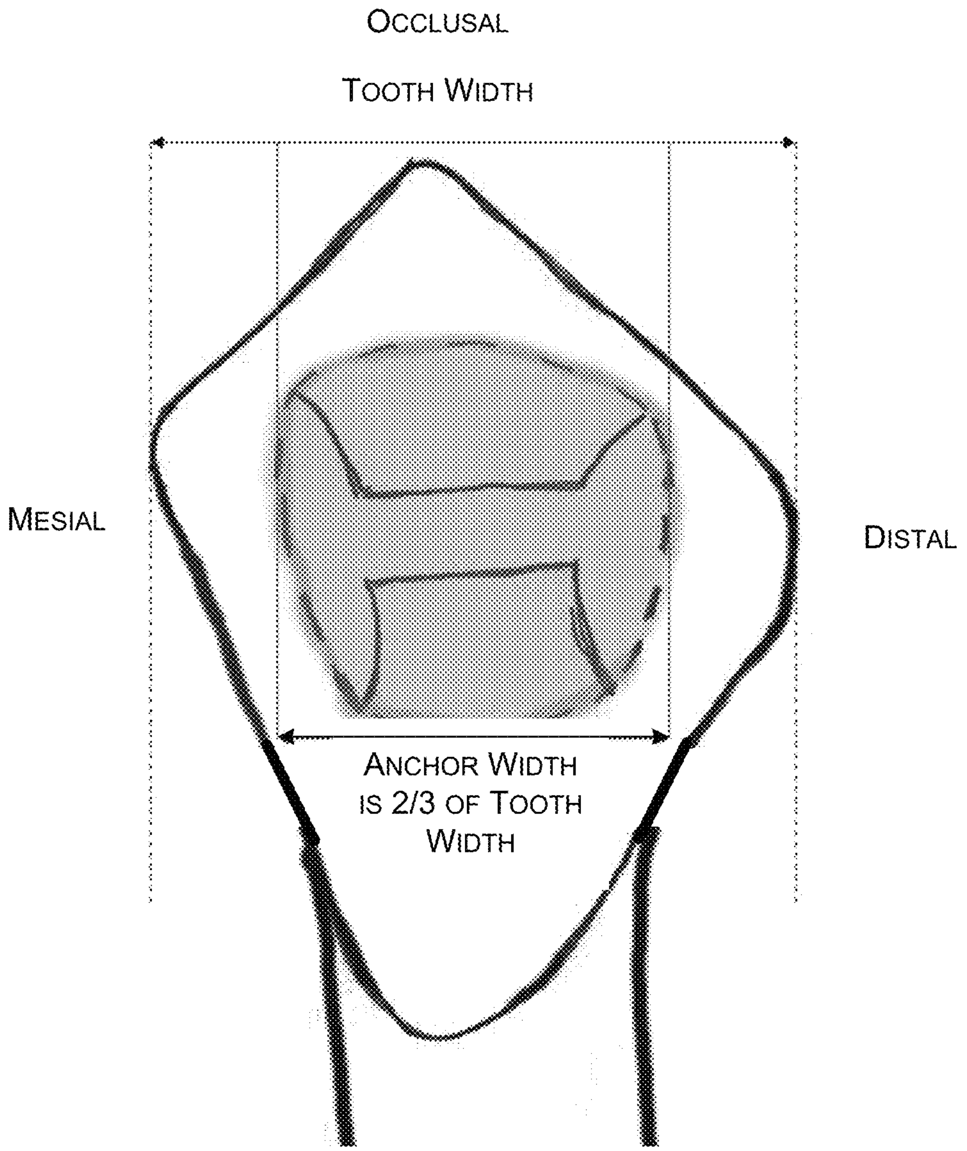
FIG. 16 is a diagram showing an example width of an example anchor, which is, for example, ⅔ the size of the tooth, with the center of the arches placed to the center of the tooth mesiodistally.

FIG. 16 shows an example width of the anchor which can be ⅔ the size of the tooth with the center of the arches placed on the center of the tooth mesiodistally.

Figure 17:
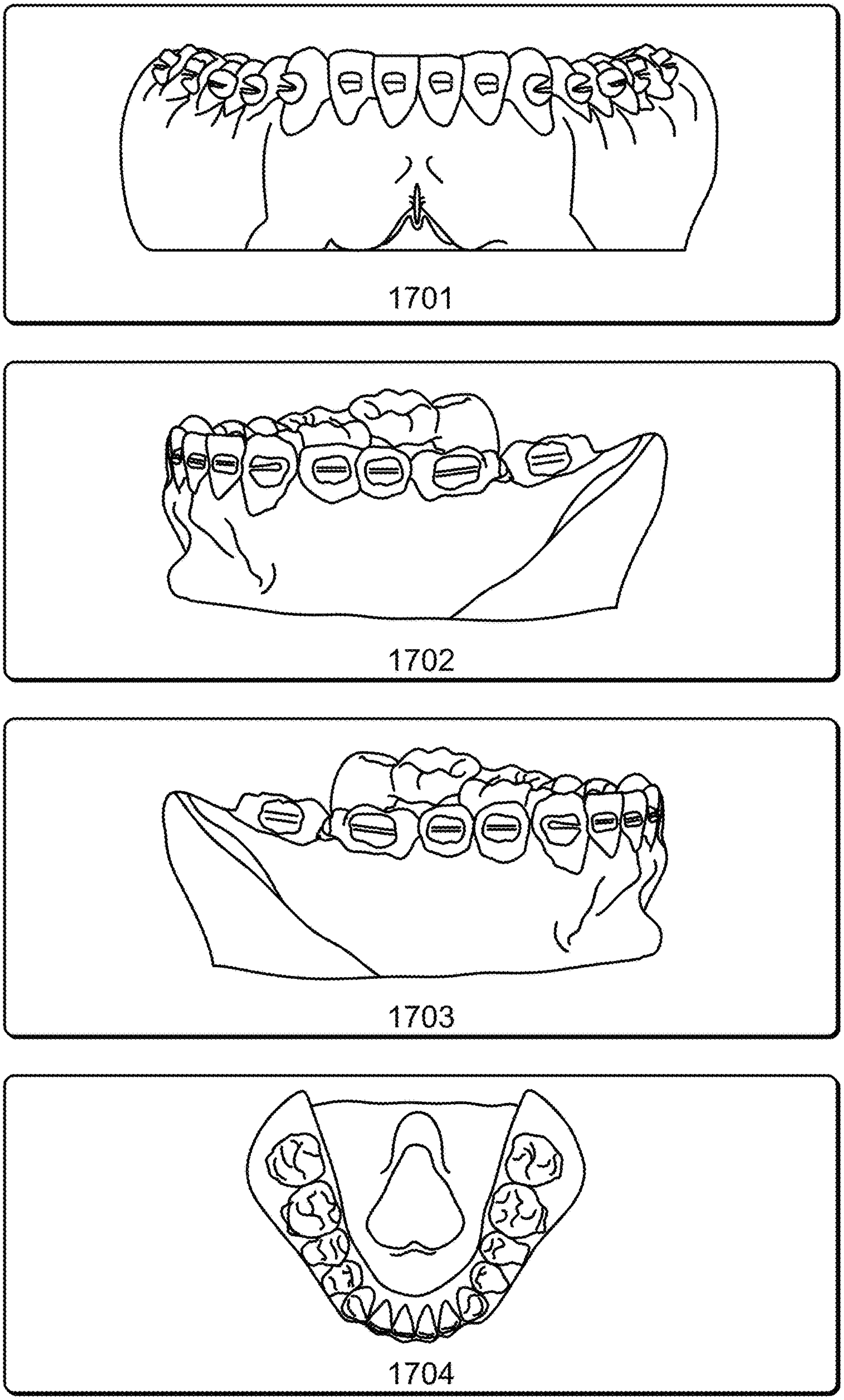
FIG. 17 is a diagram showing example shows 3D models with anchors placed on them to show how appearance from front, left, right and top.

FIG. 17 shows three-dimensional models with anchors placed to show an appearance from the front 1701, the left 1702, the right 1703, and the top 1704.

In an implementation, the following are steps for placing anchors on teeth:

1. First align the teeth digitally to their final position in a computer model or virtual model.
2. Calculate anchor points to be placed on each tooth or necessary teeth to be moved at the predetermined point FA point or a point in relation to this point consistent on all the teeth, digitally.
3. Determine each anchor point to have a movement prescription in angulation, rotation, and torque and a buccolingual position built into it, as determined by final position of teeth on a digital or virtual teeth modeling set-up.
4. Once anchor points are determined on digital teeth, the anchors can be transferred to mouth teeth using an aligner transfer tray.

Example Force System

An example approach for forces to be delivered by a removable plastic aligner is described. The approach starts with light forces applied to enable engaging the anchors to a first level of force, and to initiate alignment of teeth for progressing gradually (as treatment progresses, then the next series of aligners), then to an aligner that is rigid enough to applying correcting torque to the teeth. Retraction and space closure can be done simultaneously or in stages.

Forces are generated by gradually increasing the stiffness of aligners (from soft initial aligners to rigid aligners as treatment progresses). This concept is only possible by use of different materials and direct 3D-printing, as conventional plastic-working processes will not be able to make an aligner with different dimensions within the same aligner, or different pre-defined thicknesses within the same aligner; or soft/hard materials at variable thicknesses at pre-defined locations within the same aligner.

Properties of the 3D-printed plastic aligner materials need to be consistent with the following metal arch wire parameters to produce force levels of around 26 $gm/cm^2$ of root surface: 0.014 nitinol (0.014-inch diameter) or 0.018 nitinol (0.018 inch diameter) or 18×25 nitinol (rectangular) or 18×25 steel (rectangular).

These values can be achieved by addressing the modulus of elasticity of the plastic aligner material, selecting the correct force deflection curve of plastic aligner materials to match metal arch wires, controlling the thickness of the aligner, the cross-section of the aligner, and the engagement of the aligner in the anchors.

Due to 3D-printing processes, aligners are designed with smooth edges so aligner does not irritate the patient's gingiva and/or tongue, so soft tissues do not become inflamed or blend. The process also allows no sharp flange at the base of aligner near the gingival margin particularly on the lingual side, as no trimming operation is required, but which is the part of the conventional aligner manufacturing process (i.e., thermoforming of plastic film, followed by trimming, cutting, deburring, and a smoothing operation, etc.)

Some of the example divot anchor designs described herein can also be used in conventional manufacturing of aligners, i.e.; thermoforming a plastic sheet/film on 3D-printed dental model or conventional dental model, where a simple design of a divot anchor is sufficient, or other reasons decided by the dentist or orthodontist.

The example designs, compositions, and geometries of the example 3D-printed aligners are an important part of example orthodontia systems, particularly the anchoring design of the aligners, to move teeth at pre-designed positions and apply force at predefined locations on a tooth. So the design of example aligners based on anchor design is significant since the aligner has to fit on the divot anchor and the two components have to work in conjunction with each other, as well as the aligners have to be manufacturable by 3D-printing processes.

Other example design innovations, materials, and processes are described below.

Specific additive manufacturing processes, or 3D-printing technologies with specific support structure during 3D printing, may be specifically required for particular aligner designs. Likewise, specific material formulations and combinations may be called for. The direct 3D-printing of aligners resolves several issues facing current conventional manufacturing methods. Example processes can direct 3D-print an aligner with thin or thick parts, an aligner having variable thicknesses at desired locations, hard or hard/soft aligners, aligner with different properties at different locations by design, or by using different materials within an aligner in a single step using 3D-printing processes such as FDM process, SLS process, direct pellets fused deposition process, DLP process, SLA, multi-jet photo cured polymer processes, HP Multi Jet Fusion Technology, the CLIP process, etc.

The aligner which fits on above concept designs can be made of single material with variable thicknesses at desired location to achieve desired tooth movement (i.e., differentially increase the thickness to change the amount of force with same material). Or, an example process may exert force regionally with changing thickness, incorporating a design concept or by changing material within the aligner.

An example 3D-printed aligner may exert a more effective force with better control of manufacturing and may have controlled thickness of the aligner in desired areas to exert forces needed to perform tooth movement in the desired direction based on size, root length, and surrounding bond support. This can reduce number of aligners needed for orthodontic treatment of the teeth.

Aligner can also be made of multi-materials with or without variable thicknesses at desired locations. Multi-materials can help to change the position of the vertical plane. One of the inventions is to alter the shape and structure of plastics to exert force regionally, by torqueing or pushing the teeth up.

The invention also includes use of multi-materials in the aligner layer-by-layer through thickness in vertical position or horizontal position during same cycle of manufacturing.

One example aligner design uses different modulus of elasticity materials for teeth at the front (front teeth) and back part (back teeth) of the patient's arch. Another aligner covers the teeth at different levels (height). In an implementation, hard and soft aligners are 3D-printed separately, bonded together, or hard and soft are printed in the same 3D-printing step on top of each other.

In an example process, the properties of an aligner (as a whole or at desired localized area) are modified after manufacture by exposing the aligner or its parts to different energy sources such as electron beam, microwave, UV light, LED curing light, etc.

An example aligner can be clear, white, or tooth colored, for example. White or tooth-colored aligners may allow the aligner to fill pontic spaces (missing teeth) by directly 3D-printing dummy teeth. The tooth-colored aligners can be made by adding pigments or color in the base plastics, or by painting or coating the aligner after it is manufactured by a 3D-printing process. One can also incorporate decorative or identification features. A polymeric medical grade coating can be applied after the aligner has been manufactured by some of the additive processes where it is desired to reduce surface porosity and improve surface smoothness. In an implementation, specific polymeric coatings with high molecular weight can be applied to increase the properties such as MOE after the example aligner is fabricated.

The invention shows how to cover the teeth at different levels, or some teeth, or leave an area not to be covered. The treatment can start with a series of aligners with hard followed by soft and so on. Three-dimensional control of misaligned teeth may start with a soft aligner.

One can have day and night appliances separately, where night appliance can have different thickness. It is also possible to adhesively join or ultrasonically weld 3D-printed hard and soft appliances to get a single aligner having hard/soft surface parts.

The patient should typically wear the aligner all the time except eating food or drinking hot liquid. Patient compliance is a major issue. One of the innovations is to incorporate die or pigment into plastic or coating of one of the molar internal teeth with this coating containing this dye or pigment. This die or pigment works as sensor, the color slowly goes away as time passes in the presence of mouth fluids (As color fades away, it indirectly tells patient or dentist the time duration aligner was in mouth). This may increase the compliance of wearing the aligner. If the patient is wearing the aligner as planned, and if dye fades away, it means that particular aligner has done its job, patient does not have to keep on wearing the aligner, it tells patient to switch to next aligner, which can significantly reduce treatment time for patient. Also, this dye concept can help dentist to determine if teeth movement is not occurring as planned. A micro-chip with small embedded sensors (such as temperature sensor) may also be included in an aligner to detect tooth movement over time and the compliance level of the patient.

An example aligner may incorporate a microchip on the aligner (inside at interface between aligner and tooth) with a force sensor that measures the forces that act on the tooth interface. The aim is to give feedback how well aligner is functioning, reduces the duration of therapy, related expenses and discomfort of individual as well as compliance information. A micro-sensor can be placed on a divot attachment to measure load/force values to see performance of the aligner as predicted by software and provide information remotely to orthodontist as well as patient.

An example aligner may have 3D-printed school logo or other design, or a very thin low modulus film with different designs which can be attached onto it for better appearance.

The aligner may function as sleep apnea or anti-snoring device by connecting the upper and lower aligners together and moving the lower jaw forward or making upper aligner with front hollow housing and side half round hollow tubes or center tube from the front housing which can bring more air while breathing, opening the air passage, reducing the snoring.

The aligner can also be used as mouth guard and night guards to prevent grinding of teeth.

The innovative material(s) and design of aligner is elastic in nature which means it exerts comfortable force when patient wears it and upon exert of force the aligner may extend/stretch but returns to original position to exert a gentle constant force to help programmed teeth movement. The material should not relax and lose energy in initial days of aligner wear. The thermoplastic material that exhibits substantial linear elastics behavior with a high yield point is more desirable. Creep, fatigue and dimensional stability properties of polymers are also important.

Proposed materials for thermoplastic 3D printing process are polyurethane (TPU), polyamide, polyester or co-polyester such as PETG, polycarbonate, PMMA, polypropylene, polyether sulfone (PES), PLA, Polyolefins etc. For thermoset 3D-printing processes such as SLA, DLP etc, photopolymer acrylic resins and epoxy/urethane resin can be used to achieve the desired material properties.

One of the materials that can be 3D-printed is self-reinforcing plastics. The benefit of this material that it does not have fibers, but the polymer itself helps in controlling the aligner's properties. This material has a high elastic modulus, no deformation after desired strain, toughness, and high strain at break.

The plastic powder particle size for SLS process is very important to have dense fusion. The particle size is in the range of 20-100 microns. Less than 50 microns is preferable. Bulk density of powder is in the range of 0.20 grams/cm3 to 0.40 grams/cm3 as per ASTM D1895. It is important that the aligner does not crack during finishing process. High polymer powder fusion characteristics is very important for powder 3D printing processes such as SLS and Multi-jet fusion One of the inventions is to combine different family of plastics/polymeric powders, hard and soft, (as an example—Polyamide (hard) with TPU—soft) having very close particle size distribution to obtain desired modulus of elasticity and more isotropic properties and softness of aligner where desired (same properties in X, Y and Z direction, which is difficult to achieve in case of SLS and multi-jet fusion process).

To achieve the above-mentioned design concepts using several 3D-printing processes, the innovative developed materials may have the following properties:

The materials may have biocompatibility as per DIN EN ISO 10993 and US Type VI standards.

Hardness—Shore D scale of 40-90 (DIN 53505)

Elastics Modulus—1000-1800 Mpa (ASTM 638-2010)

Tensile strength at yield—40-70 Mpa (ASTM 638-2010)

Tensile Modulus in the range of 1400 Mpa to 2000 Mpa (ASTM D638)

Off set yield stress—greater than 25 Mpa (ASTM 638-2010)

% elongation at break in the range of 10-200% (ASTM 638-2010)

Flexural strength—50-80 MPa ASTM D790

Flexural Modulus—1200-1900 MPa (ASTM D790)

Tear strength in range of 45 MPa to 60 Mpa

Energy to break—16-20 Joules

No deformation in the range of 0.5% strain over an 8-24 hour period

Stress relaxation rate (N/s) in the range of 0.010-0.020

Impact properties: Izod impact notched at 3.2 mm, 23° C.-3 to 16 kJ/m$^2$ as per ASTM D256 Test method A Properties as measured by nanoindentation tester (ASTM E2546):

Elastic (Young) modulus in the range of 600-2000 MPa

Hardness in the range of 40-160 Mpa, preferably the range is 40-80 Mpa

Creep (nm) in the range of 120-400 nm.

The orthodontic system may use a total digital or total virtual concept. The patient or orthodontist can take the digital impression using Nano intra-oral scanner, smart phone having attached extended camera or WiFi camera transferring the digital data to a smart phone or other device to create a .STL file of teeth. The camera may be independent of smart phone or other digital device (attached to phone by wire or wireless). Orthodontist or other dental professional can design series of aligners based on final desired teeth movement and can 3D print these aligners at his office during patient's first visit or can send .stl file to out-side service labs who 3D prints the aligners for orthodontist or dental professional. As teeth movement occurs, take digital impression again, make new aligners as described above or using available software, make series of aligners for certain amount of teeth movement before calling the patient back in office. This is less iterative, fast and low cost solution.

Above described total solution of innovations in design, innovation in materials and incremental process improvement open up lot of design freedom and options in treating the patient in short amount of time and certain non-feasible cases which are not possible now. It can be cost effective, more precise, and more comfortable to patient.

Example Processes

For FDM Process (Thermoplastics):

A new concept allows printing of different materials not only in X and Y direction but also in Z direction. Also using hybrid process, using robotic extruder heads it is possible to print multi-material during or after part is made.

The example system also includes use of single filament having two different molecular weight materials to get hard/soft aligner in a single step process. During 3D-printing, low molecular weight material which is soft comes on the surface. Or one can use two layer filament where outer layer is made of soft material. Inner layer is hard material of same polymer or different but compatible polymer. Or one can include additives which cures the polymer to higher molecular weight, after 3D printed FDM aligner is put in the microwave oven or exposed to other energy, increasing the strength in Z direction (without distorting the part For Powder based processes—SLS (selective laser sintering) or Multi-jet Fusion—Thermoplastics:

To get a hard and a soft material in same part, mainly to get soft or hard material on the surface of the part, example material formulations may be used. The material consists of low and high molecular weight materials in powder form. After the part is made by laser sintering or multi-jet fusion, the part can be exposed to high temperature, just below the melting point of low molecular weight material, this causes the low molecular or soft material to come on the surface, building very thin layer of soft material on surface. SLS process uses laser, while Multi Jet Fusion which does not use lasers. Here, the powder bed is heated uniformly at the outset. A fusing agent is jetted where particles need to be selectively molten, and a detailing agent is jetted around the contours to improve part resolution. While lamps pass over the surface of the powder bed, the jetted material captures the heat and helps distribute it evenly.

One example technique increases the modulus of the aligner as a whole or localized area by crosslinking of part after it is made or during the part fabrication.

Another example process adds a specialty coating, which provides a smooth surface.

An example technique combines different families of plastics powders (such as Nylon with TPU) having very close particle size distribution to obtain desired modulus of elasticity and more isotropic properties (same properties in X, Y and Z direction, which is difficult to achieve in case of current SLS process)

For SLA process (Stereolithography)—Thermoset:

In SLA process, the aligner to be made is either pulled out of a vat containing liquid material as it is solidified by a light source through a translucent window at the bottom (bottom-up), or it is submerged into the liquid as the top layer is treated by a light source from the top (top-down).

First the part can be made from one material, mainly photopolymer. Then, this part is inserted in the liquid of different material where other material is cured on the surface of first part. The invention is to get part with different softness and also additional features with second material.

DLP, or digital light processing, is a similar process to stereolithography in that it is a 3D printing process that works with photopolymers. The major difference is the light source. DLP uses a more conventional light source, such as an arc lamp, with a liquid crystal display panel or a deformable mirror device (DMD), which is applied to the entire surface of the vat of photopolymer resin in a single pass, generally making it faster than SL.

For FDM process, to increase properties in Z direction, the crystallization kinetics of the material are changed to get better heat retention and hence higher inter-layer bonding between layers in Z layers. This invention is only applied to crystalline or semi-crystalline polymers. This concept can be used with dual layers filament having core-shell structure as shown in FIG. 52(I) where core is B and shell is A. The shell can be crystalline or semi-crystalline polymers while core can be amorphous material. If both shell and core are crystalline or semi-crystalline polymers, the shell material can have higher crystallinity then core, to improve inter-layer bonding between layers in Z direction, hence the increase properties in Z layers and more homogeneous material properties in all directions To improve fusion properties and shrinkage properties of SLS or Multi-fusion materials, fillers like silica powder, glass microspheres etc., are added. To improve impact properties and reduce modulus of elasticity still applying constant force without aligner deformation, elastomers like TPE in rigid plastics like nylon can be added.

In another system, dual modulus material is used in the same part for SLA process, to get low modulus in certain area of the part, photopolymer is cured with laser beam with low frequency while rest of the part is cured with laser beam with high frequency to get an aligner with dual modulus with in the same part.

Figure 18:
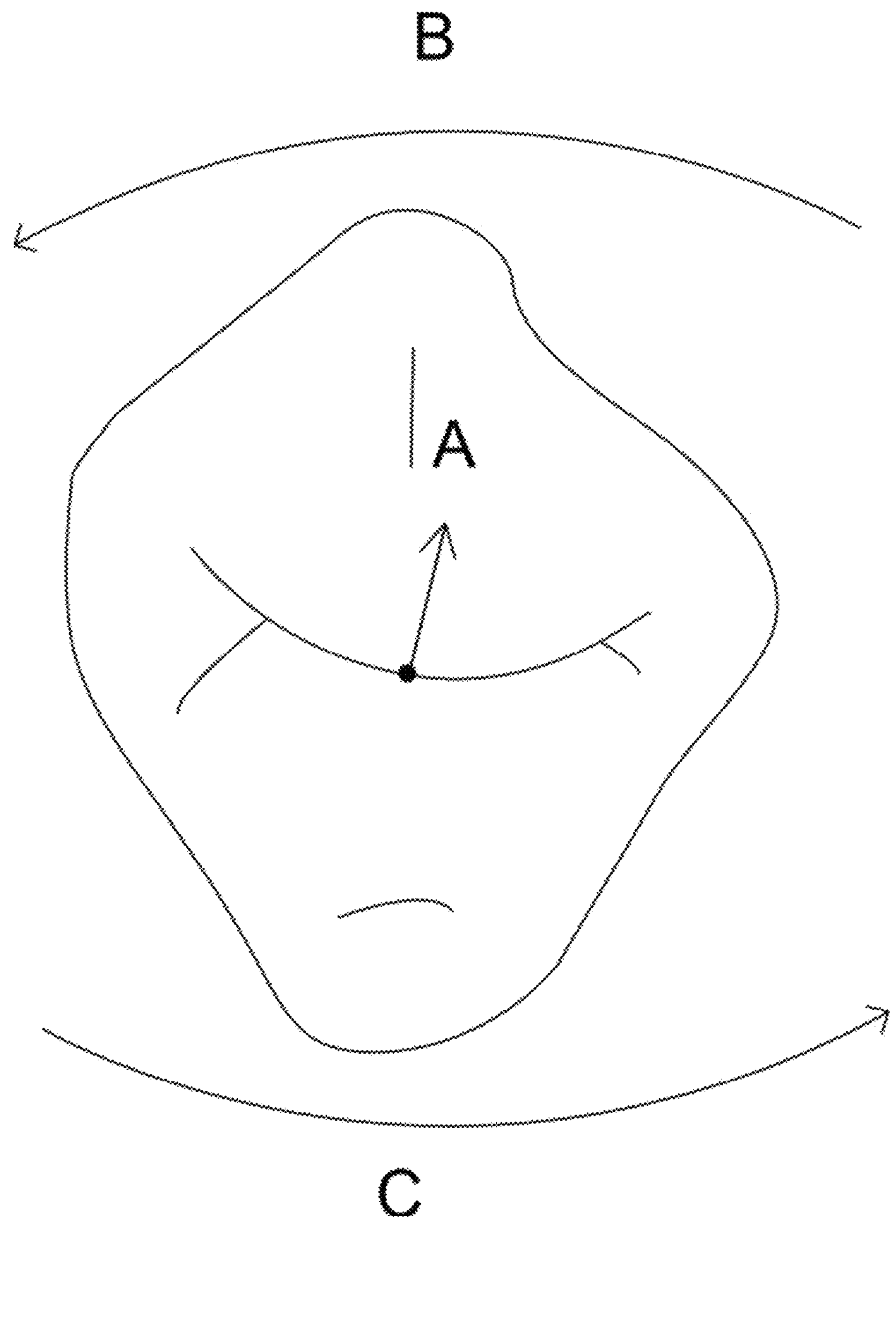
FIG. 18 is a diagram showing an example force distribution needed for effective rotation movement.

The various hardware described above, such as the example anchors and 3D-printed aligners, can be used to effect rotation for correcting tooth misalignment. As shown in FIG. 18, correction of rotation (of a tooth) in orthodontics is achieved by creating a couple around an axis of rotation (two equal and opposite forces B and C of the same magnitude acting around the same rotational axis A).

Figure 19:
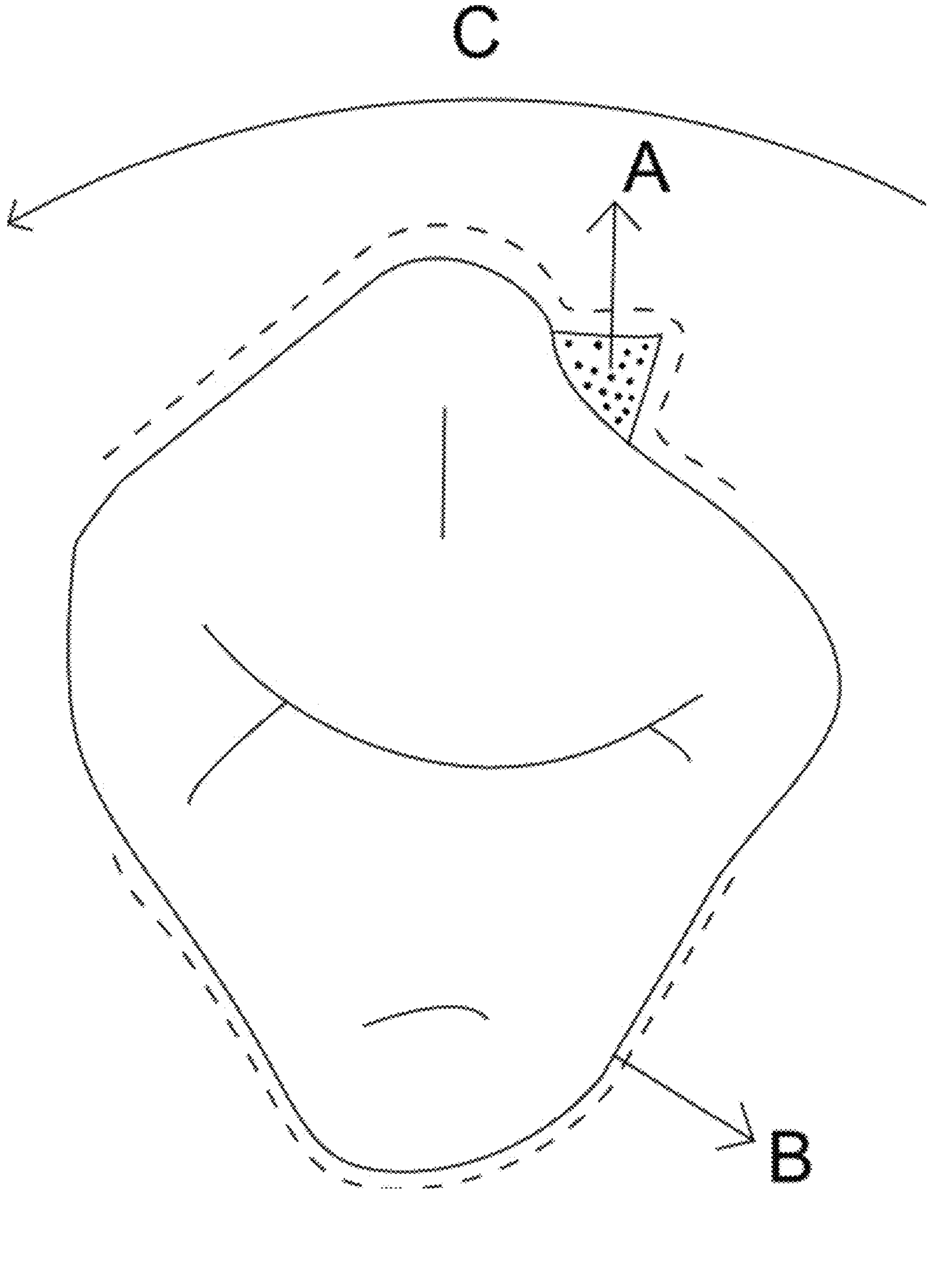
FIG. 19 (PRIOR ART)
FIG. 19 is a diagram of prior art showing conventional INVISALIGN mechanics, with the corresponding aligner made by thermoforming.

Currently with a conventional INVISALIGN aligner, correction of rotation is been achieved by a push rotation. As shown in FIG. 19, prior art, device A is an attachment on the tooth. The dotted line B shows an aligner and C is the force direction. Attachment A allows for force to be generated in a push direction C, but there is no force in an equal and opposite direction, as there is in FIG. 18.

Thus, the INVISALIGN aligner and other aligner designs on the market are very inefficient, further adding to a problem that there is too much resistance on the contralateral side (opposite side), because the conventional aligner contacts with the tooth.

The following describes three example designs for improving rotation correction. First, in FIG. 20, A is a divot anchor, the dotted line B is an aligner, C is a space for reducing resistance, D is force in one direction, and E is a spacer to reduce resistance in the other direction. In an implementation, a preferred method of manufacturing an aligner uses 3D-printing as such printing has a high degree of design freedom and other benefits as described. But, the example aligners for use in conjunction with one or more divot anchors can also be made by other CAD/CAM methods or even a conventional thermoforming process, if the particular design and costs permit. A conventional aligner cannot have thick section to fit into depression of the divot anchor (i.e., variable wall thickness, thick and thin), a conventional aligner only configures to the wall or outside plane of the depression of the divot anchor due to limitations of the thermoforming process. Example design and dimensions of a divot anchor are shown in FIGS. 1-4.

Using the described hardware, an example technique applies a pull force on the one side (for example on buccal side—the surface of a posterior tooth facing the cheeks) with a defined point of application using the divot anchor on the tooth. Placement of the divot anchor is easier that conventional placement of a rotation device, as shown in FIG. 20.

Figure 20:
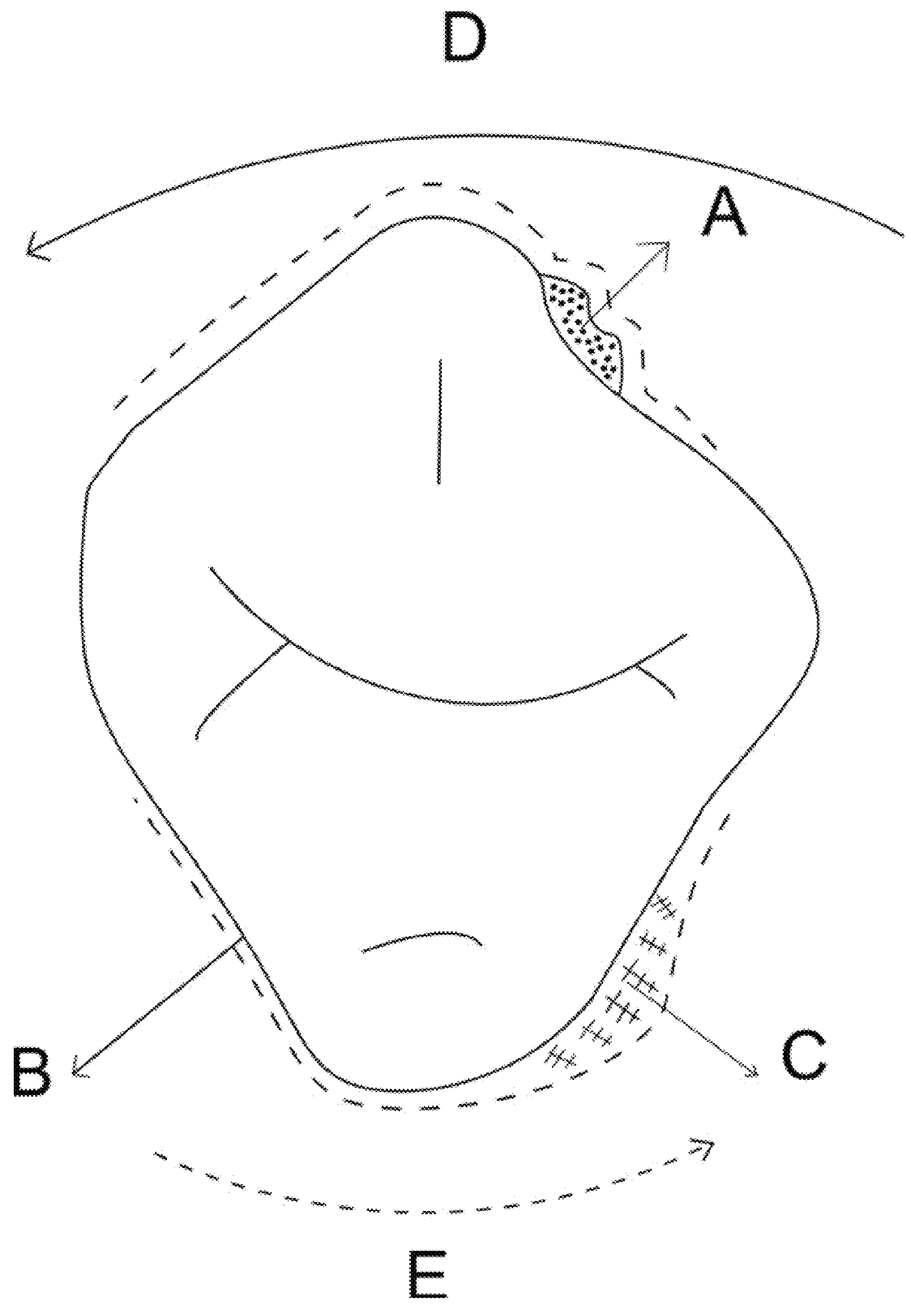
FIG. 20 is a diagram showing an example design to reduce reciprocal resistance in order to induce rotation caused by primary force.

As also shown in FIG. 20, the technique then includes creating a space for tooth to move on the lingual side (the surface of a tooth facing the tongue) ipsilateral position to reduce interference.

Figure 21:
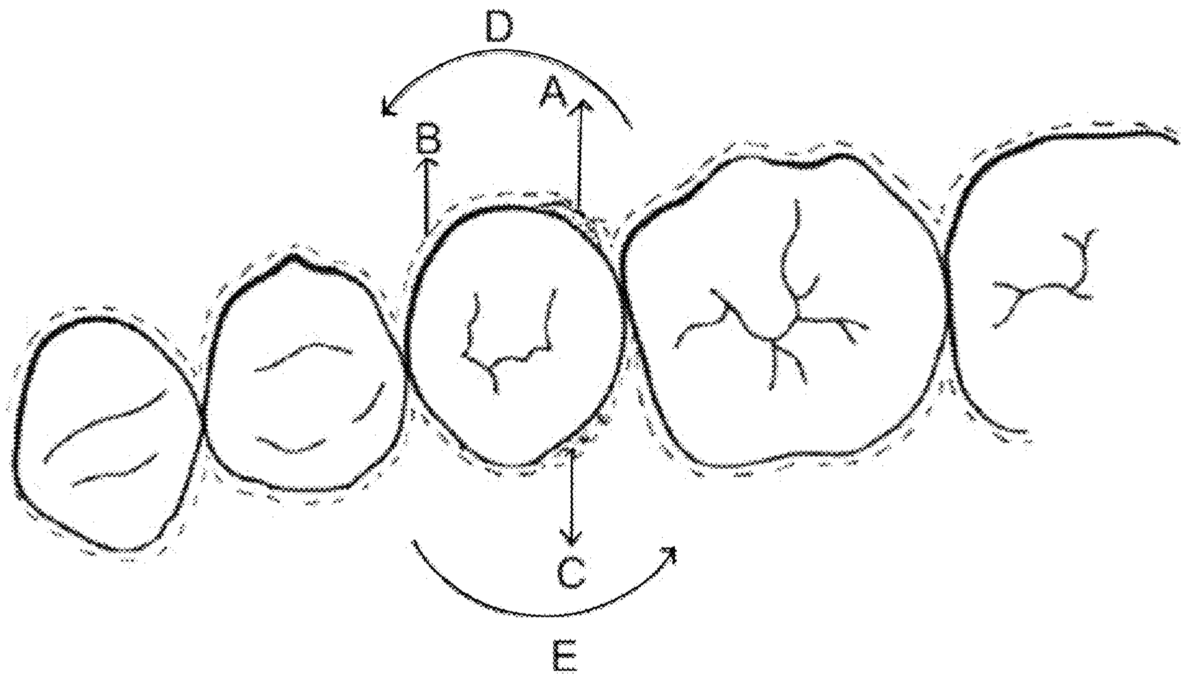
FIG. 21 is a diagram showing an example occlusal view of the concept of FIG. 20.

FIG. 21 shows a top view of teeth using the example set-up of FIG. 20.

Figure 22:
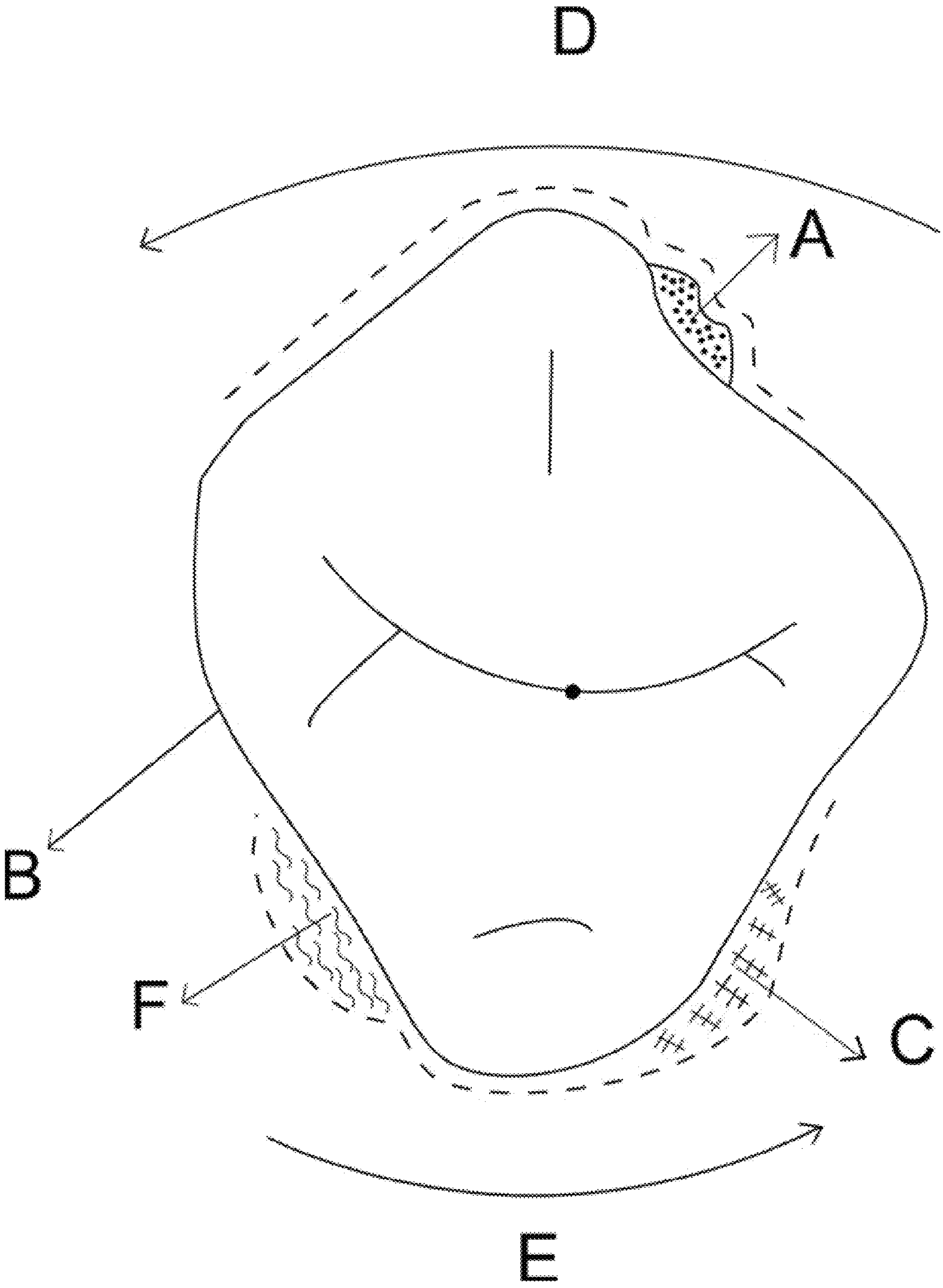
FIG. 22 is a diagram showing an example technique to produce equal and opposite force on the lingual aspect generated by soft aligner material diagonally opposite to an example divot attachment and spacer for allowing a tooth to move.
Figure 23:
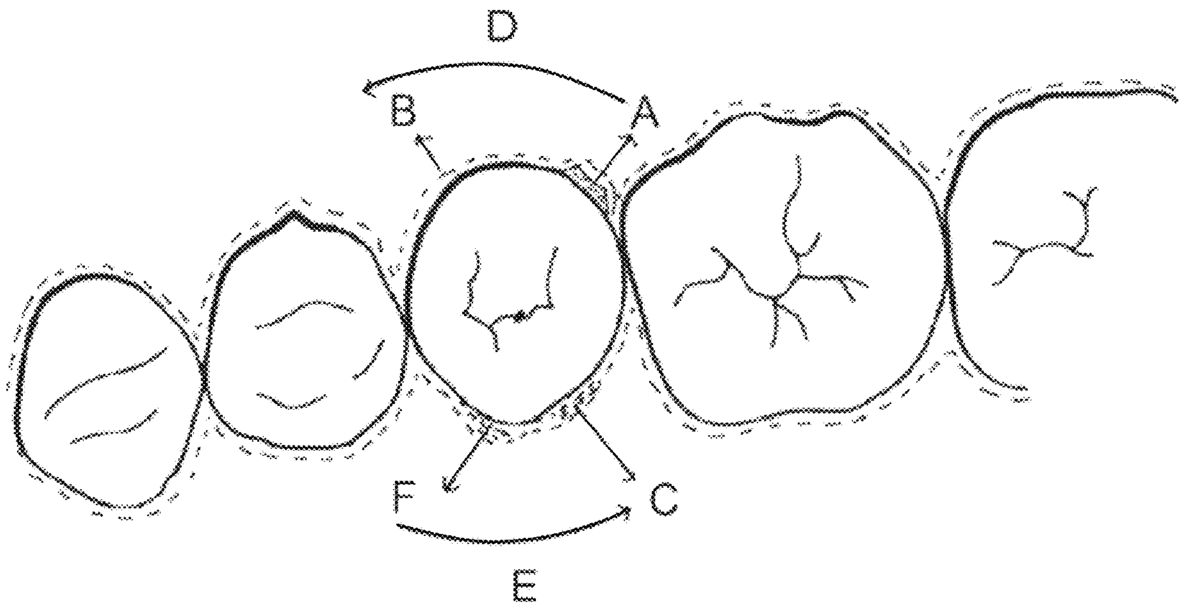
FIG. 23 is a diagram showing an example occlusal view of the concept of FIG. 22.

In a second example method for correcting rotation, the rotation control is achieved by creating a couple. As shown in FIG. 22, a space C reduces resistance to movement and F is soft reline material exerting an equal and opposite force. Force D and force E are equal and opposite forces created by the soft reline. So, this example rotation control using the couple concept is achieved by adding soft material F on the contralateral side diagonally opposing the buccal forces to act as another push component. FIG. 23 shows a similar top view.

Figure 24:
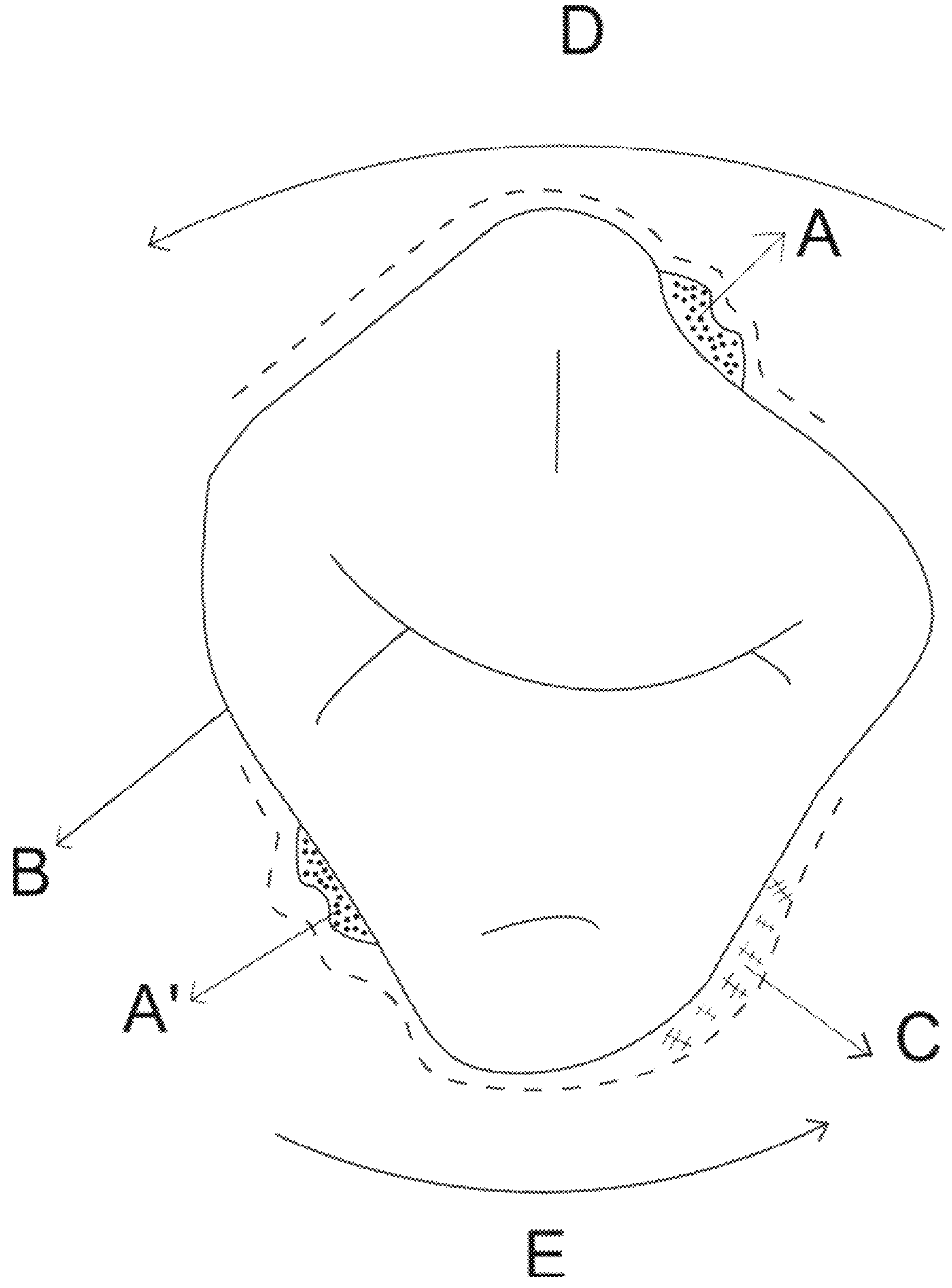
FIG. 24 is a diagram showing example force created by an attachment "A" and equal and opposite force created by second attachment "A" diagonally placed and a spacer to allow the tooth to move.
Figure 25:
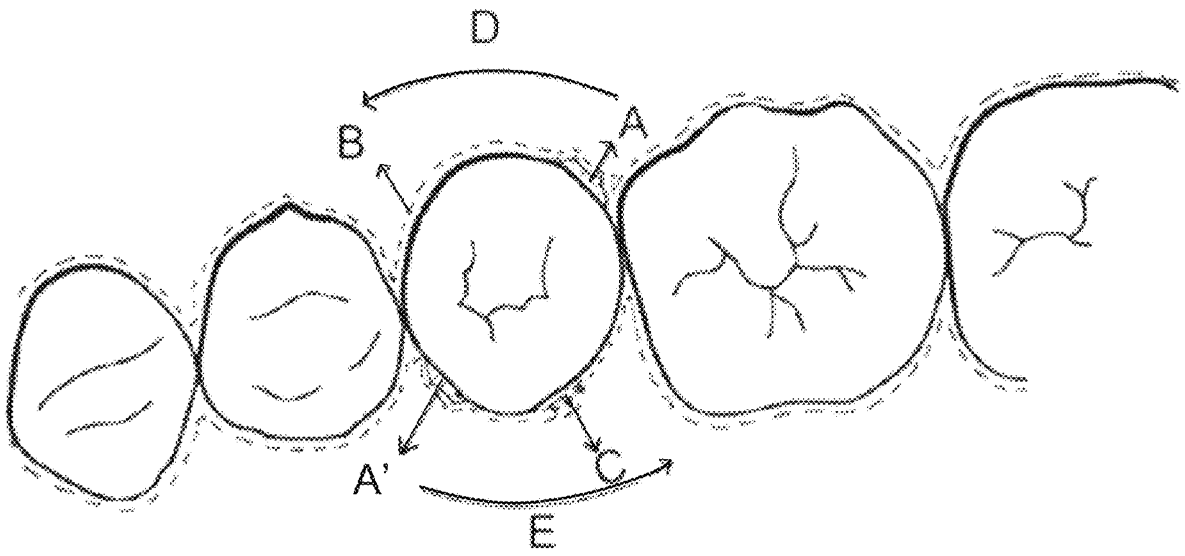
FIG. 25 is a diagram showing an example occlusal view of the concept of FIG. 24.

Another way to achieve this aim is to add a divot anchor on the lingual side also (the surface of a tooth facing the tongue). This scenario is shown in FIG. 24, where A is the divot anchor and A' is a second divot anchor diagonally opposite on the opposing side of the tooth. FIG. 25 shows a top view of this concept, showing multiple adjacent teeth.

Figure 26:
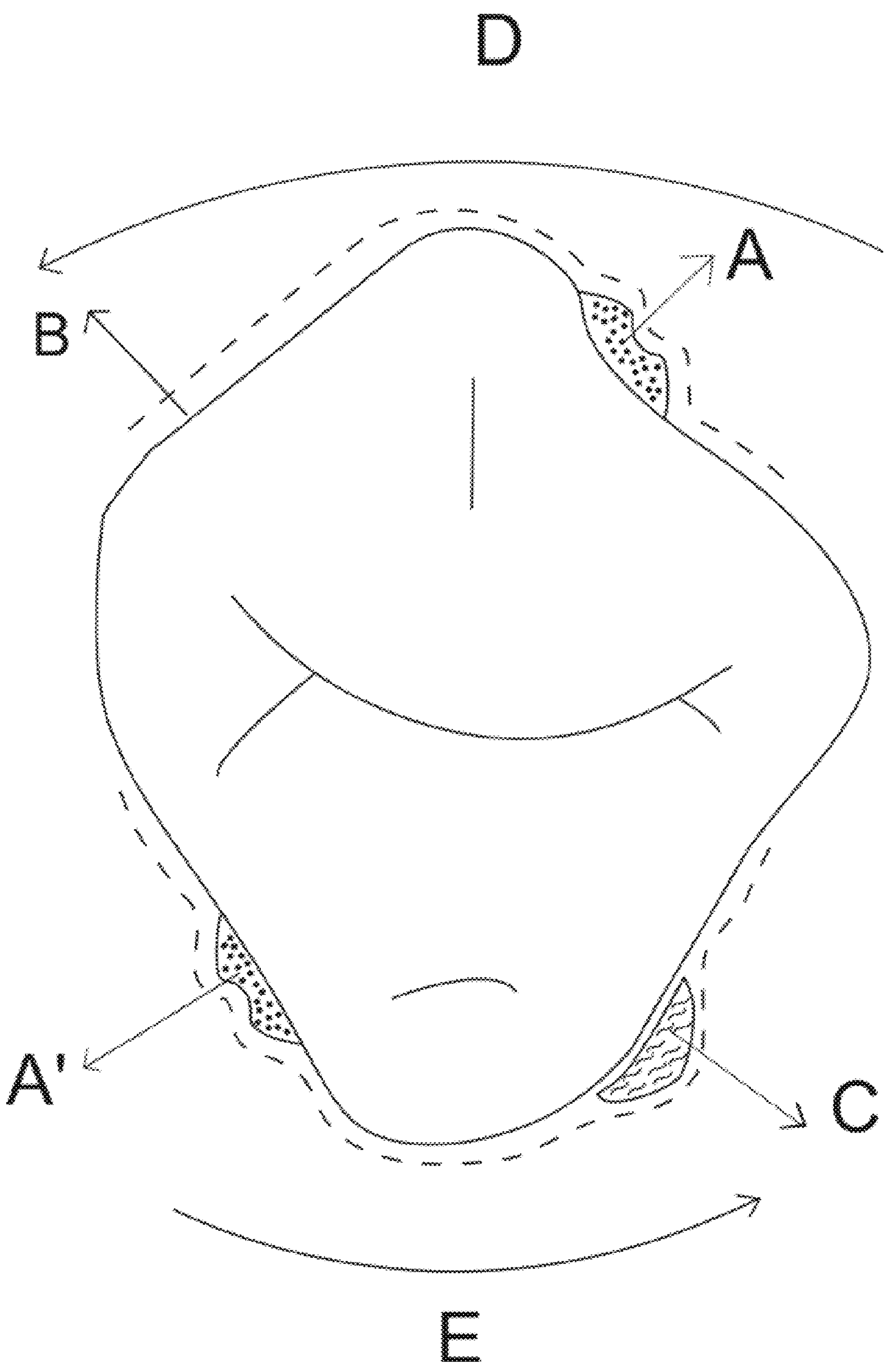
FIG. 26 is a diagram showing an example rotational movement created by a force generated at example divot anchor "A" and reciprocal movement created by second anchor "A" and movement enhanced by a pull force via suction cup attachment "C."
Figure 27:
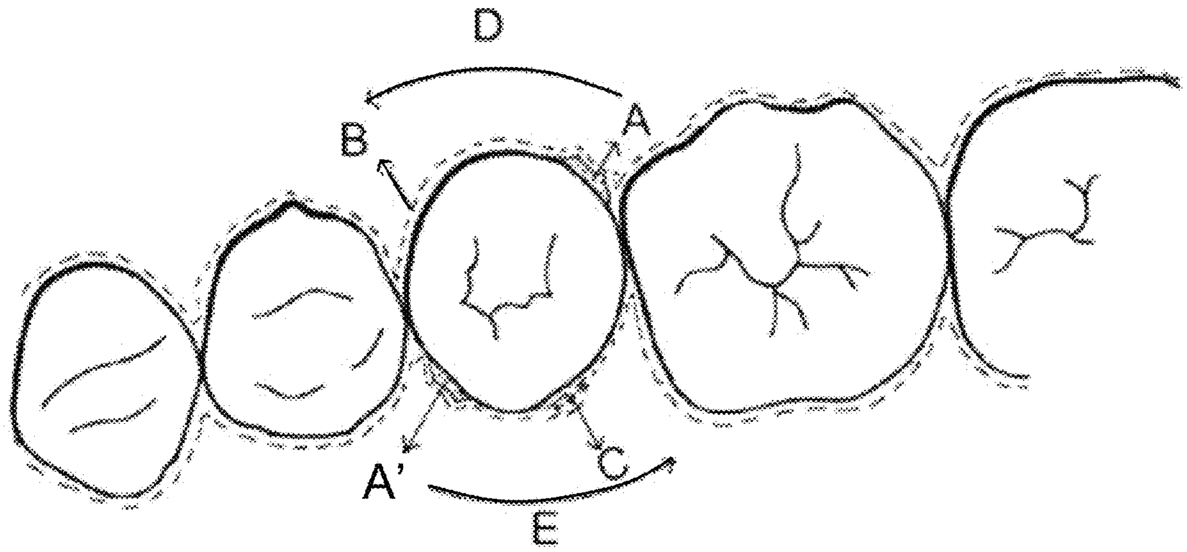
FIG. 27 is a diagram showing an example occlusal view of the concept of FIG. 26.

The third example method for correcting rotation includes adding a soft material on the lingual surface on the ipsilateral side, the soft material being designed to act as a suction cup. The concept is shown in FIG. 26. Divot anchor A and divot anchor A' are diagonally opposite on the tooth. B represents an example aligner and C is a spacer to reduce resistance. C can be a honeycomb suction cup made of soft material or other design and material that can provide the suction. D is a rotational force and E is an equal and opposite force rotational force. There are various materials and design concepts for creating suction to the aligner. FIG. 27 shows a top view of this concept, showing multiple adjacent teeth.

Figure 28:
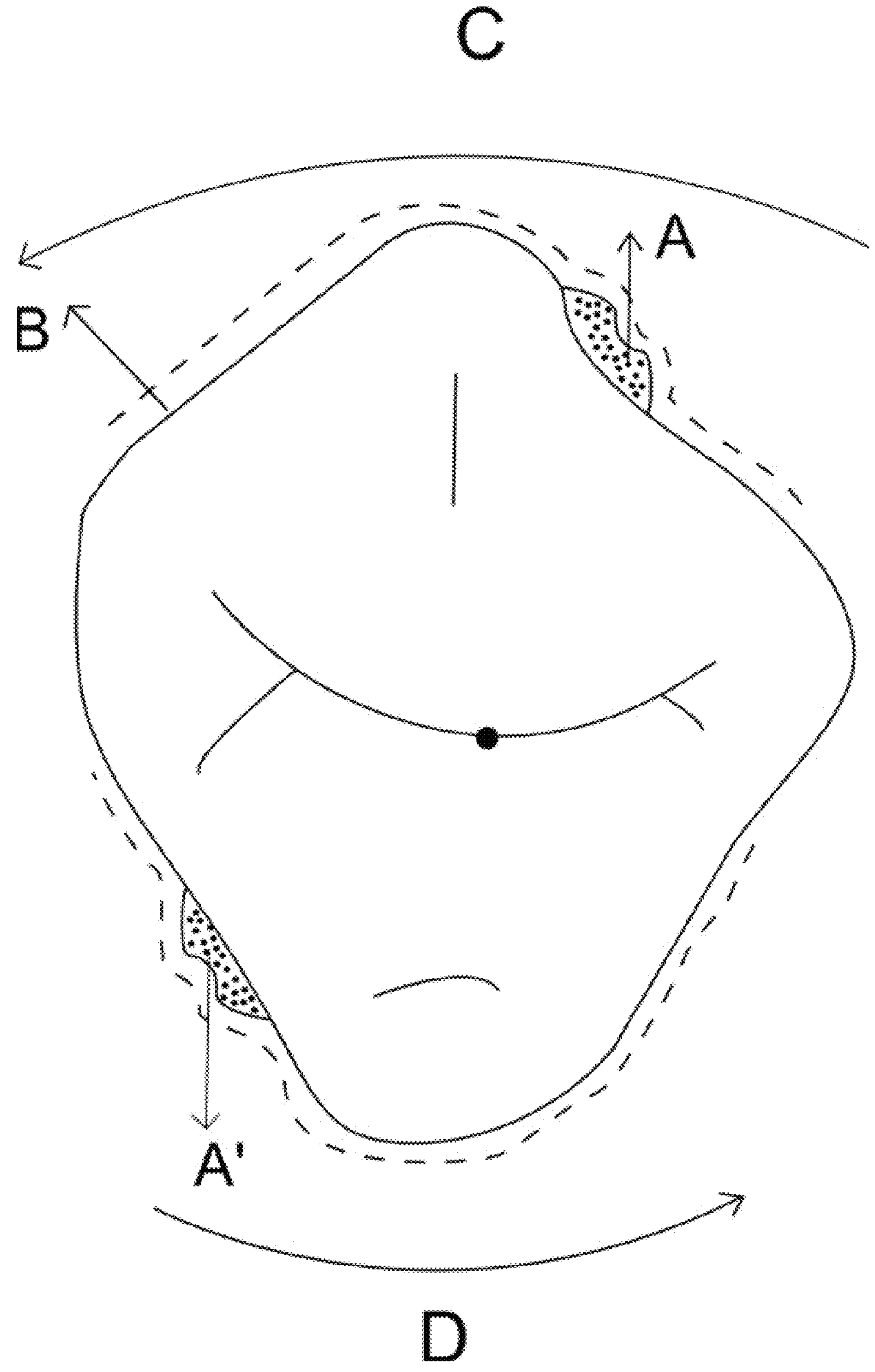
FIG. 28 is a diagram showing an example force created by attachment "A" and equal and opposite force created by second attachment "A" diagonally placed.
Figure 29:
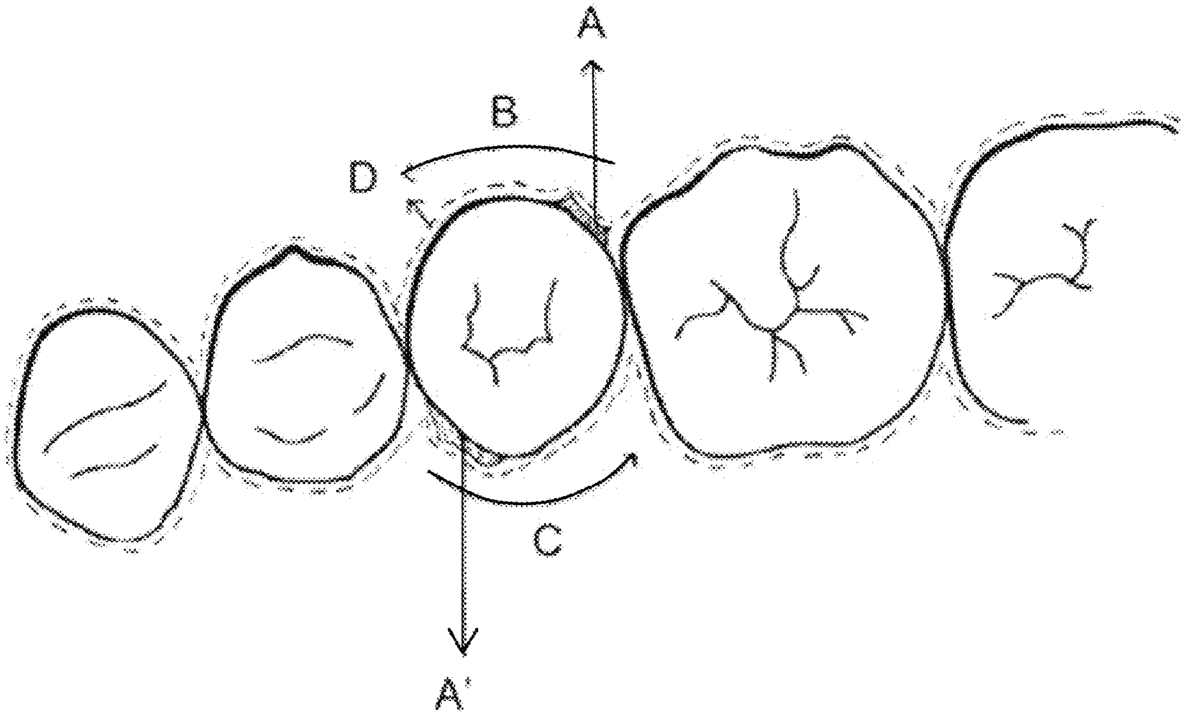
FIG. 29 is a diagram showing an example occlusal view of the concept of FIG. 28.

FIGS. 28-29 show the same concept as in FIG. 24, but with no space provided for reducing resistance.

Advantages of an example divot anchor include:

Smoother to tongue and cheek

Provides a more precise area for force application

Since the divot anchor is flatter than conventional, it can be placed in areas where there is less space On anterior teeth, the divot anchor can be made into a rectangle (simulating a bracket slot of a conventional orthodontic bracket). Applying force to the soft material can be delivered by lining the aligner with soft material.

Torque Control of Anterior Teeth

Figure 30:
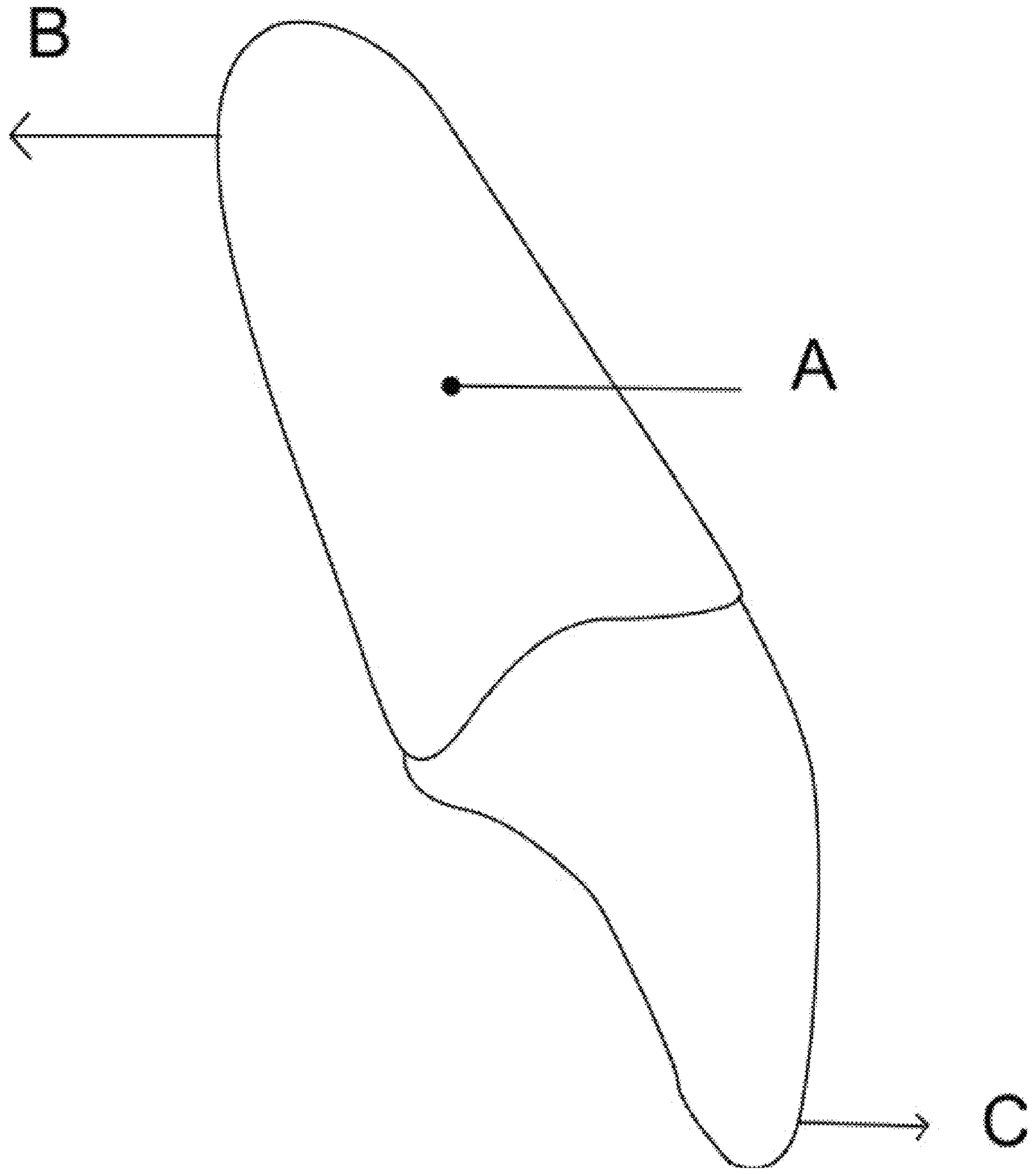
FIG. 30 is a diagram showing example forces required for torqueing roots of teeth.

As shown in FIG. 30, A is a center of resistance, B is a root moving palatal and C is reciprocal crown movement. This type of movement is needed for a tooth so that the root moves to the center of an alveolar process.

Currently, with conventional braces, torque is created in teeth by applying force in a labial-lingual direction. Although the intention is to move the root either in buccal or lingual directions, the crown always needs to move in the opposite direction, although not as much in magnitude. To achieve this movement, there should be complete engagement of the wire (the source of force) into the bracket and the system should be rigid.

Figure 31:
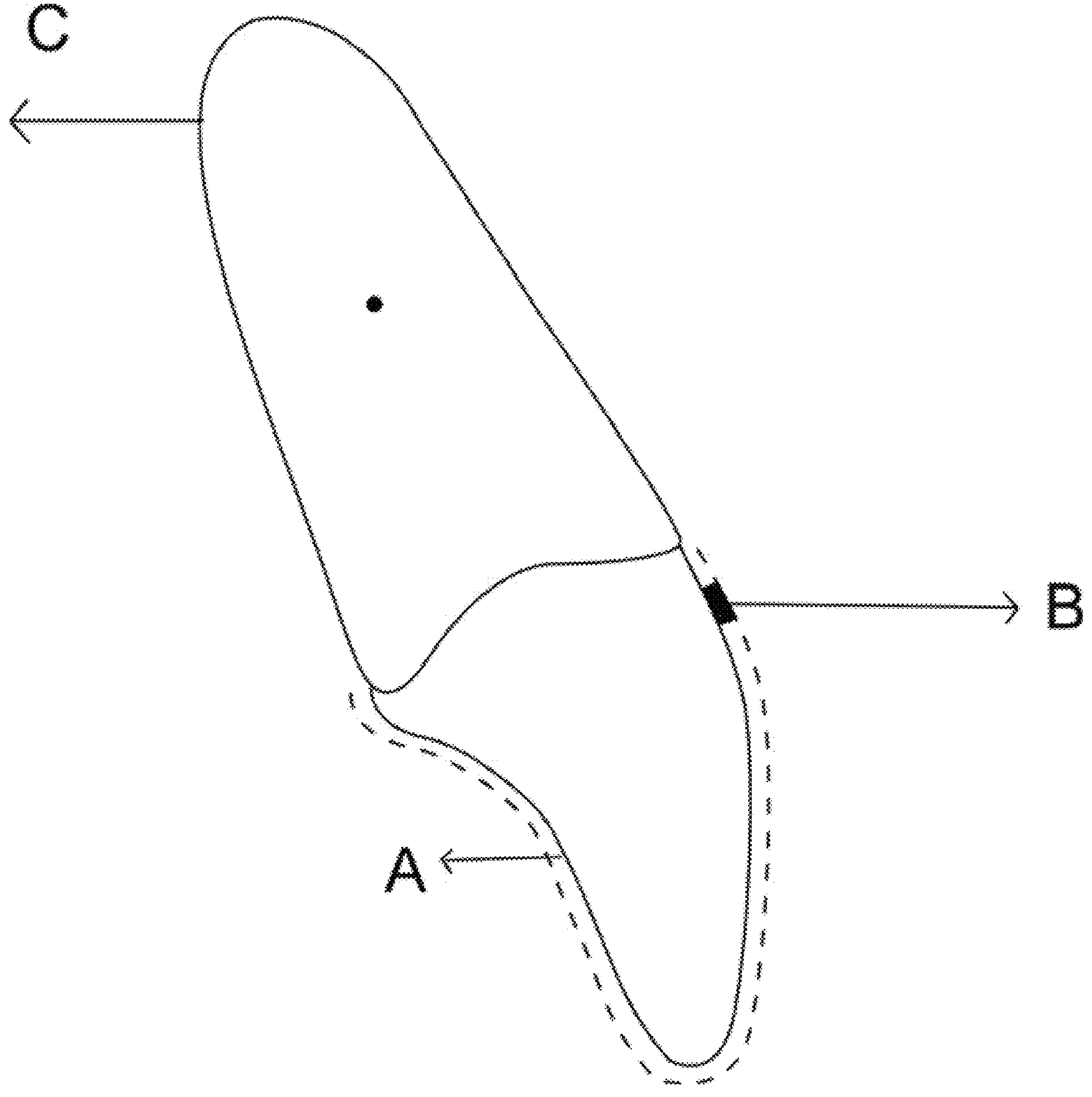
FIG. 31 (PRIOR ART)
FIG. 31 is a diagram showing a prior art torqueing mechanism of an INVISALIGN thermoformed aligner.

The conventional design of the INVISALIGN aligner applies torque by creating contact of the aligner towards the gingival one-third of the tooth with power ridges. FIG. 31 (prior art) shows this approach, in which A is a conventional aligner, B is power ridge, and C is the intended force direction. There is no room for reciprocal crown movement.

Disadvantages of the conventional aligner are that the power ridges do not have a definite point of engagement, and therefore the conventional aligner does not fit on the tooth completely, which in turn reduces the efficacy of the conventional aligner system.

Figure 32:
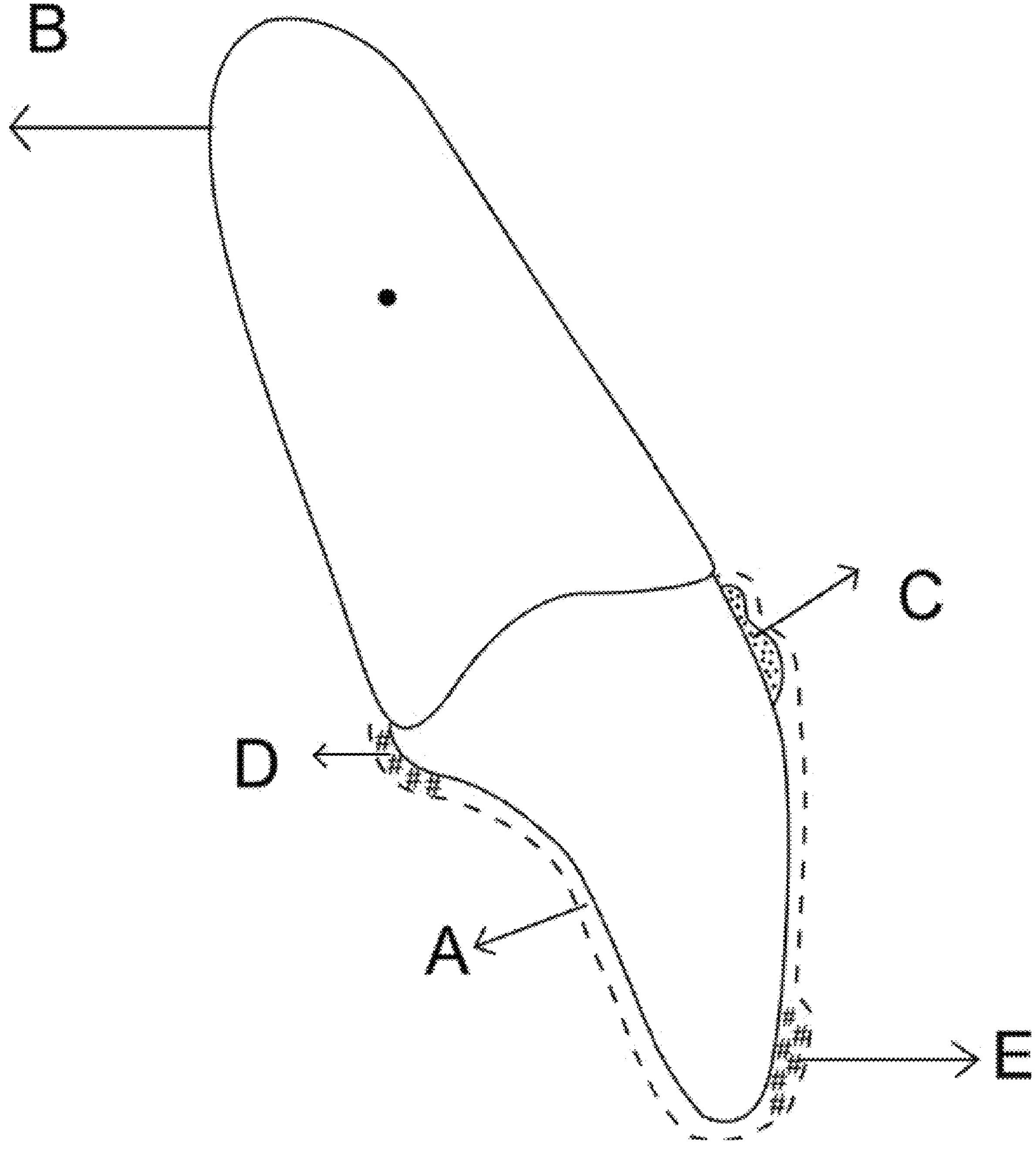
FIG. 32 is a diagram showing an example new design for torqueing anterior teeth.

In an implementation, a proposed improvement creates a better engagement of the example aligner at the point of force application by making the aligner engage into the divot anchor on the buccal side towards the gingival margin, while creating spaces on the opposite side to reduce resistance. This scenario is shown in FIG. 32, in which A is an example aligner, B is the intended direction of force, C is an example divot anchor for definitive engagement of the example aligner, D is a spacer to reduce resistance, and E is a soft material to allow controlled reciprocal movement of the crown. To enhance controlled movement of the crown, soft material may be added on the incisal one-third of the crown on the labial side.

Figure 33:
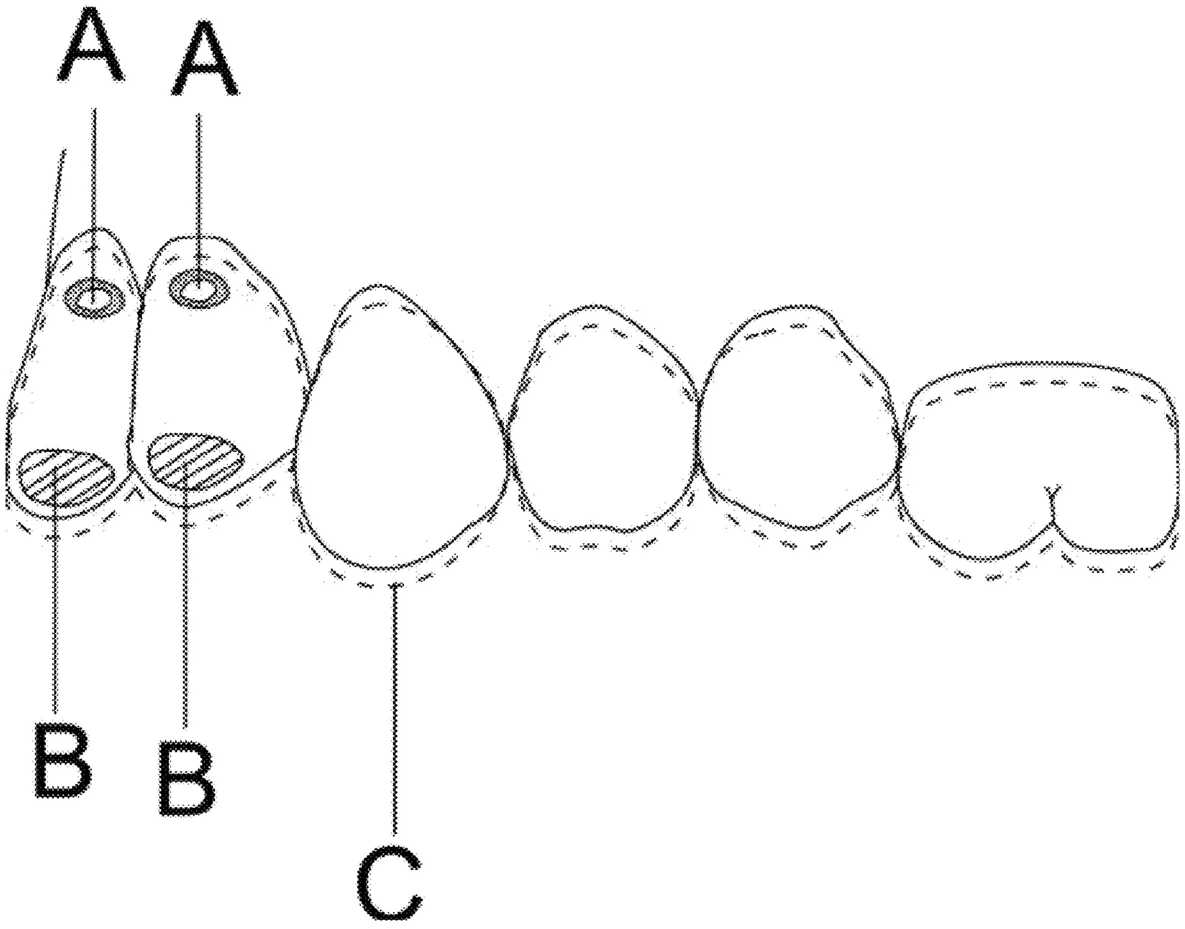
FIG. 33 is a diagram showing a buccal view of an example torqueing mechanism.

FIG. 33 is a buccal view of an example torqueing mechanism showing A as the example divot anchor and B as the soft reline to allow reciprocal crown movement.

Figure 34:
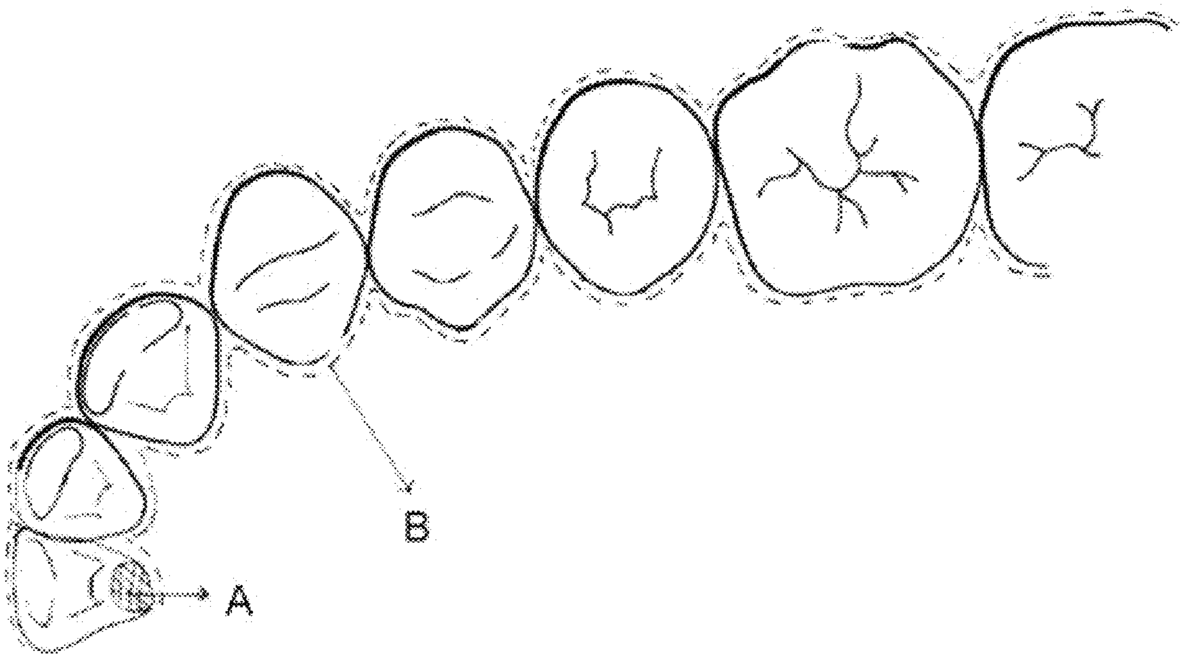
FIG. 34 is a diagram showing an occlusal view of an example torqueing mechanism.

FIG. 34 is an occlusal view of an example torqueing system showing the torqueing mechanism and space at the level of the cingilum of the center incisor. Spacer A reduces resistance for palatal movement of the cervical part of crown, and B is an aligner.

Figure 35:
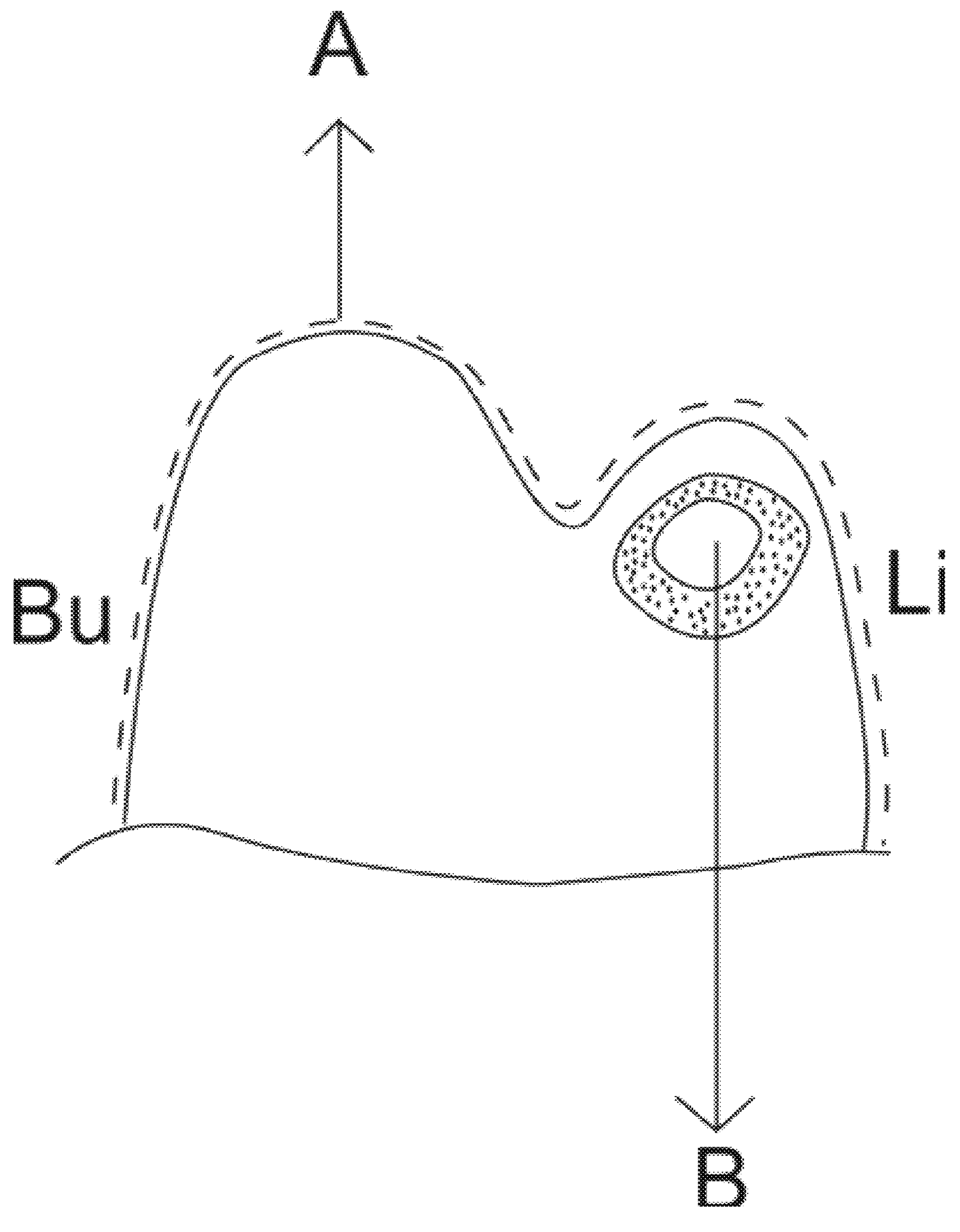
FIG. 35 is a diagram showing a mesial view of example rotation mechanics.

FIG. 35 shows a mesial view of rotation mechanics showing the example divot anchor and its approximate placement on the buccal side to cause mesiolingual rotation. Here, A is the example aligner, and B is the example divot anchor. Bu represents the buccal surface, while Li represents the lingual surface.

Figure 36:
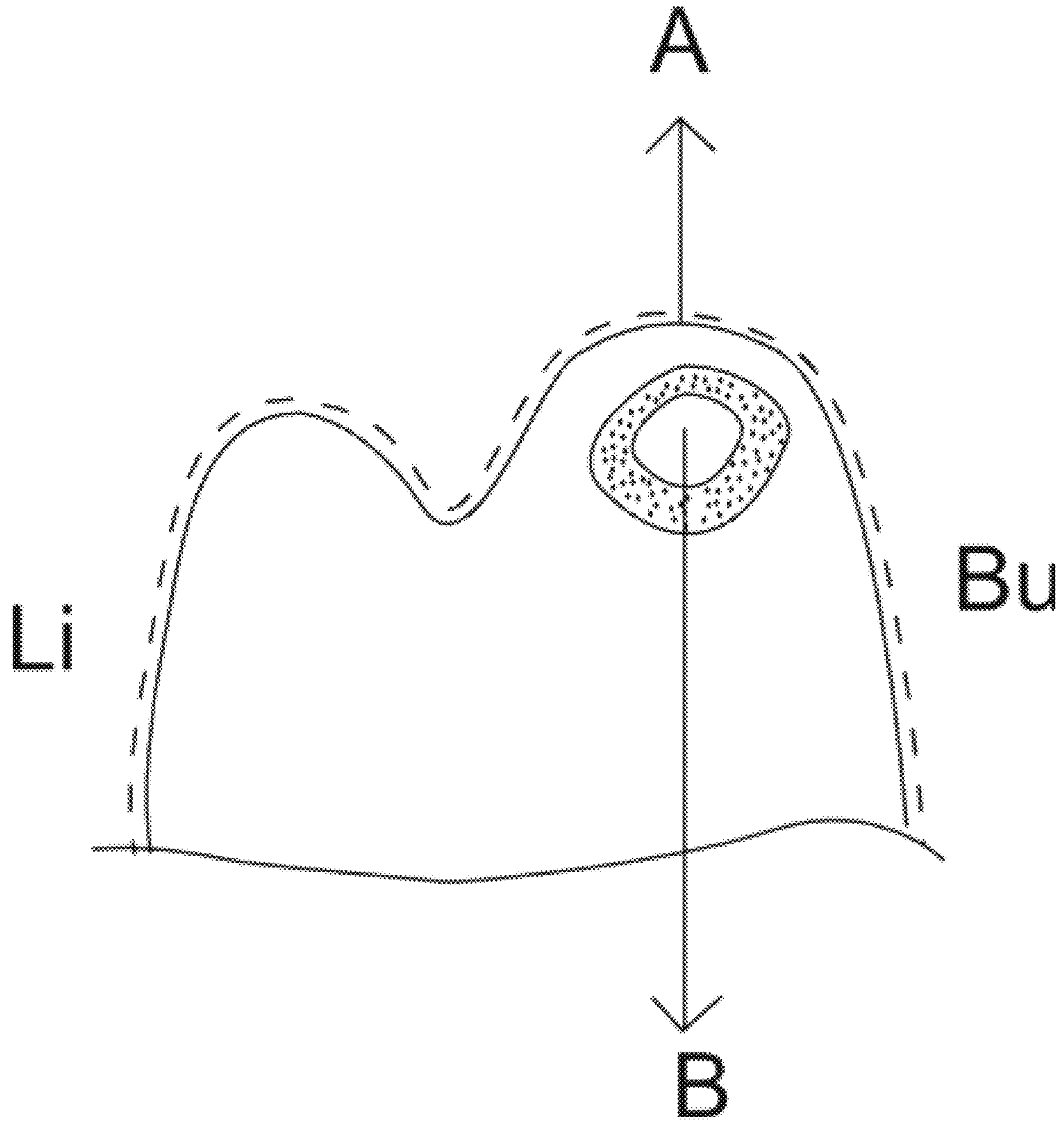
FIG. 36 is a diagram showing a distal view of example rotation mechanics.

FIG. 36 is a distal view of rotation mechanics showing approximate placement of a divot anchor attachment on the lingual side to cause mesiolingual rotation. Here, A is the example aligner, and B is the example divot anchor. Bu represents the buccal surface, while Li represents the lingual surface.

In an implementation, an orthodontic system includes an aligner for fitting over one or more teeth to apply a force to at least one tooth, and at least one 3D-printed part of the aligner for applying the force to the at least one tooth. The at least one 3D-printed part may comprise a 3D-printed material capable of an elastic strain recovery for applying the force to the at least one tooth. The at least one 3D-printed part applies a torque, a rotational force, a leverage, a push, a pull, or at least part of a full 3D control force to the at least one tooth.

A divot anchor can independently attach to a tooth, wherein a geometry or an extension of the 3D-printed part of the aligner is configured to form a removable attachment with a divot of the divot anchor to apply a torque, a rotational force, a leverage, a push, a pull, or at least part of a full 3D control force to the tooth through the divot anchor.

Multiple divot anchors may each independently attach to a tooth, and the aligner applies a different force vector to the tooth through each of the multiple divot anchors.

The divot anchor may further comprise a groove, a channel, a notch, a depression, a cavity, or a hole for securing a tab, a flange, a rib, a hook, an extension, a geometry, or a member of the aligner for applying a force to the tooth, wherein the force comprises one of a torque, a rotational force, a leverage, a push, a pull, or at least part of a full 3D control force.

At least one 3D-printed part of the aligner may be constructed in an additive manufacturing process.

The system may further comprise a torque control feature of the aligner, the torque control feature comprising a space disposed between the aligner and at least one tooth. A compressible material may be disposed in the space between the aligner and the at least one tooth. The aligner may comprise a plurality of materials each having a different modulus of elasticity. The aligner may comprise a first material with a first modulus of elasticity for front teeth and a second material with a second modulus of elasticity for back teeth.

At least part of the aligner may be constructed in an additive manufacturing processes selected from the group consisting of a FDM process, a SLS process, a direct pellets fused deposition process, a SLA process or a DLP process, a multi-jet photo cured polymer process, a multi jet fusion technology, and a CLIP process.

An additive may be used that fades over a time interval upon contact with mouth fluids.

A microchip and a sensor may be included in the aligner to detect a tooth movement over a time interval or to measure a compliance level of a patient.

The aligner may comprise multiple thicknesses of a 3D-printed material. A pigment or a coloring agent may be included in the aligner, formulated to match a color of teeth. A polymeric coating may be placed on the aligner to reduce a surface porosity and to increase a surface smoothness of the aligner.

At least one 3D-printed part of the aligner may be composed of a material having a hardness on a Shore D scale in a range of 30-90, an elasticity modulus in a range of 1000-1800 Mpa, a tensile strength at yield in a range of 40-70 Mpa (ASTM 638-2010), Tensile Modulus in the range of 1400 Mpa to 2000 Mpa (ASTM D638), a percentage elongation at break in a range of 10-200%, Flexural strength—50-80 MPa ASTM D790, Flexural Modulus—1200-1900 MPa (ASTM D790), a percentage tear strength in a range of 45-60 MPa, Energy to break—10-20 Joules, no deformation in a range of 0.5% strain over a 8-24 hour period, a stress relaxation rate (N/s) in a range of 0.010-0.020, and a notch impact resistance at 23° C. of 10-30 kJ/m2 (ASTM D256 Test method FIG. 37 is a flow diagram of an example process 3700 for direct fabrication of 3D-printed orthodontic aligners for orthodontically correcting the position of teeth.

In a modeling block 3702, virtual models are created for the orthodontia to be performed, resulting in the 3D-printing of various sets of 3D aligners that will apply forces to the teeth, in stages that are also determined by the models. The 3D-printed aligners to be fabricated and used on a patient may also progress across a variety of materials to vary the magnitude of forces applied to the teeth.

In the modeling block 3702, a first virtual model of the teeth of a patient is produced. The first virtual model captures the patient's initial dental positions, either before orthodontia begins, for example, or from another selected starting point during orthodontia. In other words, the first virtual model represents the patient's malocclusion.

Next, virtual divot anchors are placed on the virtual teeth in the first virtual model, based on desired tooth movements.

Next, a second virtual model of orthodontic teeth movement is generated, based on the first virtual model. The second virtual model generates virtual movements of the patient's teeth, and may generate multiple stages in which the modeled tooth movements are to occur. The number of stages for applying the orthodontia may be based on the Modulus of Elasticity (MOE) of various materials for multiple aligners to be staged on the patient's teeth, a set of aligners providing tooth movement in a range of 0.3 mm-0.5 mm, for example.

Next, a third virtual model simulates and represents the various forces and vectors involved with the modeled tooth movements inputted from the second virtual model.

The modeling of block 3702 uses data collection from the patient for treatment, and may include the following steps:

1. Attain digital scan of the teeth or make physical models and scan the physical models of teeth or scan PVS impression of teeth.
2. Analyze virtual models for space discrepancy and protrusion of teeth.
3. Plan a case for treatment based on space requirements (e.g., whether or not to remove some teeth for space).
4. Based on anticipated directionality of tooth movement, virtually place divot anchors on teeth as needed.
5. From initial malocclusion position, with virtual divot anchors placed make transfer tray for the doctor based on the type of teeth movements desired, place divot anchors on teeth and acquire a scan.
6. Establish final position of teeth.
7. Establish steps and sequencing of correction (as too what movement of the teeth needs to be corrected first. such as rotation first, crowding next, and so forth) to attain changes from initial to final position of the teeth.
8. Establish staging to attain final position of teeth based on force needed to move teeth, this is based on the MOE (Modulus of Elasticity) of materials of the aligners and the amount of tooth movement to be performed. If force needed is 26 grams per $cm^2$ at root level and a movement ranging from 0.1-0.3 mm of tooth movement per aligner is needed, the MOE of materials and stress decay force hardening of aligner is established by finite element analysis (FEA).

Example Hardware Production and Patient Treatment

At block 3704, direct-fabrication of 3D-printed aligners is accomplished.

This includes, at block 3706, selecting among various specific 3D-printing technologies, based on aligner design and final desired positions for the teeth (orthodontic correction). At least part of an aligner is to fit over one or more teeth to apply at least part of the forces to at least one tooth (based on virtual model output).

At block 3708, one or more divot anchors are affixed to one or more teeth of the patient, according to a template made from the first virtual model before tooth movement, and then the direct-fabricated 3D-printed aligner is placed over the divot anchor(s) and over the teeth of the patient.

At block 3710, the 3D-printed aligner attaches to a divot of each divot anchor and applies a torque, a rotational force, a leverage, a push, a pull, or at least part of a full 3D control force to the tooth.

At block 3712, the desired final positions of the patient's teeth are achieved according to the staging of the virtual models, using several aligners based on the force needed to move the teeth.

Support Structures for 3D Printing Processes

When considering what technology to print thin complex design 3D aligner with, it is important to consider support structures and how they may affect the final result. Support structures have an impact on surface finish as they require post-processing work to remove, resulting in blemishes or surface roughness. It is most important to eliminate or minimize support structures for very thin aligners having very intricate complex designs.

Support Structures in FDM (Fused Deposition Molding):

With FDM 3D-printing of an aligner, each layer is printed as a set of heated filament threads which adhere to the threads below and around it. Each thread is printed slightly offset from its previous layer. This allows a model to be built up to angles of 45°, allowing prints to expand beyond its previous layer's width.

Figure 38:
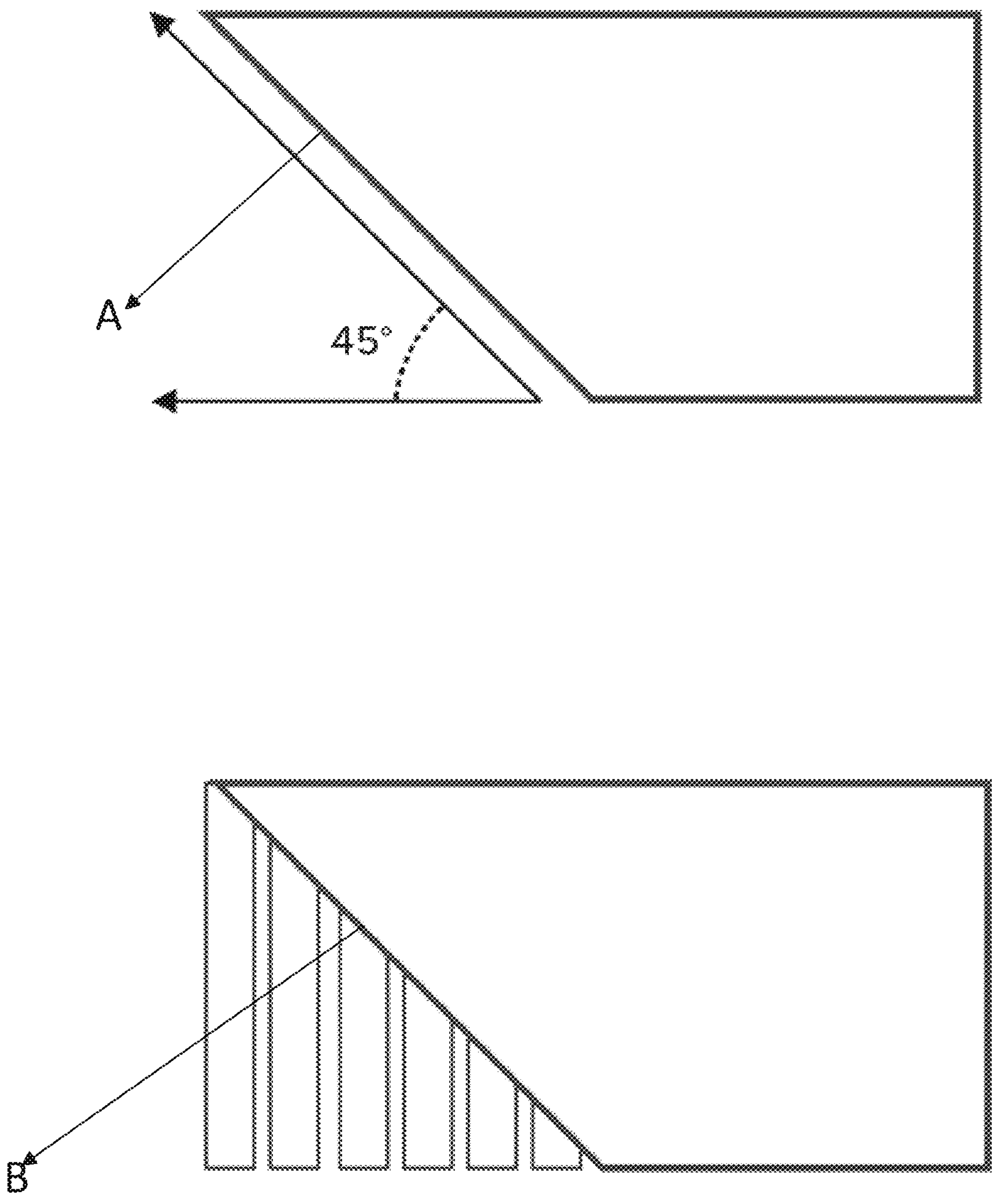
FIG. 38 is a diagram showing an example overhang angle during aligner construction relevant to support structures during 3D printing of the aligners.

As shown in FIG. 38, when a feature is printed with an overhang beyond 45°, the feature can sag and require support material to be underneath it to hold it up. In FIG. 38, "A" indicates that no support is needed if the overhang is less than a 45-degree angle. Label "B" indicates that a support structure is required for an aligner having overhang at greater than a 45-degree angle.

Figure 39:
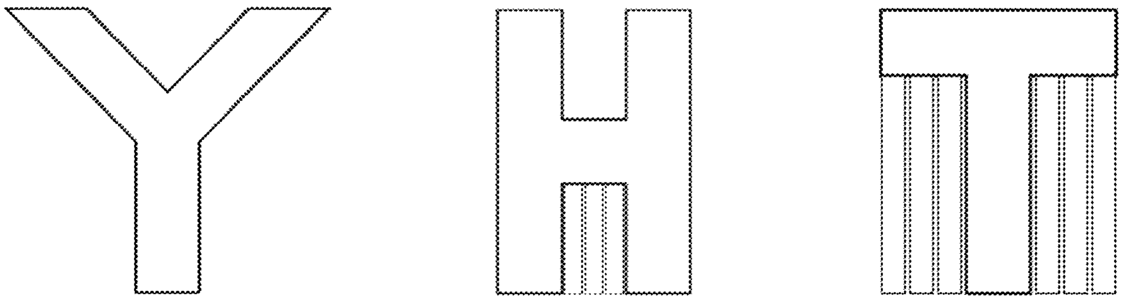
FIG. 39 is a diagram showing the different example designs of support structures.

FIG. 39 shows the arms of a model of the letter "Y," which can be printed easily. Even though the arms of the Y are outstretched, because they extend at 45 degrees or less, they do not require support. The letter H is a little more complicated but if the center bridge is under 5 mm, it can be printed without support or any sagging. A horizontal feature over 5 mm needs support, as when the center bridge of the letter H is over 5 mm. The letter T requires support for the arms of the letter. There is nothing for the outer arms of the T to be printed on, and the material will just fall down without support. These construction designs are considered when printing orthodontic aligners.

One of the limitations of using support in FDM 3D-printing is that post-processing is always required, resulting in marks or damage to the surface in contact with the support. Another issue is that layers printed upon support will be less perfect as the support will be slightly less stationary than the solid layers. Support can also be difficult to remove from small, intricate features without breaking the model. In an implementation, an example aligner uses support material that can be printed with a dissolvable material that does not tear away from the part but instead dissolves away in a chemical solution that does not affect the main material of the printed model. This can be a water- or solvent-soluble based support structure for 3D printing of the aligner. After the aligner with support structure is made, the support structure is easily removed by water jetting, or by keeping the aligner in water or solvent. This results in a better surface finish, when the support is in contact with the main material.

Figure 40:
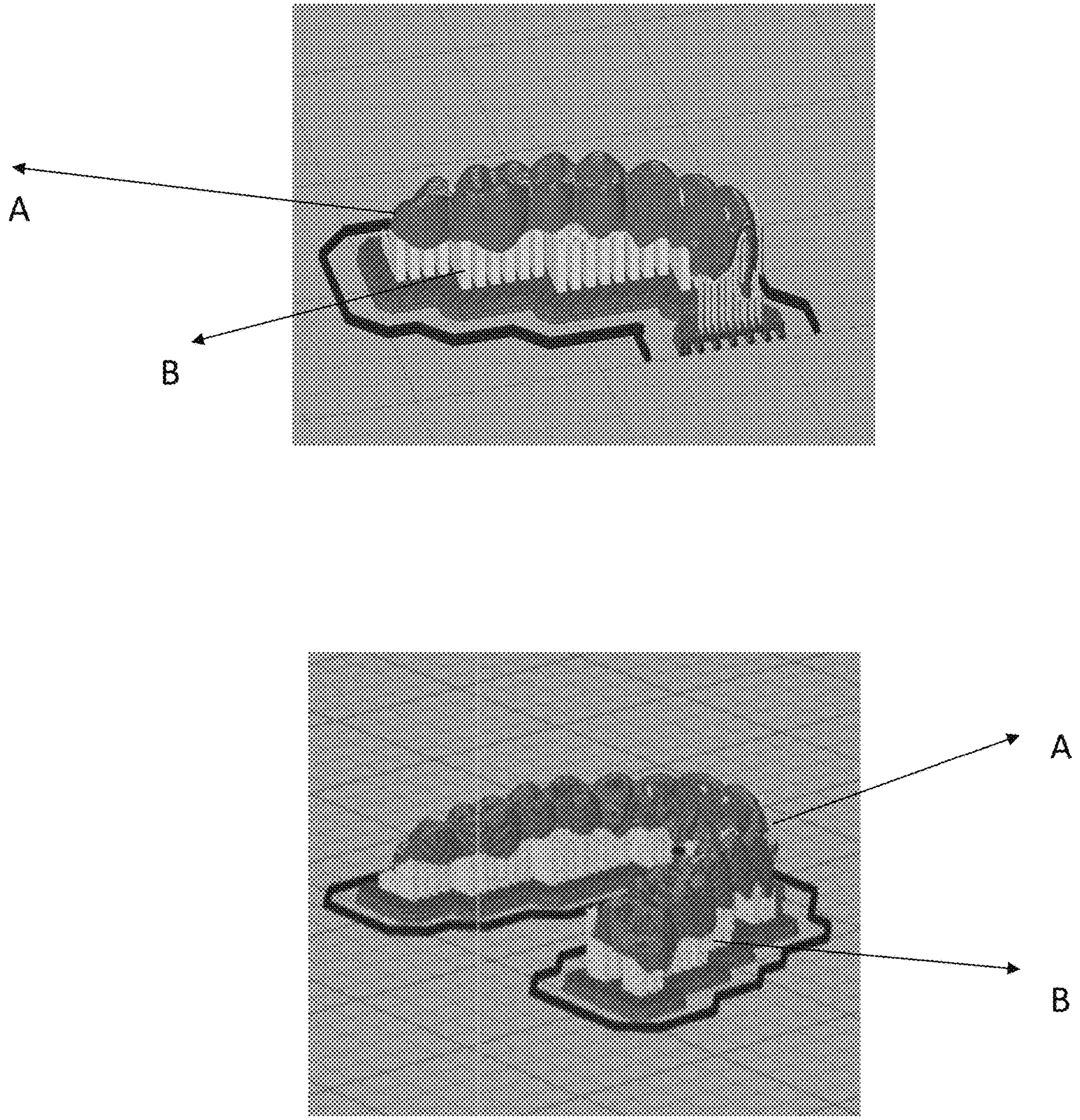
FIG. 40 is a diagram showing example support structures for an aligner produced by FDM 3D printing technologies with a support structure built inside the aligner.

FIG. 40 shows an example partially printed, and fully printed, FDM aligner with support structure. In FIG. 40, A is an aligner and B is a support structure. In an implementation, the support structures for a complex functional aligner are designed in such a manner that they do not touch the area of aligner touching the anchor areas, or the areas where the aligner has to perform movement of teeth. This positioning of support structures can be optimized by an example software algorithm for 3D-printing complex aligners.

Support Structures for SLA & DLP

Figure 41:
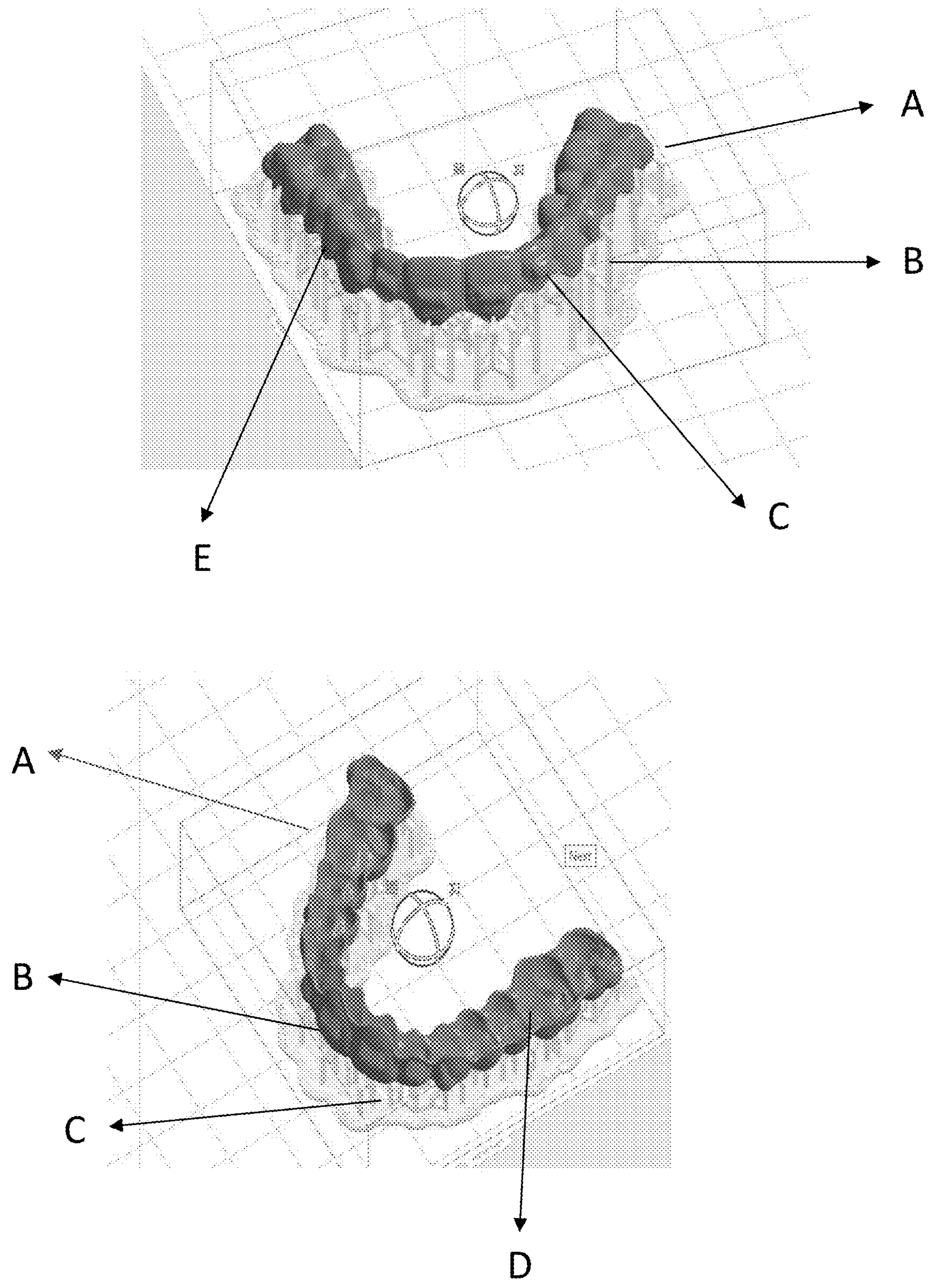
FIG. 41 is a diagram showing example support structures for an example aligner produced by resin-liquid photopolymer-based 3D printing technologies.

To make sure that the prints adhere to the print platform and do not float around in the vat, SLA and DLP printers require the use of supports in almost all cases. Support structures from these printers look like thin ribs, with only small tips actually touching the model to save material and printing time, as shown in FIG. 41. In FIG. 41, A is an aligner, B is a support structure while C is outside surface of aligner and D is inside surface of aligner. The number of supports, their location, where they touch the aligner and the structure is calculated by example algorithm and is dependent on the shape, orientation, and weight of the part being printed. SLA and DLP are some of the most accurate technologies, capable of printing even the smallest and most intricate objects with accurate detail. With proper post-processing, the usage of supports does not impact the quality of the print.

Removing support material from SLA & DLP aligners is required some work. First, isopropyl alcohol (IPA) is used to wash liquid resin off the completed aligners. Support structures can be either broken off the surface of the aligners or removed using pliers. The spots where the support was in contact with the object are then sanded to remove any remaining marks. Part orientation plays a crucial role on where support is located for SLA and DLP printing. By reorienting an aligner during printing, the amount of support (and therefore the cost of the aligner) can be drastically reduced. Orientation also plays an important role in where support will be located. If the aesthetic appearance of a surface on a component is paramount, orientating the part so that there is little to no support in contact with that area is also an option.

FIG. 41 shows the aligners made by SLA (resin system) with support structures. The left side shows outside support structure while the right side shows inside support structure. The support structures for aligner are designed such a way that they do not touch the area of the aligner touching the anchor area or areas where aligner has to perform a movement function. This is done by using aligner 3D-printing software.

In FIG. 41, the orthodontic system uses a rectangular divot anchor attached to the tooth. This rectangular attachment is of specific dimensions. A rectangular projection from the 3D-printed aligner fits into the groove of this rectangular attachment applying force in three dimensions to cause teeth to move incrementally with each change of aligner to the predetermined final position. Force is applied to the teeth by changing aligners in a timely manner. The process may start with a soft first aligner and increase in stiffness in subsequent aligners as needed as the treatment progresses. The number of aligners with different designs is based on the starting position of the teeth and the final desired position of the teeth.

Figure 42:
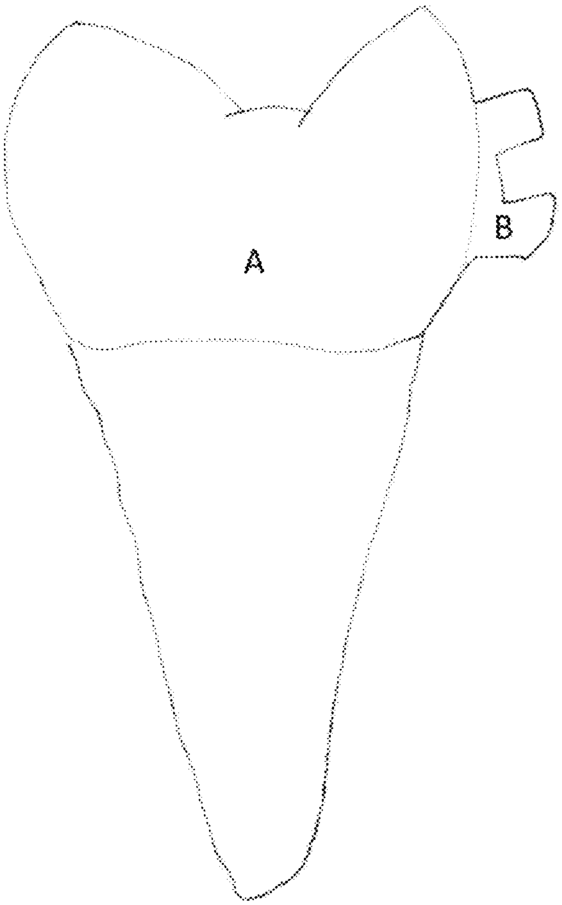
FIG. 42 is a diagram showing a tooth with an example rectangular projection.

FIG. 42 shows a tooth A that has a rectangular attachment B. In an implementation, the dimensions of the rectangular attachment are 0.081×0.071 cm, or 0.81×0.71 mm.

Figure 43:
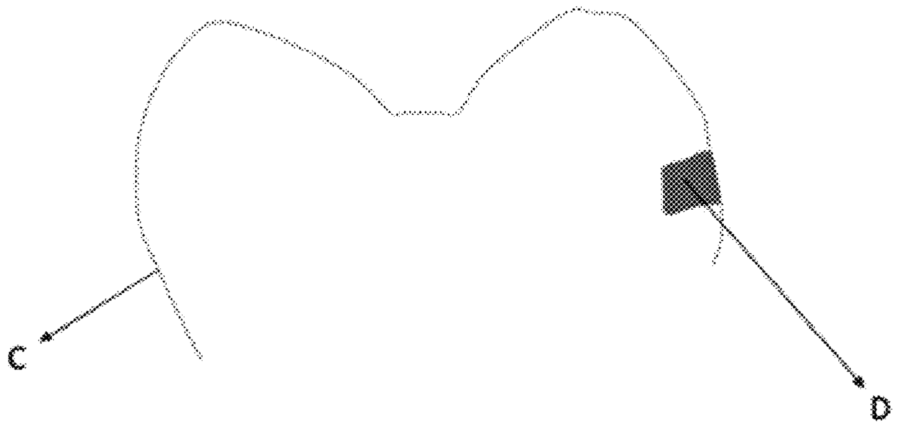
FIG. 43 is a diagram showing an aligner with the rectangular projection.

FIG. 43 shows a cross-sectional view of part of an aligner C over a tooth (not shown). D is a rectangular projection that will fit into a corresponding groove in a divot anchor secured to the tooth (see next figure).

Figure 44:
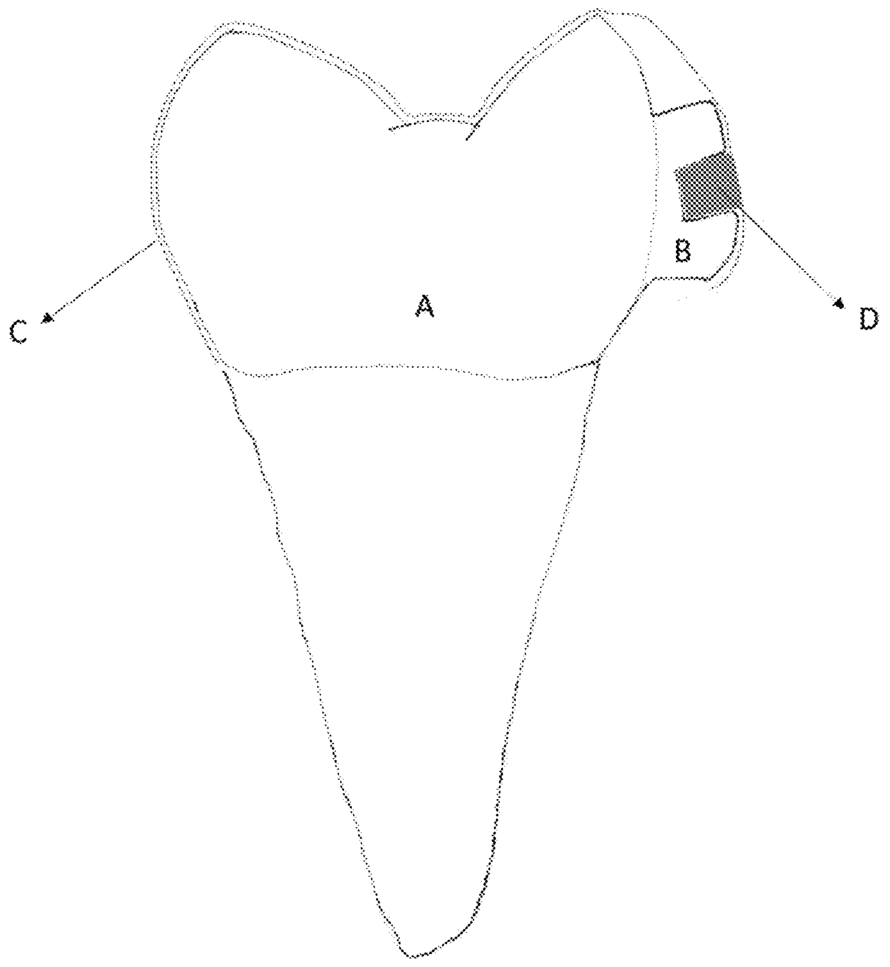
FIG. 44 is a diagram showing a tooth with an example rectangular attachment and rectangular projection from an aligner fitting into a rectangular channel of the rectangular attachment.

FIG. 44 shows a tooth A with rectangular divot attachment B, and aligner C with rectangular projection D fitting into rectangular channel of the rectangular divot attachment B.

The rectangular divot attachment B provides three-dimensional control of the teeth in terms of getting the tooth to a predetermined corrected position. Force is applied from the 3D-printed aligner C that is used over the attachments B. The example 3D-printed aligners fit over the teeth and have a horizontal rectangular projection D that fits into the groove or the rectangular channel of the rectangular divot attachment B, which delivers the necessary forces to move teeth to predetermined positions. It is important to ensure a complete fit of the rectangular projection D into the grove or channel of the attachment B to attain the desired teeth movements.

To attain final teeth positions, the aligners C are changed every so often (between one to two weeks). This is done in a progressive manner with the first aligner C being soft with force exerted as a 0.014 nitinol and each getting stiffer until the aligner strength reaches 0.018×0.025 stainless steel wire.

Figure 45:
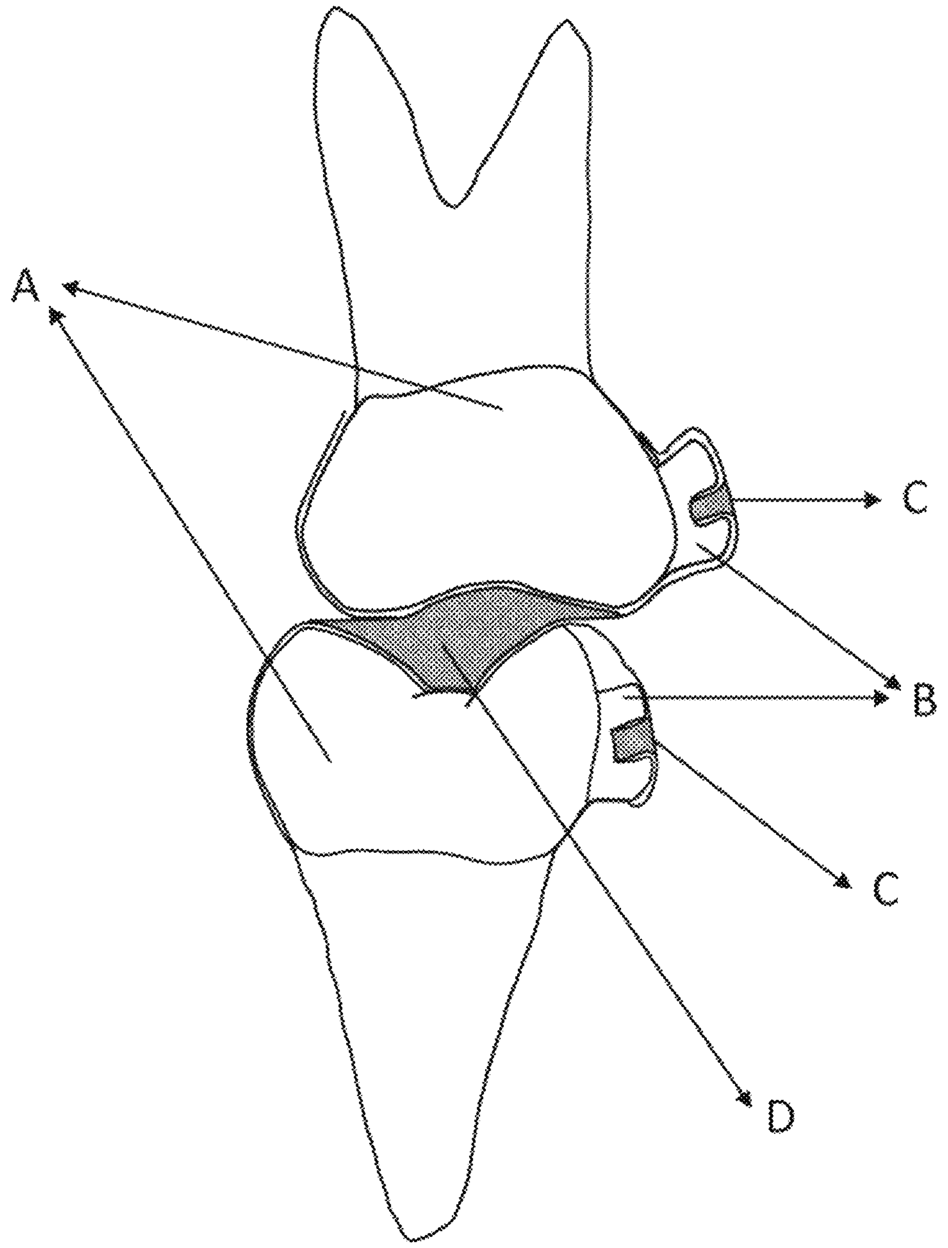
FIG. 45 is a diagram showing example flat occlusal surfaces of both upper and lower aligners.

FIG. 45 shows an example implementation in which the occlusal surface (biting surface) of both upper and lower 3D-printed aligners are made flat in between teeth, in addition to the above scheme for teeth correction through rectangular divot attachments B. The additional flat surface added to the aligner C can change the amount of force delivered. The forces can be controlled by altering the stiffness of the 3D-printed material used to make a given aligner. In FIG. 45, "A" represents the upper and lower teeth, B represents example rectangular attachments, C represents the horizontal projections of the aligners C engaging into the grooves of the rectangular attachments B, and D represents the flat biting surfaces of upper and lower aligners C (note that the aligners are not connected).

The example flat biting surface D of the 3D-printed aligners C enables several new ways of correcting the bite, correcting teeth positions, and reducing temporomandibular joint disorder (TMD) at the same time.

Bite Correction while Correcting Teeth Position

Figure 46:
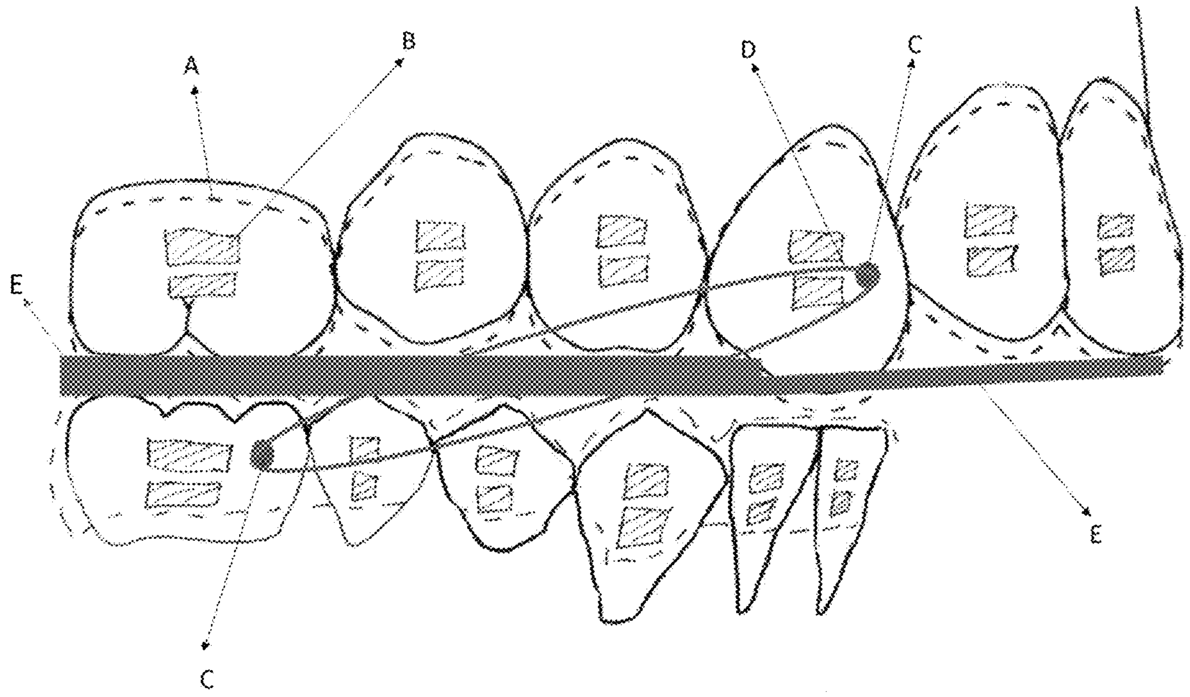
FIG. 46 is a diagram showing an example aligner for bite correction, with flat biting surfaces.

FIG. 46 shows example flat surfaces E of both upper and lower 3D-printed aligners A providing an advantage of separating teeth interference, and with the help of 3D-printed elastics hooks C (incorporated into the 3D-printed aligners), directional elastics can be used in Class II (lower back upper front) or Class III (in the opposite direction as class II) to correct bite, while still simultaneously accomplishing individual tooth movements. In FIG. 46, B is a rectangular divot attachment, C represents elastics hooks, D represents elastics, and E represents flat surface plastics between the aligners A.

Occlusal Orthotic or Bite Splint to Treat Temporomandibular Disorder (TMD)

Figure 47:
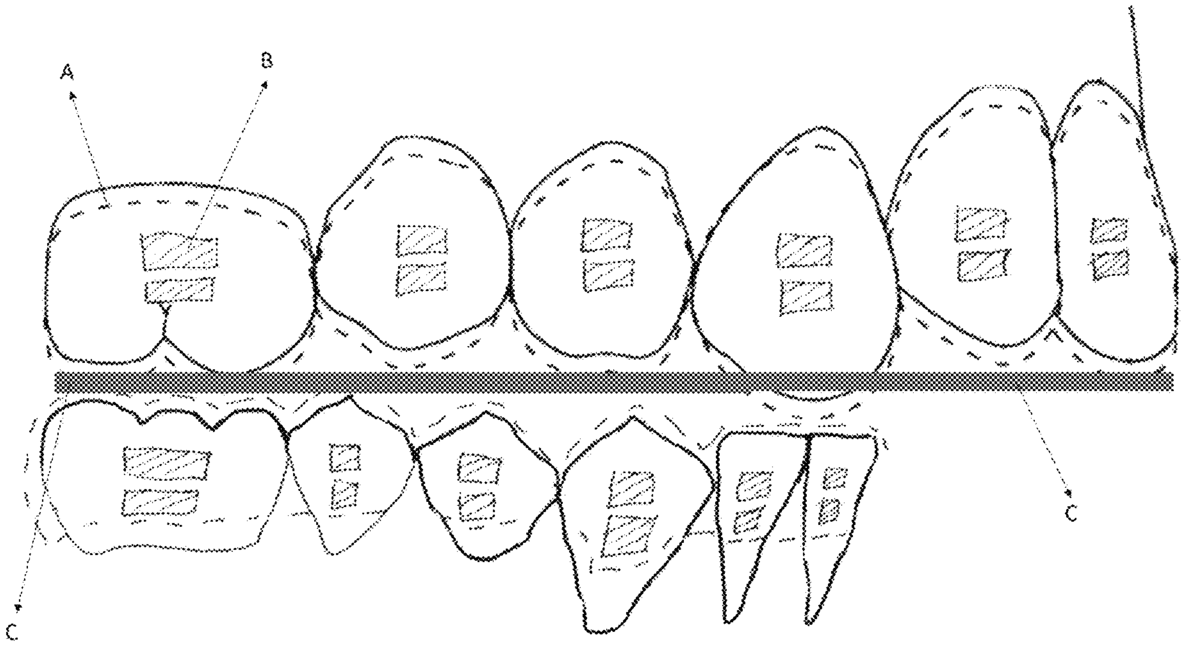
FIG. 47 is a diagram showing an example occlusal orthotic or bite splint/aligner.

FIG. 47 shows the example flat surface C of a 3D-printed aligner A allowing the upper and lower aligners A to be used as a bite splint to treat temporomandibular joint disorder (TMD) with proper customization of occlusal or tooth contact between the upper and lower arches. This TMD treatment can be accomplished in conjunction with moving teeth. In FIG. 47, A is the aligner over tooth, B is a rectangular divot attachment, and C is the flat biting surface of the upper and lower aligners A. The flat surface C may be possible only with 3D-printed aligners, and has a great advantage over conventional systems, in which orthodontic treatment needs to be interrupted during stabilization of the temporomandibular joint problem (TMD). The TMD treatment is achieved by custom adjustments of the interposition flat piece C, which can be made as an additional or auxiliary appliance kept in position by securing with a vertical channel of either upper or lower, single or multiple divot attachments, as the lower jaw can be moved into a ligament-dictated relaxed position.

Functional Appliance (Jaw Growth Promoting Appliance)

Figure 48:
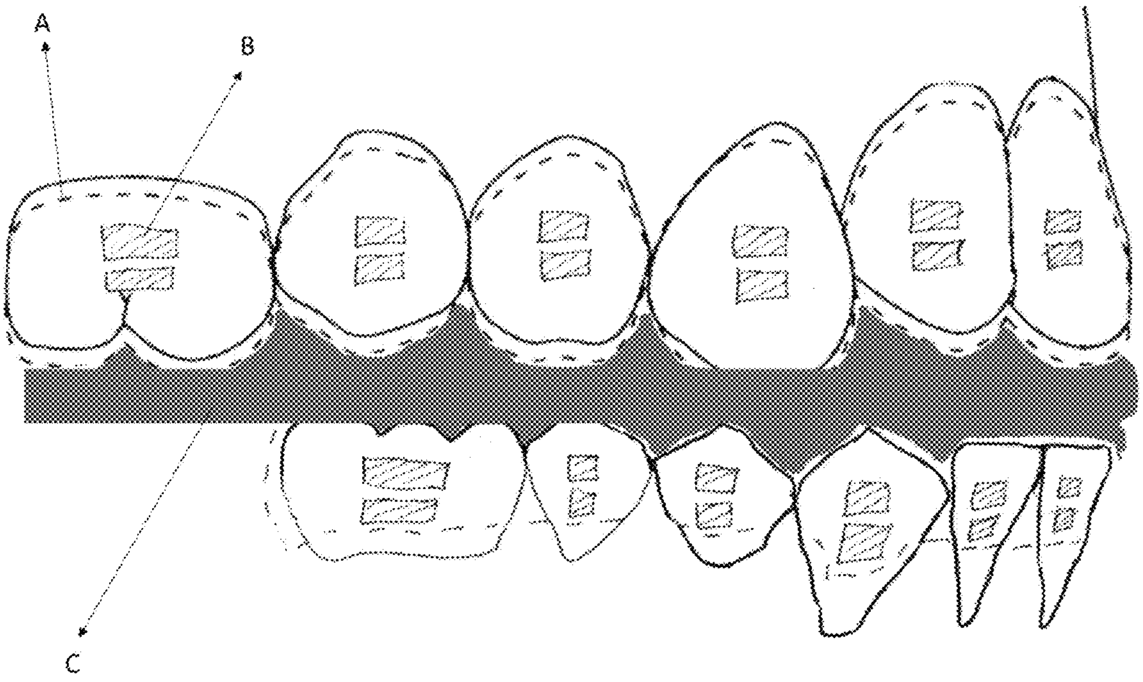
FIG. 48 is a diagram showing an example 3D-printed aligner and functional appliance for jaw growth.

FIG. 48 shows an example 3D-printed aligner A correcting both tooth positions as well as acting as a functional appliance (a jaw growth promoting appliance). In FIG. 48, A is an aligner and is B a rectangular attachment. If the 3D-printed aligners with indentations are used to posture the jaw forward all of the time except while eating, then the aligner A can be used as a functional appliance to promote growth of the lower jaw, while simultaneously correcting positions of teeth. This functional feature can be realized by having directional indentation printed into the aligner A, in which case the post system needs to be adjusted by altering MOE or as an auxiliary appliance retained by a vertical slot of one or more divot attachments, in which case additional properties of additional aligners do not need to be changed. This system allows continuous movement of teeth while jaw growth is being promoted. The interposition flat piece with indentations can be made with different degrees of jaw advancement.

Aligners with Sleep Apnea Treatment—Dual Function Device

Obstructive sleep apnea (OSA) is a sleep disorder with partial or complete cessation of breathing during one's sleep. This sleep disorder is currently treated by methods such as a surgery, oral appliance therapy, negative pressure to pull soft palate and tongue forward, implantable devices that keep the airway open during sleep by stimulating the hypoglossal nerve, strips for the nose for expiratory positive airway pressure, Positive Air Pressure (PAP) therapy, or a combination involving several methods. PAP therapies are also employed to treat other medical and respiratory disorders, such as Cheynes-Stokes respiration, congestive heart failure, and stroke. A common PAP device comprises a flow generator (e.g., a blower) that delivers gas via delivery conduit (hollow tube) to an individual interface. It is also known to deliver the PAP as a continuous positive airway pressure (CPAP), a variable airway pressure, such as bi-level pressure (Bi-PAP) that varies with the individual's respiratory cycle or an auto-titrating pressure (APAP) that varies with the monitored condition of the individual. Nasal, oral-nasal, and full-face masks are common interfaces utilized for delivering PAP to the individual's airway.

These masks can be uncomfortable due to improper fit, tight straps to hold mask in place, skin irritation at points of contact, dryness of throat, the feelings of claustrophobia, and excessive PAP pressure are major factors in individual therapy non-compliance. Also, the PAP machines can be noisy. Studies show individual compliance for PAP therapy is less than 50%. For patients who cannot tolerate CPAP machine therapy, oral appliance therapy is an effective treatment option for snoring and obstructive sleep apnea (OSA). A custom-fit oral sleep appliance known as a mandibular advancement device (MAD), can be effective for people who cannot tolerate CPAP devices. Worn only during sleep, an MAD oral appliance fits like a sports mouth guard or an orthodontic retainer. It supports the jaw in a forward position to help maintain an open upper airway. The devices snap over the upper and lower dental arches and have several designs/concepts for the lower jaw to be eased forward. Some, devices allow patient to control the degree of advancement. But there is no device on the market for children as well as adults to treat sleep apnea while they going through the process of straightening teeth with aligners, except the combination of conventional aligners with conventional PAP devices, which is not a comfortable combination. Most importantly, treating both conditions is an advantage in preparation for definitive treatment with orthognathic surgery (jaw surgery).

Aligners/Sleep Apnea Device with Mandibular Advancement

Figure 49:
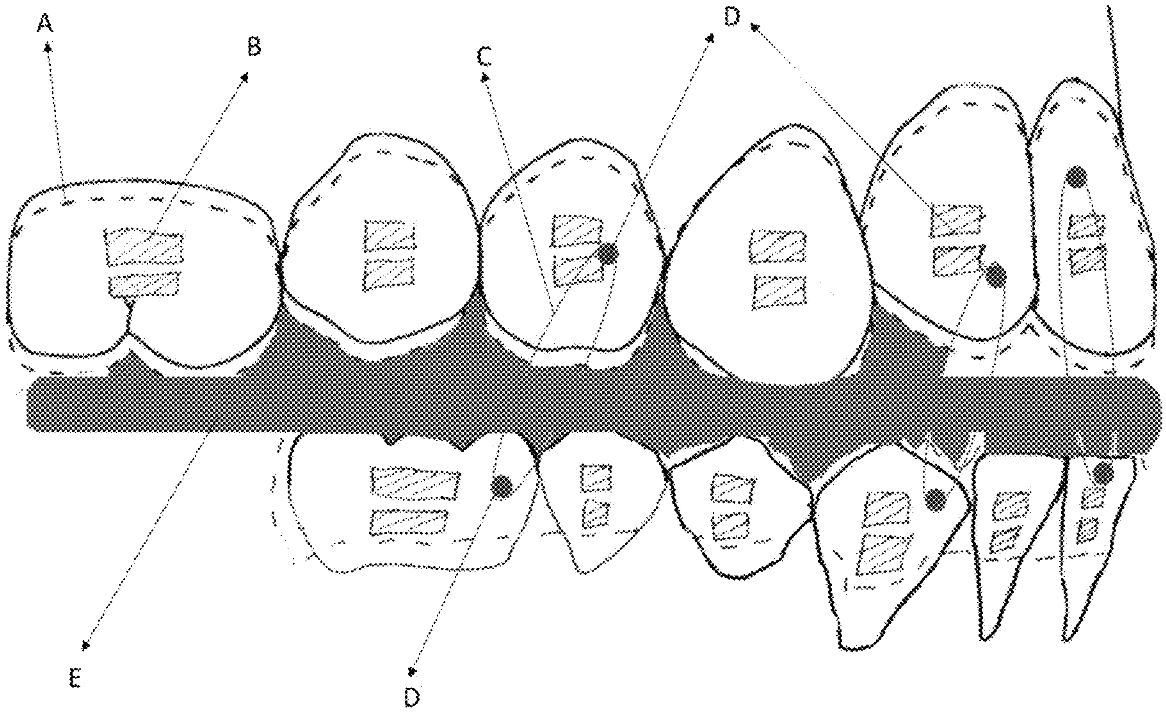
FIG. 49 is a diagram showing modified aligners with mandibular advancement features, to treat sleep apnea while correcting teeth.

FIG. 49 shows an example orthodontic aligner for a process of straightening teeth (correcting the teeth position) and simultaneously treating sleep apnea using daytime aligners and nighttime aligners (for example, a modified same daytime aligner for night) to bring the lower jaw forward, and to maintain an open upper airway during sleep to treat sleep apnea or snoring. The purpose for modifying the same day time aligners for night time wear is so that the aligner's function or treatment is not affected. The daytime aligners have hooks, but elastic is not attached to move lower jaw forward. For nighttime use, elastics are attached to move the lower jaw forward. The functionality (design) of the aligner in correcting teeth positions continuously is the same for day and nighttime aligners, except that the nighttime aligner has the capability of treating sleep apnea or snoring by bringing lower jaw forward.

The hooks on the example aligner can be 3D-printed on the aligner (i.e., attached) in forward or backward positions of upper and lower 3D-printed aligners, as an attachment. The nighttime aligner allows the lower jaw to move forward, not only treating the sleep apnea (keeping the airway open), but also simultaneously and continuously correcting teeth position in the same manner as the daytime aligner. There are not separate day and nighttime aligners, elastic is just attached on hooks for the nighttime to bring the lower jaw forward. As shown in FIG. 49, if the plastics between the upper and lower 3D-printed aligners A are indented with plastics E plastic goes between teeth) to hold the jaw in a forward position and the jaw held forward is supported with the help of elastics C, attached to 3D-printed attachments D to hold elastic C on the aligner such that the jaw does not go back or the jaw does not open during sleep, then the system can be used as a sleep apnea appliance, while simultaneously correcting teeth positions. Either a push or pull system can be used with elastics for bringing the lower jaw forward. The length of elastic bands depends on how much distance the lower jaw is to be brought forward depending on the AHI index of the patient (severity of sleep apnea of the patient).

One can use the example sleep apnea orthodontic aligner with or without the flat plastic member attached to the aligner, if this is not part of the aligner, the flat plastic member can be made as an auxiliary appliance or additional appliance to fit between the upper and lower aligner anchored to the vertical slot of a single or multiple divot attachment. The plastics between the upper and lower 3D-printed aligners are indented (the plastic goes between teeth) to hold the jaw in a forward position, and the jaw held forward is supported with the help of elastics, and attached to 3D-printed attachments on the aligner such that the jaw does not go back and the jaw does not open during sleep. This system can be used as a sleep apnea appliance, while simultaneously correcting teeth positions. During daytime, if the plastic member is part of the aligner, then a different daytime aligner is needed. If the plastic member is an auxiliary appliance, then just removing the plastic member and discontinuing the elastic suffices during the daytime. This system allows continued teeth movement during the day and night uninterrupted.

Aligners/Sleep Apnea Device without Mandibular Advancement

Another example aligner treats sleep apnea and straightens teeth without moving the lower jaw forward. Here, as described below, "daytime aligners" and "nighttime aligners (modified daytime aligners)" are used by the patient. This is specifically very useful for children that have sleep apnea, as CPAP machine compliance level is very low due to low comfort level, need of constant face mask changes due to the growth of children in order to prevent air leakage, and conventional oral appliances to bring the jaw forward cannot be used for children wearing conventional aligners or conventional braces treatments. The example aligners can include several design modifications for not bringing the lower jaw forward.

Figure 50:
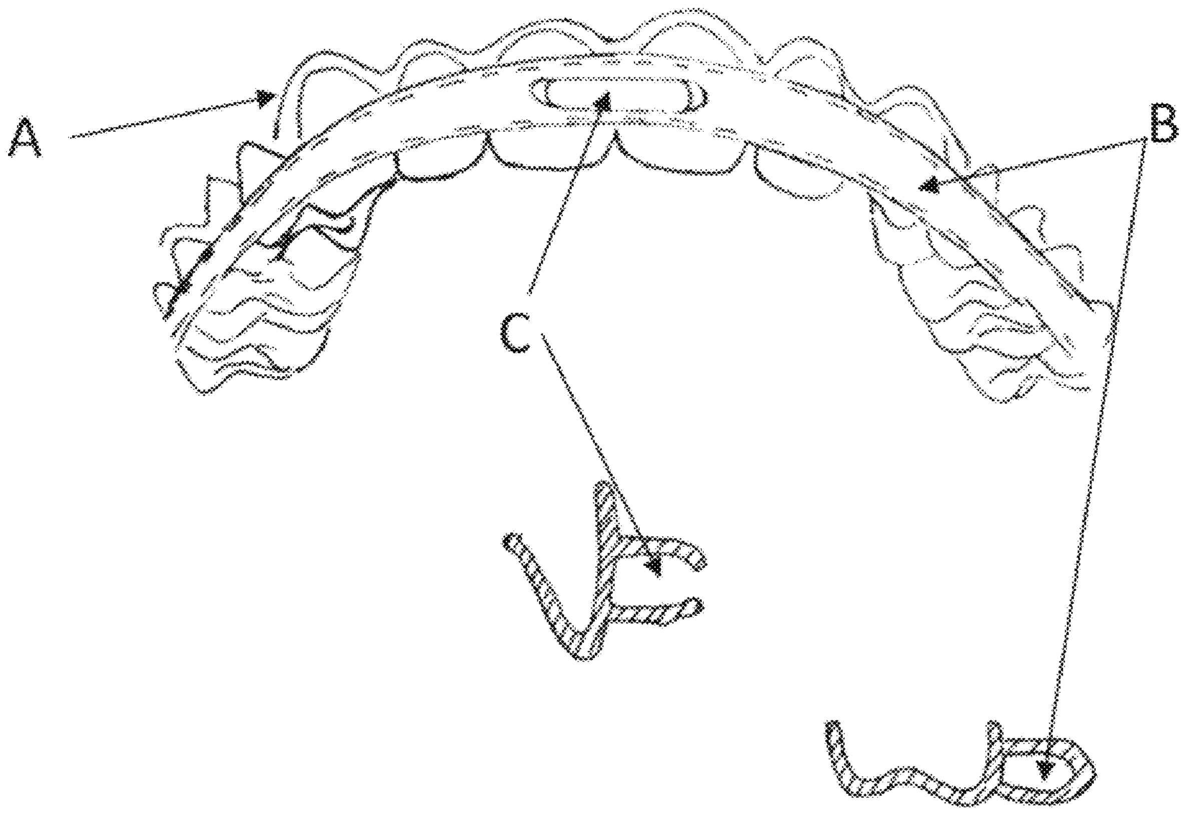
FIG. 50 is a diagram of an example aligner for day time, comprising a hollow tube.

FIG. 50 shows an example "daytime 3D-printed upper aligner" labeled "A," which has hollow tube B to the upper aligner. Only the upper aligner has the hollow tube B. In an implementation, the lower aligner is not 3D-printed or modified with a hollow tube. The hollow tube B can also be molded and bonded via several technologies to conventional Invisalign-type thermoformed clear aligner systems available in the market. The hollow tube B on the aligner A goes from front of the mouth area (lips area) to the back (throat area), to the oropharynx or laryngopharynx area. In the center position of the hollow tube B (center of lips area), there is an opening C in the daytime aligner. The opening C is in flush with the tube B such a way that it does not interfere with the patient's daytime activity such as talking, breathing, and the opening C also allows the patient's mouth to close completely and comfortably. If for any patient, there is a slight possibility of air coming in through opening C, then opening C can be closed by using a simple detachable snap-on lid. The daytime aligner functions normally as designed to straighten the teeth. In another scenario, the lower aligner can be modified instead of the upper aligner, with a hollow tube B. This example aligner system modifies only one aligner, either the upper or the lower aligner, with hollow tube B. Which aligner to be modified (upper or lower) can be defined by the patient's mouth and teeth geometry. The patient wears both the upper and lower aligners during the daytime to correct teeth positioning. In the daytime, when the patient is awake, no sleep apnea occurs.

Figure 51:
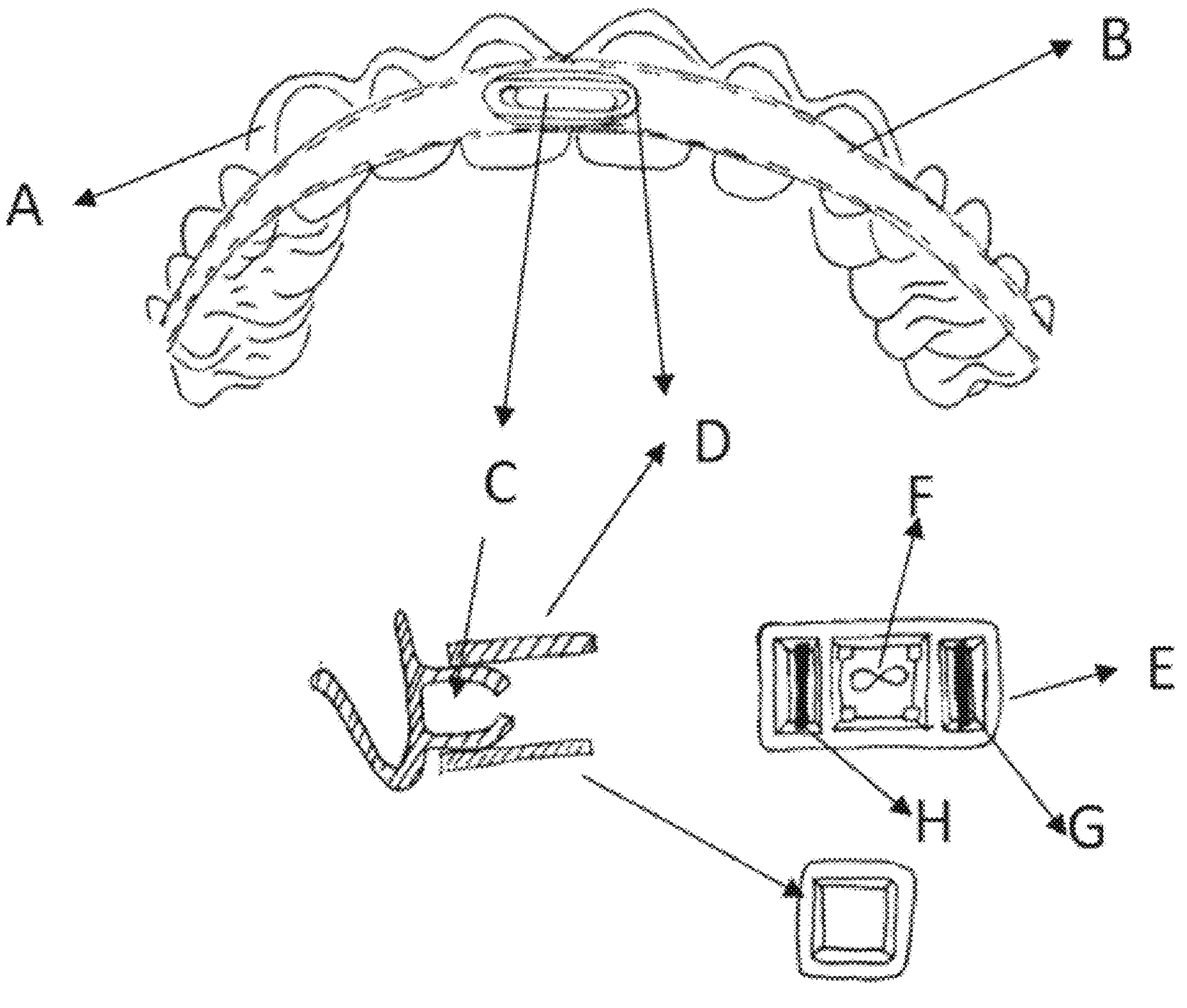
FIG. 51 is a diagram showing an example modified aligner of FIG. 50 as a single piece aligner/sleep apnea device with hollow front housing and micro blower, control module with microprocessor, Bluetooth, micro-SD card, several sensors, and rechargeable battery.

FIG. 51 shows the design of a "nighttime 3D-printed upper aligner" with a sleep apnea treatment device, without capability of moving the lower jaw forward as the lower aligner is worn "as is" during sleep. In this implementation, the same day time aligner shown in FIG. 50 is modified so that the patient attaches a detachable hollow housing D, snap-fit on the front center hollow opening C (center of lips area) of hollow tube B of the example aligner as shown in FIG. 51. This modified design with snap-fitted detachable front hollow housing D brings outside air through the hollow housing D as the patient breaths, to hollow center C and through hollow tubes B to the back of the mouth, bypassing the soft tissues, palates, tongue etc., directly to the oropharynx or laryngopharynx area, not allowing tongue to fall back and/or not allowing muscles along with soft fatty tissues in the upper mouth and throat areas to relax during sleep, thus keeping air passage open, and reducing or preventing sleep apnea and snoring. This example aligner system not only keeps the air passage opens during sleep, but simultaneously corrects teeth positioning during sleep without need of bringing the lower jaw forward. As shown in FIG. 51, the detachable snap-fit front housing D can be replaced with other innovative front devices, such as housing E, which is divided into three section of a hollow housing. The center of the housing E has micro-blower(s) F with very high RPM (up to 20,000 RPM) to bring air continuously from the front, to connection C, to hollow tubes B, and all the way back to the oropharynx or laryngopharynx area (throat area). The housing E has two side openings G and H as shown in FIG. 51. G is a rechargeable battery. H is a compact control module consist of PCB containing microprocessor, Bluetooth, and optional micro-SD card, and can also contain several sensors such as airflow sensor, pressure sensor, pulse oximeter (to measure the pulse rate and oxygen saturation), temperature sensor, accelerometer, tilt sensor and sound sensor.

A target air pressure and airflow is achieved to keep the patient's air passage open, to treat the sleep apnea (airflow is automatically adjusted continuously during sleep) by controlling the speed of micro blower(s). This automatic control of the micro blower's speed is achieved by utilizing feedback from the sensors and microprocessor having a closed loop feedback control system with control logic, using a compact control module with PCB "H" inserted inside the front hollow housing E in FIG. 51. The collected data also provides compliance for treating sleep apnea and for use of the aligner device itself, during sleep. The example device has the capability to record data within the system using a micro-SD card or to transfer data wirelessly using Bluetooth or cloud to permit live monitoring of the medical condition of the individual, and treatment compliance.

The functionality of the example aligner to straighten teeth during the night is not affected using the sleep apnea treatment modification of the aligner system, which does not require bringing the lower jaw forward.

Figure 52:
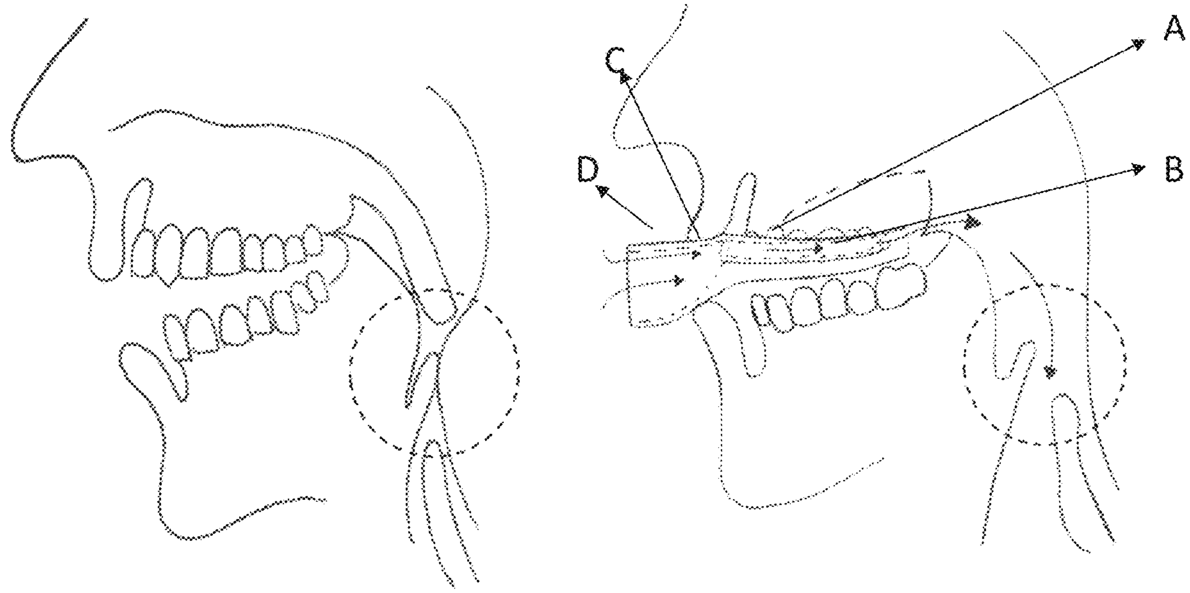
FIG. 52 is a diagram showing a patient wearing the example single piece aligner/sleep apnea device of FIG. 51 with front hollow housing attached to hollow tube of the aligner via detachable snap-fit structure.

FIG. 52 depicts the patient wearing the example aligner/sleep apnea device on upper teeth, using the devices of FIG. 51 with front hollow housing D attached to the hollow tube of B of the aligner A, via snap-fit structure C.

At least one 3D-printed part of an aligner may be made by fused deposit molding (FDM), an additive manufacturing process, containing monofilament where a soft, lower molecular weight material is disposed on the surface during 3D printing, or a dual filament has a core-shell structure in which the shell can be a soft material or a material with different crystallinity or different MOE than the non-shell.

Aligners/Sleep Apnea Device with Mandibular Advancement and Air Passage Through Front Hollow Housing and Tubes on Aligner An example aligner system includes an orthodontic aligner capable of providing sleep apnea treatment, which moves the lower jaw forward (FIG. 49) as well as a hollow tube on the aligner with a hollow front housing (FIGS. 50-51) to bring air from the front all the way to the back to the oropharynx or laryngopharynx areas (throat area) to keep the patient's air passage open during the sleep while correcting tooth malocclusion during sleep.

Dual Purpose Orthodontic Appliance Having Aligners to Straighten the Teeth or Teeth Trays to Prevent the Bruxism and to Treat Sleep Apnea Simultaneously with Smart Sensors and Control Module System In this embodiment, the purpose of dual-purpose appliance is described as simultaneously treating the Sleep Apnea and use of teeth trays for straightening the teeth (desired movement of teeth) or reducing the bruxism (teeth grinding) or reducing the TMJ. Going forwards, the teeth trays are defined as "aligners" or "bite splint" or "night guard" or "mouthguard". The appliance has smart sensors, control module, microprocessor, battery, wireless transmission, data storage, etc., which is described in different embodiments. Going forward "Control module System" is defined as module consists of microprocessor, PCB, memory storage, battery, wireless transmission, data storage and micro-blower when needed.

The dual-purpose orthodontic system has one or more 3D-printed parts of the 3D-printed aligner or teeth trays made from one or combinations of the several additive manufacturing methods.

I: Dual Purpose Appliances (Devices) without Detachable External Housing (No Micro-Blower, No Battery, No Microprocessor).

Figure 53:
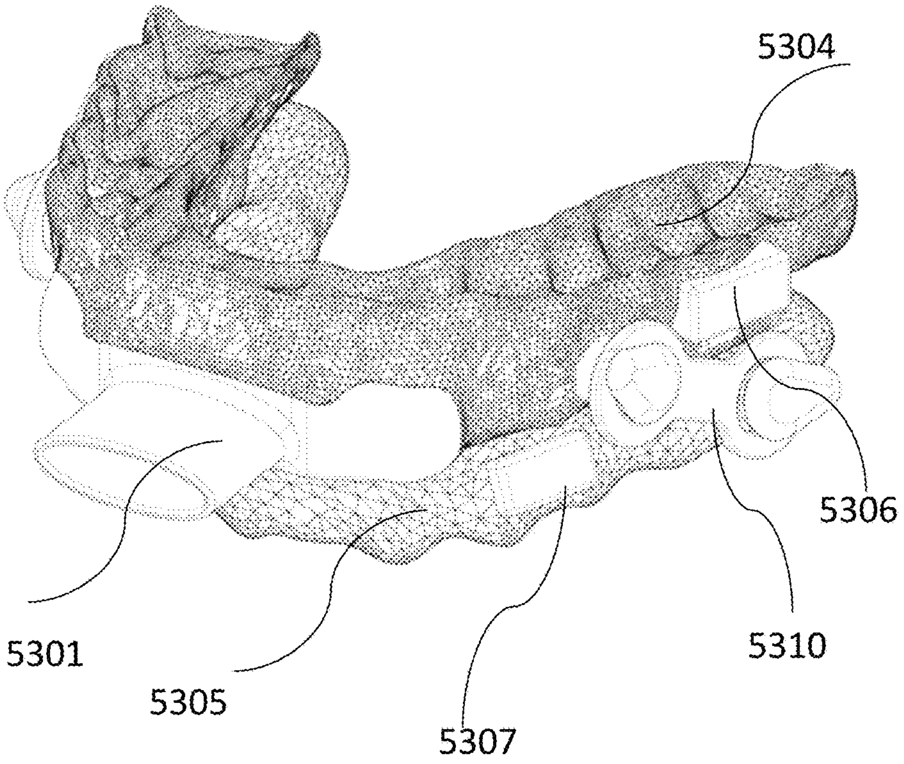
FIG. 53 is a diagram of an example dual-purpose orthodontic appliance showing a hollow air passageway of the teeth trays with a hollow opening starting from the lip area.
Figure 53:
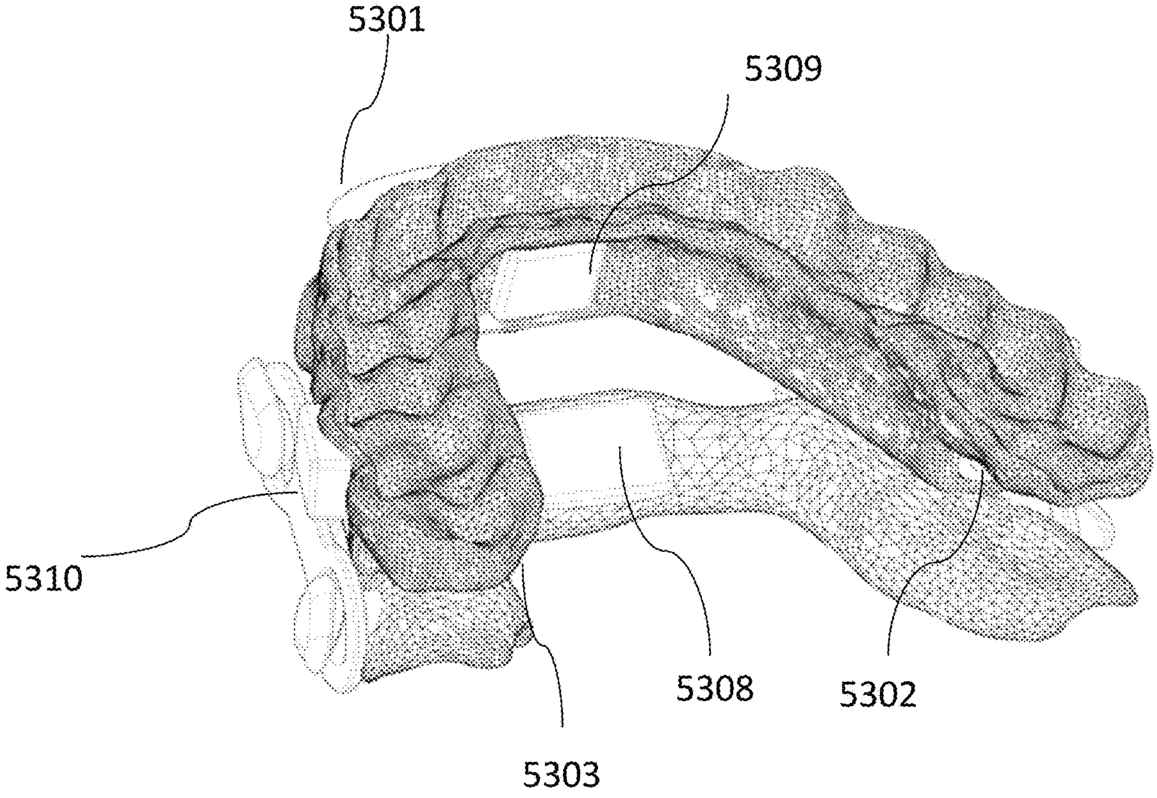

I-1. "Dual Purpose" MAD Appliance Having Smart Sensors and Hollow Passageway on Teeth Trays I-1A. Teeth Trays Having Hollow Oval Shape Tube (Air Passageways) Starting from the Outside of the Mouth and Surrounding the Teeth Trays In this embodiment, hollow air passageway of the teeth trays relates to hollow opening starting from the lip area. As shown in FIG. 18, where 5301 is oval shape hollow air passageway outside the mouth and in contact with lips for better fit. Air enters through 5301 hollow tubes during inhalation and exit at 5302 and 5303 bypassing the tongue. Here, the aligners or bite splints, or mouthguard or night-guard have air passageways with small hollow oval shape tube 5301 sticking out from the mouth for air inhalation and air bypassing the tongue and directed to throat area shown as 5302 and 5303 in FIG. 53. The upper teeth tray is shown as 5304 and lower teeth tray is shown as 5305. The linkage 5310 on both sides of the tray connects the upper and lower teeth trays and help in free movement of trays during the sleep. The size of the linkage determines how far lower jaw is moved.

In some embodiments, one of the several sensors and control module are mounted on the air passageway (hollow tubes) connected to the teeth trays. For example, 5306 sensor is mounted on the air passageway.

In some embodiments, one of the several sensors and control module are mounted on upper or lower the teeth trays or on both teeth trays. For example, 5307 control module is mounted on the lower teeth tray.

In some embodiments, one of the several sensors and control module are mounted on the air passageway and teeth trays. Here, control module system is shown at lower teeth tray 5308 but can be anywhere depending on the customized teeth trays design.

Types of smart sensors and their functions are described later on in sensors and communication section.

For Dual purpose MAD devise, the smart sensors and control module are used for several purposes. It is useful to allow the MAD and other sleep apnea treatment concepts respond in real time to the changes in the patient to provide the most effective mandibular position adjustment for the patient at the particular time. In addition, physicians would like to know the history of the changes in the patient's body while the MAD and other sleep apnea treatment concepts are being used in order to provide a better treatment regimen.

The first function of the Dual-Purpose appliance of the teeth trays is to align the teeth or reduce the bruxism (use of bite splint, nightguard etc.) as defined in previous CIP patent.

The second function of the teeth trays is to treat the sleep apnea with MAD device concept to reduce the sleep apnea along with several concepts, as described below I-1A-a Air Stimulation of Tongue and Toning of the Tongue with MAD In some embodiments, sleep apnea is reduced using two concepts. The first concept is use of MAD device concept (Mandibular advancement) where lower jaw is brought forward reducing the sleep apnea along with the air stimulation of tongue, meaning air is brought at the rear of the throat by-passing the tongue as shown at 5302 and 5303.

The device brings air in at atmospheric pressure during the inhalation at 5301 and the air moves from the front of the mouth to rear of the throat, completely bypassing the tongue. It stabilizes the lower jaw and tongue, keeping airways open and free from obstruction during sleep. The device has capability of air stimulation of tongue and soft tissues which may not allow soft tissues to relax, keeping air passageway in throat area open during the sleep.

In some embodiments, sleep apnea is reduced using combination concepts. The first concept is use of MAD device concept (Mandibular advancement) where lower jaw is brought forward using linkage 5310 reducing the sleep apnea along with the air stimulation of tongue using micro-holes in the hollow tubes 5302 and 5303 of air passageway of lower teeth tray. There can be continuous air flow (air-puff) through these micro holes which blows the air underneath or near the tongue the area where hypoglossal nerves and other soft tissues are located. Here, end of the tubes 5302 and 5303 are closed to create air velocity and pressure to stimulation tongue. The air comes out from these very small holes underneath the tongue area as "air puffs' slight air pressure, stimulating the to the lower part of the tongue's muscles and nerves, causing the tongue to return to its normal forward position, opening up the air passage in the oropharynx area, aiding reduction of episodes of sleep apnea.

I-1A-b Electric Stimulation of Tongue and Toning of the Tongue with MAD Device

Neuro/muscle stimulation of the Tongue or toning of the tongue is done by electric current using electrode or any other means of giving minor electric shock to tongue to keep tongue forward and/or bring it forward if retracted. One or a combination of sensors such as tongue touch sensor, position sensor or pressure sensors are used to find the normal position of tongue (tongue forward). For examples, these sensors are shown as 5309 and 5308. The length or numbers of position sensors are such that it should instantly recognize the tongue in forward position and when tongue retracts. This depends on mouth size as each patient's teeth trays have different size. These sensors are located on the upper or lower teeth tray to allow sensing of deviation of the tongue from its normal forward position. This data is fed into a control module with AI capabilities. During the sleep, when tongue retracts, the control module recognizes it and using AI algorithm, provides minor shock to the lower part of the tongue's muscles and nerves, causing the tongue to return to its normal forward position, opening up the air passage in the oropharynx area, aiding reduction of episodes of sleep apnea.

In one example, electrodes pass through the opening of the hollow air passageway surrounding the teeth tray. In other example, the electrodes are bonded to the teeth tray but not affected by the inner fluid of the mouth as electrode are coated with FDA approved adhesive.

In one of the embodiments of MAD or non-MAD device with air passageway connected to teeth tray, preferably to lower teeth tray, leads are attached nonsurgically underneath the tongue and electrodes are attached on the teeth tray, preferable lower teeth tray 5305. Here, the electric shock is given to hypoglossal nerve to keep the tongue forward in addition to air stimulation methods as described earlier.

For neurostimulation of tongue using minimal electric current, the dual-purpose appliance can be used without need of micro blower, eliminating a need of external detachable housing box.

For an example, the control module utilizes standard lithium-ion battery or solid-state battery when available and can adjust voltages from 1 to 3.7V and or up to 5V and provide pulsed current of 1 to 4 mA for 1-2 minutes. The amount of volt and amperage depends on number of apnea episodes patients have. In current embodiment, aim is to provide a pulsed current to the inside of the mouth in the proximity of the hypoglossal nerve and/or nerves/muscles of the tongue. The electric shock is applied only when tongue retracts to minimize the voltage and current requirements of the battery.

Electrodes can be sourced from current biomedically approved units currently available in the market. The electrode is attached to end of wire that can be passed through the hollow tube or bonded to the teeth trays which are not in contact of the teeth in close proximity to oropharynx area and in vicinity of the hypoglossal nerves.

One embodiment envisages a machine learning AI (Artificial Intelligent) system, that can learn episodes of tongue retraction due to signaling from brain to hypoglossal nerve and apply counteracting electric currents once a pattern is established.

In one of the embodiments, by using the safe electric current, which is applied continuously to stimulate and improve muscle function in the mouth and tongue (tone the tongue muscle). In effect, this gives tongue muscles a “work out” exercising them like any other muscle group, making them strong. If patient sleeps with device for few weeks, the tongue muscles will be strengthened and toned, will become strong and sleep apnea level will reduce significantly. Then, the patients may not have to use the appliance for few months till HST (home sleep testing) shows that AHI index (sleep apnea level) has increased again. The patient will again sleep with appliance for few weeks followed by no wearing of appliance for few months. Eventually, sleep apnea level can be significantly reduced to a level that patient may not need to use appliance for few months as tongue muscles will be strong enough, will not relax, not allowing the tongue to fall.

I-1A-c Air-Electric (Hybrid) Stimulation of Tongue and Toning of the Tongue with MAD Device Here, device uses the both concepts of tongue stimulation which are described above in 1A-a and 1A-b which are air stimulation in combination with electric stimulation of tongue of MAD device.

I-1B.

Figure 54:
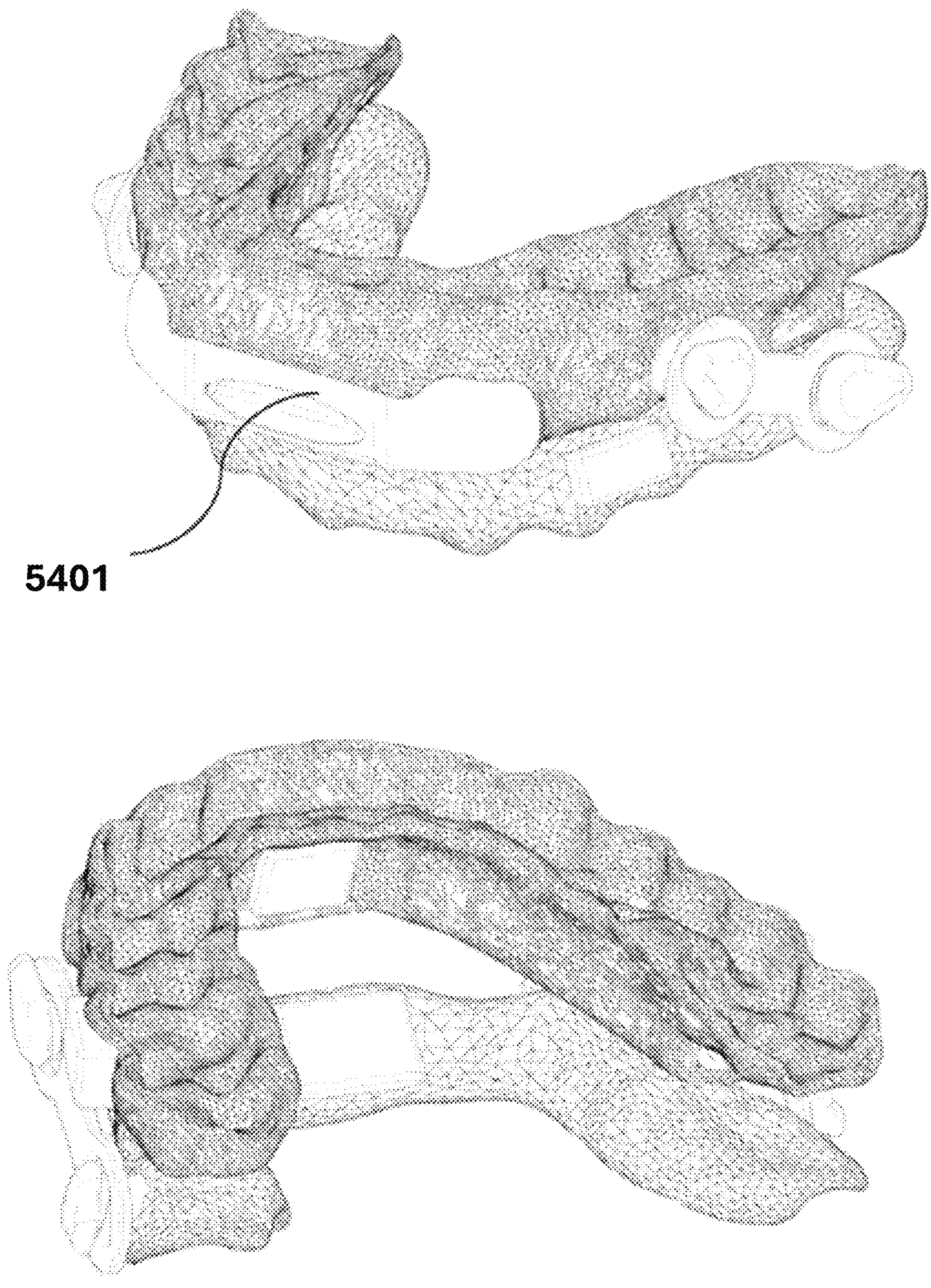
FIG. 54 is a diagram of an example dual-purpose orthodontic appliance showing teeth trays with hollow tubes that can be on the sides or underneath of the teeth trays.

Teeth trays having hollow air passageways ONLY surrounding the teeth trays inside the mouth, No Oval shape hollow tube outside the mouth Here, the concept is same as 1A except there is no oval shape hollow tube sticking out from the mouth as a part of the device. As shown in FIG. 54, the teeth trays have hollow tubes 5401 which can be on the sides or underneath of the teeth trays.

Here sleep apnea is reduced by MAD device approach along with the electric Stimulation of Tongue as explain above in I-1A-b. The benefit of this concept that device stays closed during the sleep. One can use adhesive tape, chin trap or any other commercially available to keep mouth closed during the sleep, allowing nose breathing. At the same time, the device functions as Dual purpose, aligning the teeth or reducing the bruxism and reducing the sleep apnea.

If mouth opens during the sleep, air is directed to the back of the throat due to oval shape opening in the front, by-passing the front of tongue, while stimulating (toning) the tongue and soft tissues at the back, keeping the air passage open in throat are, reducing sleep apnea. This air stimulation is described more detail in I-1A-a. One can use hybrid stimulation as described in I-1A-a and I-1A-b reduce sleep apnea in addition where teeth trays which can function as to align the teeth or reduce the bruxism using bite splint or reduce teeth grinding using nightguard, this way device functions two purposes.

Advantages of the teeth trays with or without air passageway having sensor combinations for Dual Purpose appliance is disclosed herein are many. The appliance with teeth trays in its totality is 100% self-contained and resides completely secure inside the patient’s mouth, enabling complete lip seal. The device is custom manufactured—by combining the patient’s anatomical data input and a health care provider’s (HCP) prescription with a manufacturing library of elements—to seamlessly integrate the sensors and device mechanisms with the patient’s comfort in mind.

In some embodiments, if the teeth trays with or without air passageway comprises more than one sensor, then the Dual-Purpose appliance is designed and manufactured such that the sensors are on one teeth trays, either the upper or the lower teeth tray, or on the outside wall of the hollow tube (air passageway) of the appliance. In other embodiments, the sensors are on different teeth trays or on hollow air passageways. Throughout the present disclosure, the teeth tray with air passageway bearing the sensor(s) called the “technical teeth tray” while the teeth tray without any sensors is called the “free teeth tray.”

In some embodiments, the teeth trays with hollow air passageways are designed such that the most critical components, e.g., the sensors and control modules, are protected.

Figure 55:
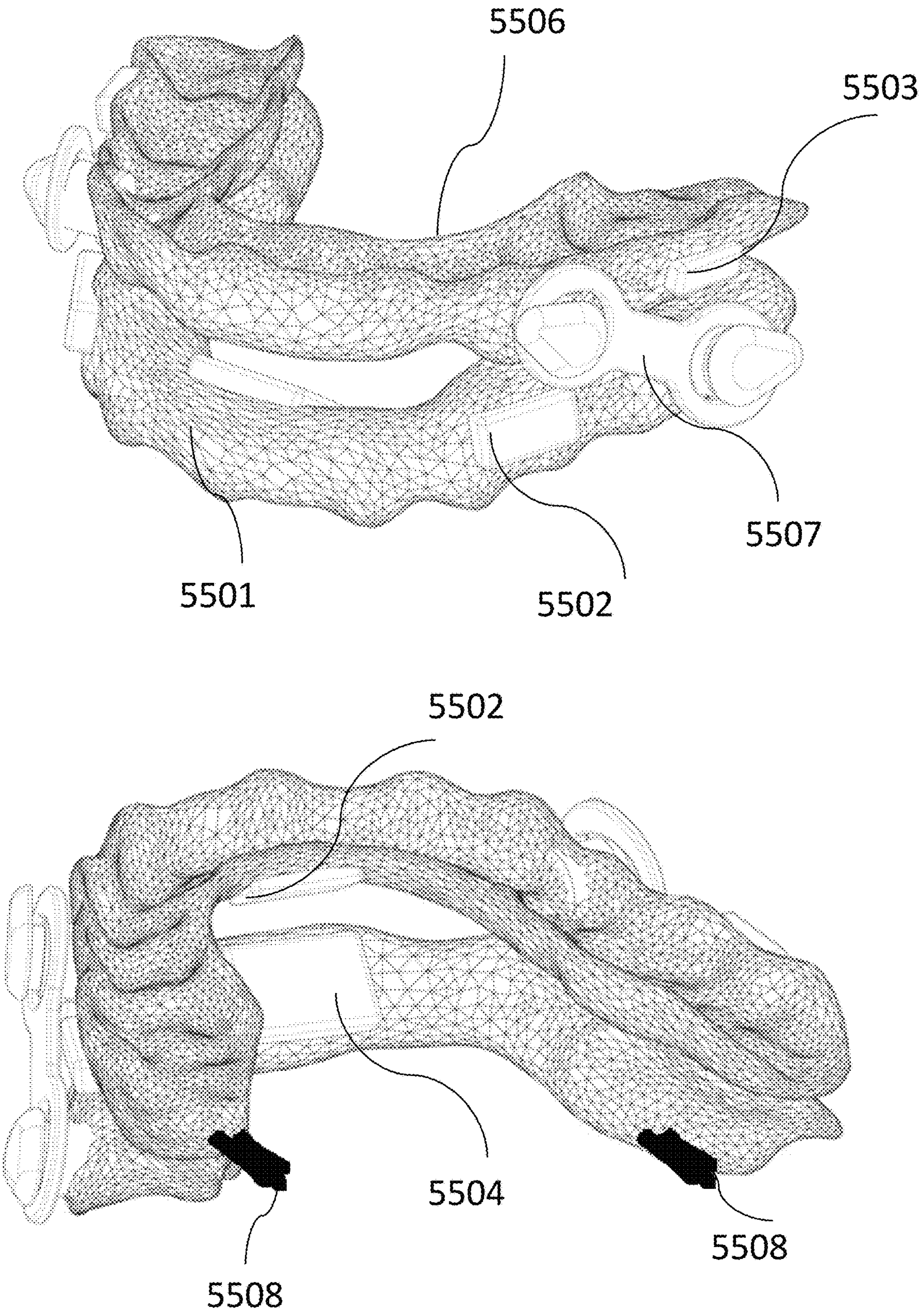
FIG. 55 is a diagram of an example dual-purpose orthodontic appliance showing upper and lower teeth trays connected with linkages on both sides, and control module on teeth the trays.

I-2. “Dual Purpose” MAD Appliance Having Smart Sensors without Hollow Air Passageway on Teeth Trays As shown in FIG. 55, upper 5506 and lower teeth 5501 trays are connected with linkages 5507 on both sides. In one of the embodiments, MAD appliances have sensors and control module on the teeth trays. Here the control module is shown on teeth trays as 5502. As an example, sensor(s) is shown as 5503 but they can be located any other places on the teeth trays. The sensors and control module can be any location except the upper and lower teeth biting area.

Neuro/muscle stimulation of the Tongue or toning of the tongue is done by electric current using electrode or any other means of giving minor electric shock to tongue to keep tongue forward and/or bring it forward if retracted. Here, electrodes are shown as 5508 at the end of lower teeth tray. One or a combination of sensors such as tongue touch sensor, position sensor or pressure sensors are used to find the normal position of tongue (tongue forward). These sensors are located on the upper or lower teeth tray to allow sensing of deviation of the tongue from its normal forward position. 5502 and 5504 are shown as tongue position sensor. The length or numbers of position sensors are such that it should instantly recognize the tongue in forward position and when tongue retracts. This depends on mouth size as each patient's teeth trays have different size. These sensors are located on the upper or lower teeth tray to allow sensing of deviation of the tongue from its normal forward position. This data from the position sensors is fed into a control module with AI capabilities. During the sleep, when tongue retracts, the control module recognizes it and using AI algorithm, provides minor shock, using minor electric current by electrode to the lower part of the tongue's muscles and nerves, causing the tongue to return to its normal forward position, opening up the air passage in the oropharynx area, aiding reduction of episodes of sleep apnea.

The electrodes are bonded to the teeth tray(s) but not affected by the inner fluid of the mouth as electrode are coated with FDA approved adhesive.

In one of the embodiments of MAD or non-MAD device, the leads are attached nonsurgically underneath the tongue, near hypoglossal nerves and electrodes are attached on the teeth tray, preferable lower teeth tray. Here, the electric shock is given to hypoglossal nerve to keep the tongue forward.

For an example, the control module utilizes standard lithium-ion battery or solid-state battery when available and can adjust voltages from 1 to 3.7V and or up to 5V and provide pulsed current of 1 to 4 mA for 1-2 minutes. The amount of volt and amperage depends on number of apnea episodes patients have. In current embodiment, aim is to provide a pulsed current to the inside of the mouth in the proximity of the hypoglossal nerve and/or nerves/muscles of the tongue. The electric shock is applied only when tongue retracts to minimize the voltage and current requirements of the battery.

Electrodes can be sourced from current biomedically approved units currently available in the market. The electrode is attached to end of wire that can be passed through the hollow tube or bonded to the teeth trays which are not in contact of the teeth in close proximity to oropharynx area and in vicinity of the hypoglossal nerves.

One embodiment envisages a machine learning AI system, that can learn episodes of tongue retraction due to signaling from brain to hypoglossal nerve and apply counteracting electric currents once a pattern is established.

In one of the embodiments, by using the safe electric current, which is applied continuously to stimulate and improve muscle function in the mouth and tongue (tone the tongue muscle). In effect, this gives tongue muscles a "work out" exercising them like any other muscle group, making them strong. If patient sleeps with device for few weeks, the tongue muscles will be strengthened and toned, will become strong and sleep apnea level will reduce significantly. Then, the patients may not have to use the appliance for few months till HST (home sleep testing) shows that AHI index (sleep apnea level) has increased. The patient will again sleep with appliance for few weeks followed by no wearing of appliance for few months. Eventually, sleep apnea level can be significantly reduced to a level that patient may not need to use appliance for few months as tongue muscles will be strong enough, not allowing the tongue to fall (tongue and soft tissues are strong enough, they will not relax for few months).

Figure 56:
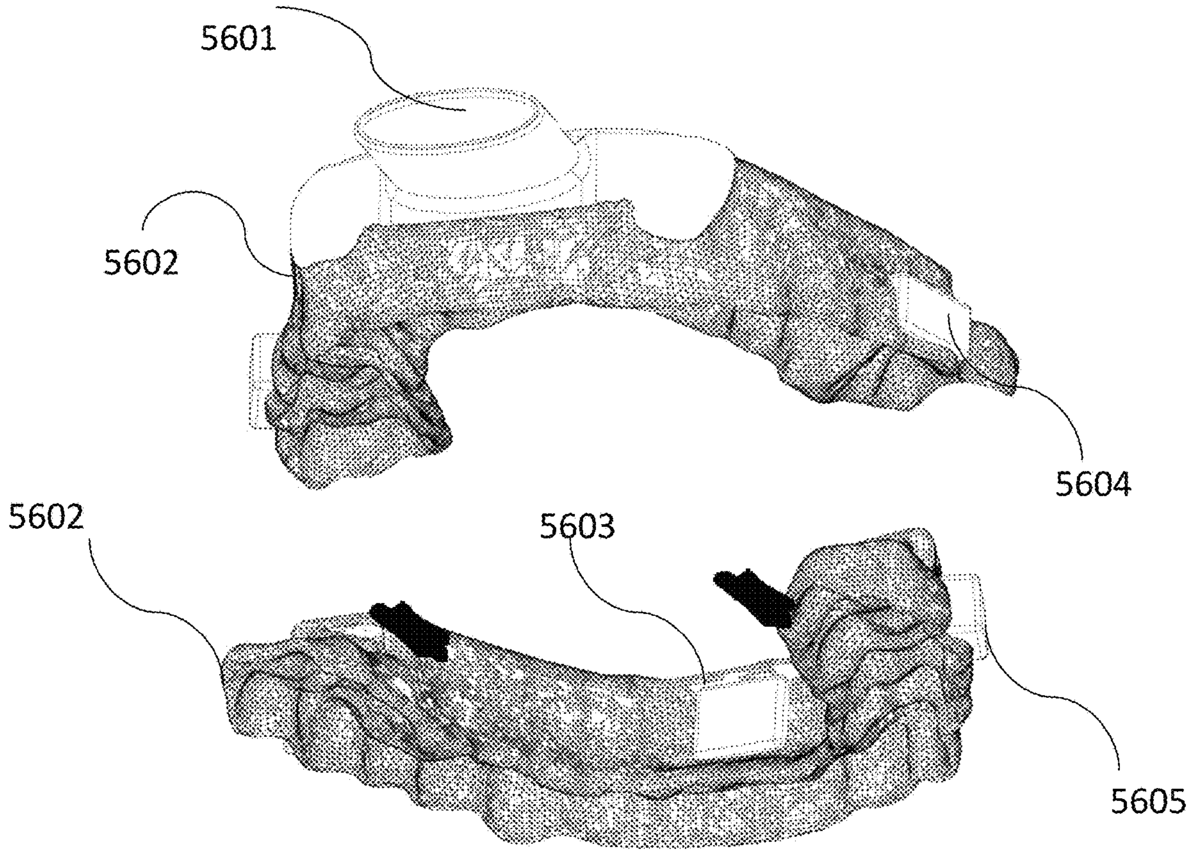
FIG. 56 is a diagram of an example dual-purpose orthodontic appliance showing a lower tray having a hollow passageway.

I-3. "Dual Purpose" NO MAD Appliance with Teeth Trays Having Air Passageway from Outside and on Teeth Trays In one of the embodiments, the dual-purpose appliance has upper tray or lower tray having hollow passageway, preferably lower tray 5602 as shown in FIG. 56. The lower teeth tray 5602 is shown in different orientation, at different angles, to visualize the components. During inhalation, the air enters from oval shape hollow tube 5601 as part of the teeth tray sticking outside the mouth, in lip area. One of the teeth tray's functions is to straighten the teeth as an aligner or reduce bruxism or reduce teeth grinding while other of the teeth tray's function is to reduce the sleep apnea by different mechanism, appliance functioning as "Dual Purpose."

Here, the lower teeth tray function as electric stimulation of tongue nerves and toning of the tongue muscle by different mechanism are as explain in I-1A-b. The 5603 is tongue position sensor(s) and 5604 is control module and 5605 is one of the several sensors.

Figure 57:
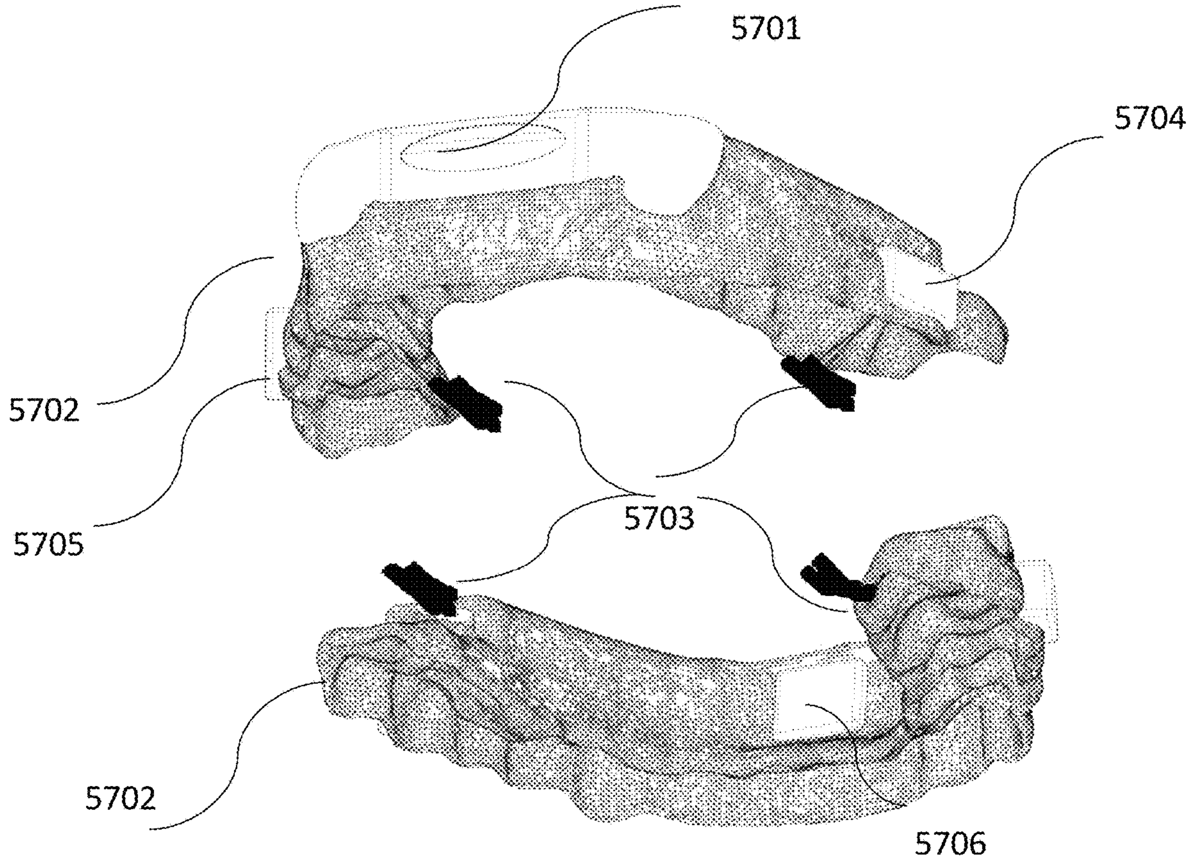
FIG. 57 is a diagram of an example dual-purpose orthodontic appliance with upper tray or lower tray having a hollow passageway, with one of the teeth trays capable of straightening teeth as an aligner or capable of reducing bruxism or teeth grinding, and the teeth trays capable of reducing sleep apnea by a different mechanism.

I-4. "Dual Purpose" No MAD Appliance with Teeth Trays with Air Passageway ONLY on Teeth Trays:

In one of the embodiments, As shown in FIG. 57 the dual-purpose appliance has upper tray or lower tray having hollow passageway, preferably lower tray 5706. 5706 lower teeth tray is shown in two orientations for better visualization of components. One of the teeth tray's functions is to straighten the teeth as an aligner or reduce bruxism or reduce teeth grinding while other function of the teeth trays is to reduce the sleep apnea by different mechanism, appliance functioning as "Dual Purpose".

Here, the lower teeth tray function as electric stimulation of tongue nerves and toning of the tongue muscle by different mechanism are as explain in I-1A-b.

The air enters through 5701 opening if mouth gets open during the sleep and air goes into throat area, by passing the tongue, reducing sleep apnea episodes (air stimulation). Air stimulation of the tongue can be also done by providing micro-holes as described earlier. 5706 is tongue position sensor and 5703 shows the electrode located at the end of the teeth tray, in throat area. 5704 is control module while 5705 is one or several sensors located in this area.

Here the patient sleeps with mouth closed but air stimulation also occurs if mouth opens, reducing the sleep apnea further in addition to electric current stimulation (minor shock) mechanism.

Figure 58:
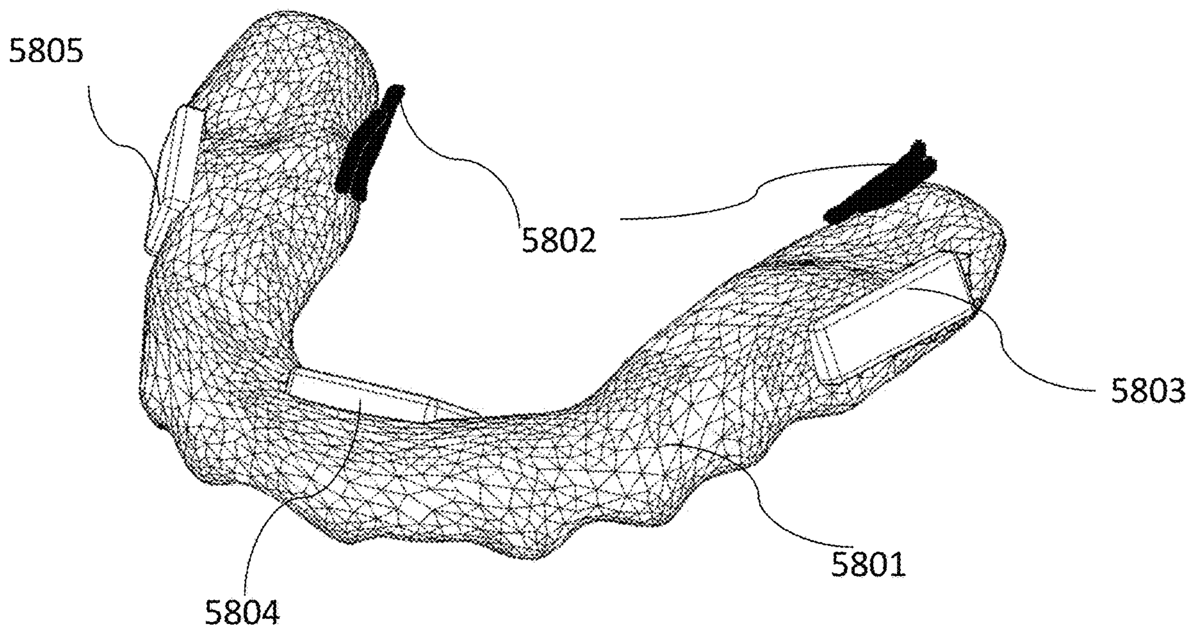
FIG. 58 is a diagram of an example dual-purpose orthodontic appliance having only a lower teeth tray, the lower teeth tray having a hollow passageway and capable of straightening teeth as an aligner or capable of reducing bruxism or teeth grinding, and the teeth tray capable of reducing sleep apnea by a different mechanism.

I-5. "Dual Purpose" Appliance with Teeth Trays without Air Passageway and Having Smart Sensors and No MAD In one of the embodiments, the dual-purpose appliance has ONLY upper tray or lower, preferably lower tray 5801 as shown in FIG. 58. The one of the function of teeth tray is to straighten the teeth as an aligner or reduce bruxism or reduce teeth grinding while other of the teeth tray's function is to reduce the sleep apnea by different mechanism as explained as explained in I-1A.

The electric stimulation of tongue nerves and toning of the tongue muscle are shown by different mechanism in I-1A-b. 5804 is tongue position sensor while 5802 are electrode to provide minor electric shock to the tongue as described in I-1A-b. 5803 is control module while 5805 consists of one or several sensors.

In all above examples, Sleep Position Training is done by using smart sensors such as Gyroscope with or w/o accelerometer and giving minor electric shock to lips or vibration to lips or surrounding area if person sleeps on back, teaching person to sleep on side (feedback mechanism). Here, the dual-purpose appliance can be used without need of micro blower, eliminating a need of external detachable housing box if control module is attached to lip area of the appliance. The smart sensors are attached to outside ovel shape hollow passageway or on the teeth trays or on the hollow air passageways connected to teeth trays and or both.

HST and "Dual Purpose" Device: The dual-purpose appliance with smart sensors can also work as HST device, measuring the parameters such as AHI, Oxygen saturation, snoring (three in one device) and even it can measure brain activity. External detachable housing having sensors along with sensors on teeth trays are useful in some cases. The data from smart sensors and algorithm and use of blue tooth or Wi-Fi technology is used to transfer the data in real time.

II: Dual Purpose Appliances (Devices) with External Detachable Housing

II-1. "Dual Purpose" MAD Appliance Having Smart Sensors and Hollow Passageway on Teeth Trays The detachable oral sleep treatment device includes a front hollow housing defining a first through passage defining an inlet aperture and an output aperture, said front hollow housing having an exterior surface configured to engage the patient's lips the front hollow housing having a first detachable locking interface adjacent the output aperture. The detachable oral sleep treatment device further includes an air flow generating device or air pressure generating device disposed within the first through passage, the generating device configured to create an airflow from the inlet aperture through the output aperture the air flow generating device comprises a controller configured to regulate electrical power supplied to the generating device and a battery disposed within the front hollow housing, said battery being electrically coupled to the airflow generating device and the controller, and a mouthpiece defining first mouthpiece aperture selectively coupled to the front housing, the mouthpiece having first and second curved members together defining a u-shape and having an exterior surface defining a tooth engaging surface, said first and second members defining second and third through passages, said first and second rear mouthpiece apertures disposed adjacent to the retromolar pad members when said mouthpiece is engaged with the patient's teeth.

Figure 59:
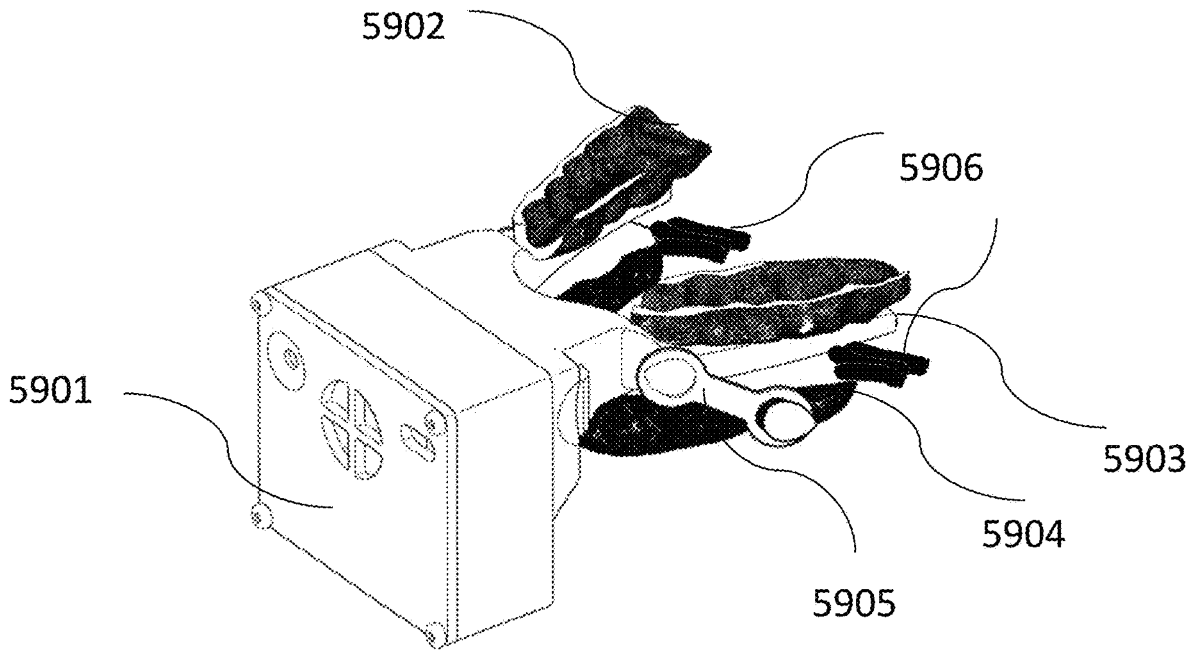
FIG. 59 is a diagram of an example dual-purpose orthodontic appliance showing smart sensors with control modules systems located in the external detachable housing, or on teeth trays, or on hollow tubes (air passageways) connected to teeth trays.

In one of the embodiments, as shown in FIG. 59 the smart sensors with control modules systems are located in the external detachable housing 5901 or on teeth trays or on hollow tubes (air passageways) connected to teeth trays. Here, 5902 is upper teeth tray, while 5904 is lower teeth tray and both trays are connected by linkages 5905. 5903 is hollow air passageway underneath the upper teeth tray, but this hollow air passage can be on the side of the teeth trays, in the center of the teeth trays or any other desired location. The is micro-blower with battery and microprocessor located inside the detachable housing box 5901. Before going the sleep, patient start the blower, the atmospheric air passes through micro-blower and into the hollow air passageway connected to the housing, completely by passing the tongue, does not allow tongue to relax, reducing the episodes of sleep apnea. Based on the functionality of dual-purpose appliance, the smart sensors with the control modules system can be located at all three areas—housing, side of the teeth trays and side of the hollow tubes or mounted only on one of these three places. 5906 are electrode located at the lower teeth tray, near tongue.

The sensors and control modules can be separated from each other wirelessly or with wires.

The first function of the Dual-Purpose appliance of the teeth trays is to align the teeth or reduce the bruxism (use of bite splint, nightguard etc.) as defined in previous CIP patent.

The second function of the teeth trays is to treat the sleep apnea with MAD device concept to reduce the sleep apnea along with other concepts, as shown below One of the embodiments, Air Stimulation of Tongue and toning of the tongue with MAD is achieved as explained in I-1A-a.

One of the embodiments, The Electric Stimulation of Tongue and toning of the tongue with MAD device is explained in I-1A-b.

One of the embodiments, The Air-Electric (Hybrid) Stimulation of Tongue and toning of the tongue with MAD device is explained in I-1A-c.

Only difference here is compared to I-1 is that the appliance has external detachable housing as shown in the figure.

Figure 60:
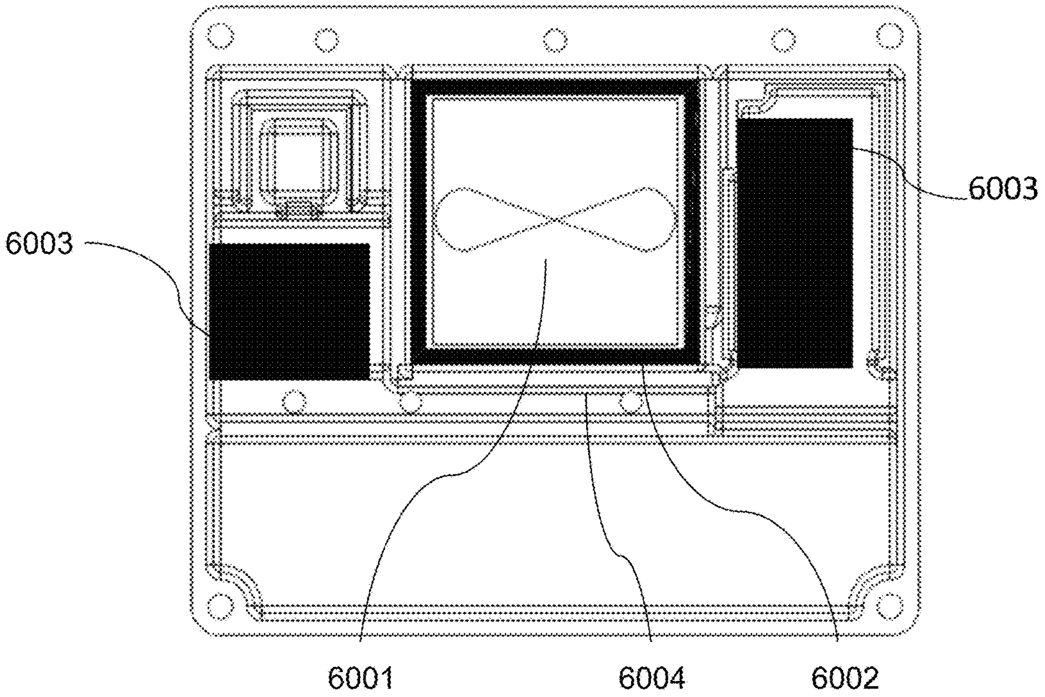
FIG. 60 is a diagram of an example dual-purpose orthodontic appliance showing a vibrational isolating member disposed between an air flow generating or air pressure generating device located in the front hollow housing to reduce vibration transmission into the mouthpiece.
Figure 60:
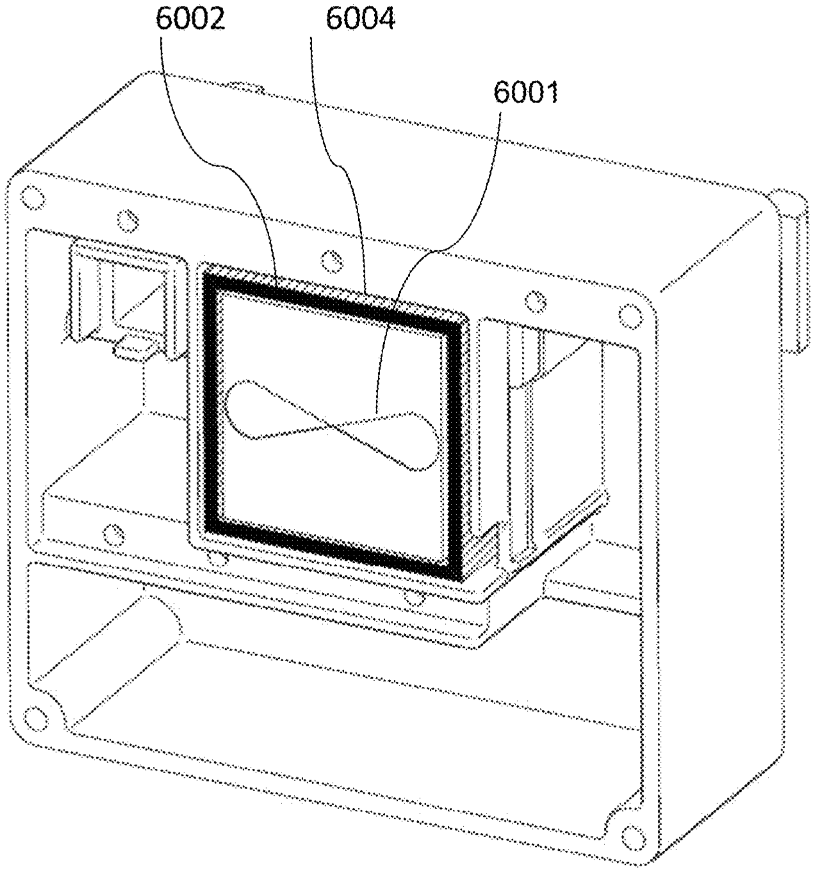

As shown in FIG. 60, the detachable oral sleep treatment device further includes a vibrational isolating member 6002 and 6004 disposed between air flow generating or air pressure generating device 6001 located in the front hollow housing to reduce the vibration transmission into the mouthpiece, wherein the vibrational isolating member reduces the noise transmission to mouthpiece which in turn prevents the bone conduction noise through teeth trays in an inner ear canal. 6003 are sound and vibration deadening materials.

According to the invention above, where the controller is configured to store data related to the plurality of sensors comprising one of a pressure sensor, an airflow sensor and one or more temperature sensors, sound sensor, accelerometer, tilt sensor, and a pulse oximeter.

Figure 61:
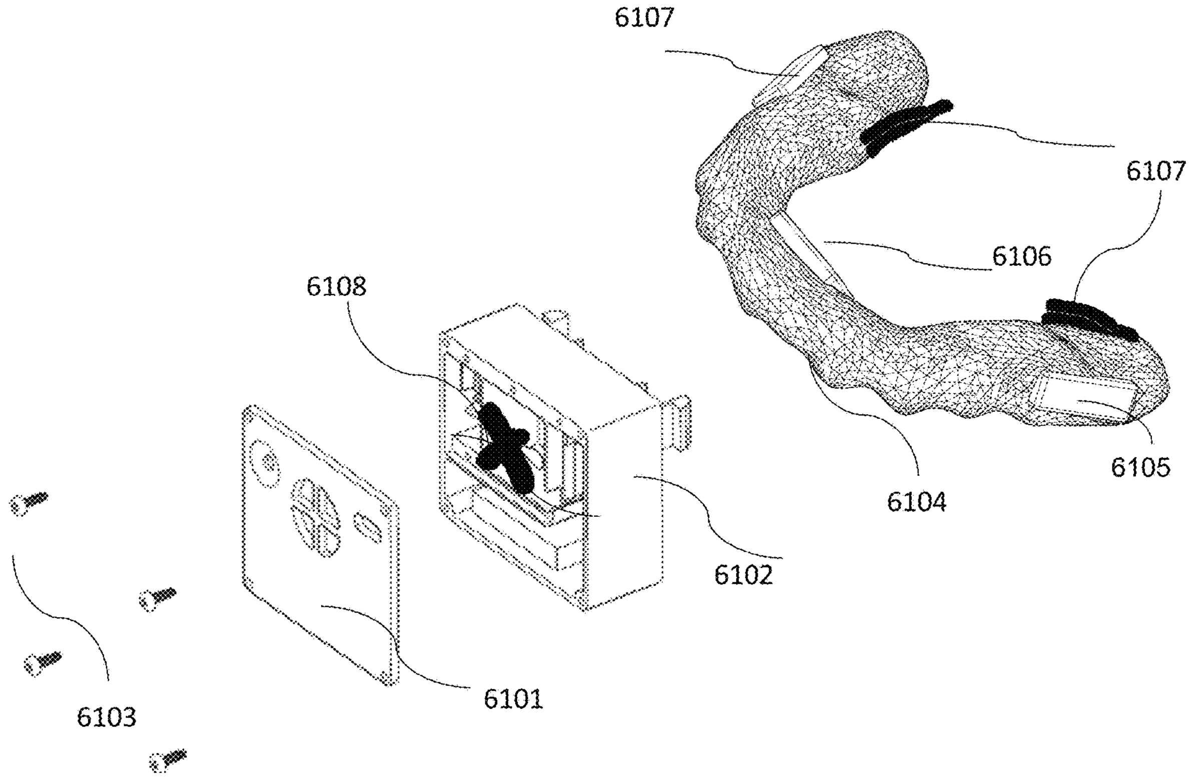
FIG. 61 is a diagram of an example dual-purpose orthodontic appliance with external housing without a micro-blower.

II-2. "Dual Purpose" Appliance with External Housing Having "No Micro-Blower" and Teeth Trays without Air Passageway One of the embodiments, the dual-purpose appliance has external housing 6102 without the micro-blower as shown in FIG. 61. In the exploded view, it shows cross mark on fan 6108, meaning there is no fan in the housing box. The lid is shown as 6101. The purpose of the external housing is to have control module system and very small battery for providing minor electric current to the tongue, stimulating the to the lower part of the tongue's muscles and nerves, causing the tongue to return to its normal forward position, opening up the air passage in the oropharynx area, aiding reduction of episodes of sleep apnea. The 6104 is lower teeth tray. The 6106 is tongue position sensor. The 6107 is control module while 6105 is one or combination of several sensors. 6107 is set of electrodes at the end of lower teeth tray, in the vicinity of tongue.

Figure 62:
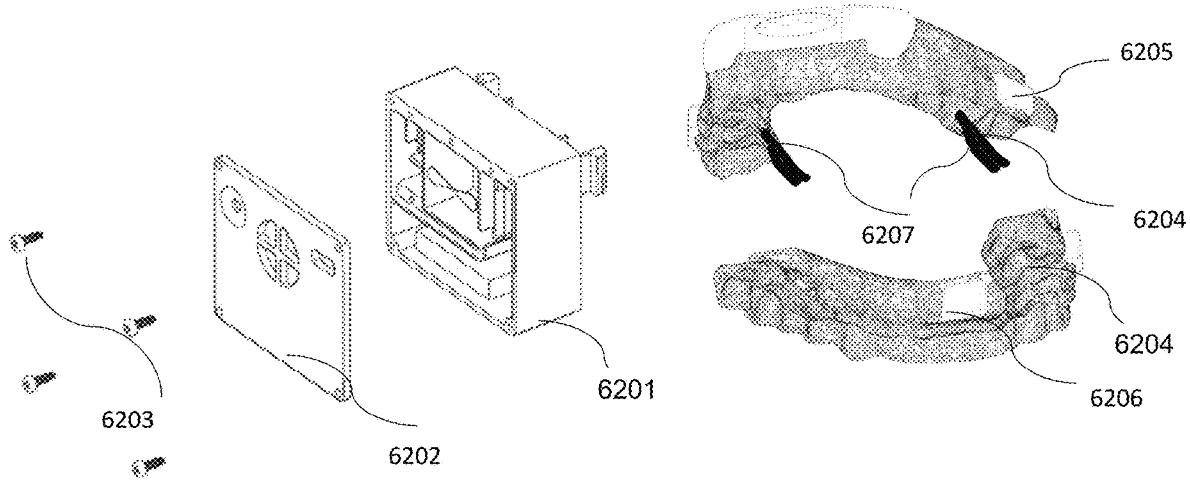
FIG. 62 is a diagram of an example dual-purpose orthodontic appliance showing external detachable housing with lid and lower teeth tray shown in two different orientations, with tongue position sensor.
Figure 63:
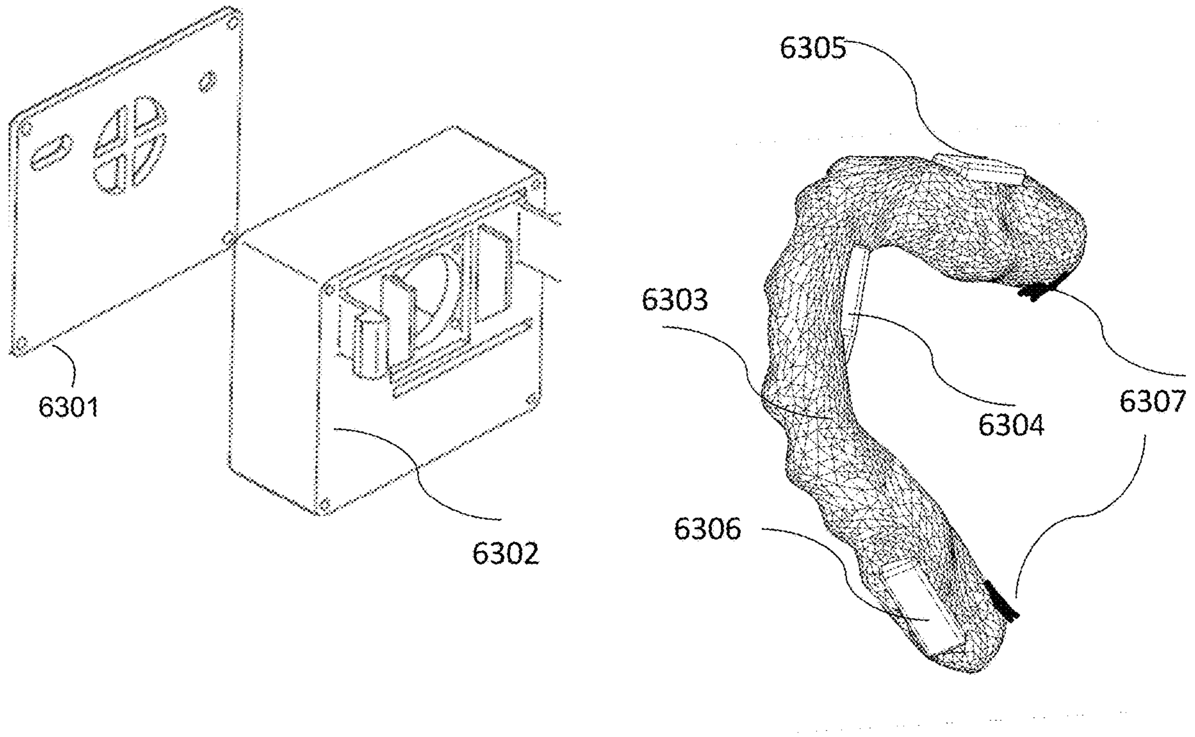
FIG. 63 is a diagram of another view of an example dual-purpose orthodontic appliance with control module and sensors.

II-3. "Dual Purpose" NO-MAD Appliance Having Smart Sensors and Hollow Passageway on Teeth Trays In one of the embodiments, the smart sensors with control modules systems are located in the external detachable housing or on teeth trays or on hollow tubes (air passageways) connected to teeth trays. Here, FIG. 62, 6201 is external detachable housing with lid 6202 while 6204 is lower teeth tray shown in two different orientations. 6202 is tongue position sensor. Based on the functionality of dual-purpose appliance, the smart sensors with the control modules system can be located at all three areas—housing 6201, side of the teeth trays, preferably lower teeth trays 6204 and side of the hollow tubes or mounted only on one of these three places. 6205 is control module and 6207 is a sensor or combination of sensors. 6208 are the electrodes attached to the end of the lower teeth tray, at the end of tongue area in throat.

According to the invention above, where the controller is configured to store data related to the plurality of sensors comprising one of a pressure sensor, an airflow sensor and one or more temperature sensors, sound sensor, accelerometer, tilt sensor, and a pulse oximeter. Other sensors are described in "Sensors" sections and their functions.

In one of the embodiments, there is NO-MAD, meaning only upper teeth tray or preferably lower teeth tray is connected to the external detachable housing.

The sensors and control modules can be separated from each other wirelessly or with wires.

In one of the embodiments, the dual-purpose appliance has upper tray or lower tray having hollow passageway, preferably lower tray. One of the teeth tray's functions is to straighten the teeth as an aligner or reduce bruxism or reduce teeth grinding while other function of teeth trays is to reduce the sleep apnea by different mechanism, appliance functioning as "Dual Purpose". The 6206 is tongue position sensor. 6205 is control module on the tray. 6204 is a sensor or combination of sensors depending on the final function of the device.

One of the embodiments, Air Stimulation of Tongue and toning of the tongue with MAD is achieved as explained in I-1A-a.

One of the embodiments, The Electric Stimulation of Tongue and toning of the tongue with MAD device is explained in I-1A-b.

One of the embodiments, The Air-Electric (Hybrid) Stimulation of Tongue and toning of the tongue with MAD device is explained in I-1A-c.

Sensors and their Functions

A variety of sensors are contemplated to be used with the disclosed. The sensors can be mounted in the external detachable housing and or on the teeth trays and or on the hollow air passageways, depending on the dual-purpose appliance as described in I and II are used.

In general, the sensors can be divided into the following categories: physiological sensors, physical sensors, chemical sensors, and positional sensors.

In some embodiments, physiological sensors measure and relay such physiological data as body temperature, respiration rate, heart rate, or other relevant physiological data, and/or any variability in the above values.

In some embodiments, physical sensors are those that detect the mode of breathing, e.g., vibration in the breathing, airflow rate, oxygen concentration of inhaled air, etc., and correlate that to airflow restriction.

In some embodiments, the sensor is selected from an oxygen sensor measuring the oxygen concentration of the inhaled air, a carbon dioxide sensor measuring the carbon dioxide concentration of the exhaled air, a pressure sensor measuring the atmospheric pressure or the air pressure inside the oral cavity, an airflow sensor, a noise detector, or an actigraphy sensor.

The sensors can also detect snoring, and/or perform airway flow signature analysis.

This combination of sensors and using algorithm/software provides the information on episodes of sleep apnea and tell the microprocess to take corrective actions to keep tongue to its normal forward position, opening up the air passage in the oropharynx area, aiding reduction of episodes of sleep apnea.

In some embodiments, the sensor measures the pressure exerted on the teeth trays by the patient's teeth in order to measure the extent of clenching and/or grinding of dentition surfaces.

In some embodiments, the smart sensors such as Gyroscope with or w/o accelerometer are used for Sleep Position Training. It is done by using and giving minor electric shock to lips or tongue or vibration to lips or tongue and or surrounding area if person sleeps on back, teaching person to sleep on side (feedback mechanism).

In some embodiments, when sensors are mounted on the teeth trays, chemical sensors are used to measure the body's physiological response to breathing. For example, the saliva pH, saliva sugar concentration, saliva conductivity, levels of stress markers, such as salivary cortisol, blood oxygen saturation level, blood pH, blood glucose levels, blood insulin levels, inflammatory markers, and the like, can be measured in real time and reported to the HCP via the base. Bacterial biosensors can provide information to the HCP on the level of bacterial activity in the mouth during sleep.

In some embodiments, the sensor is a component of a control module system, which includes other components besides the sensor.

In certain embodiments, the a control module system components include sensor sensing mechanism, one or more of a battery (rechargeable or replaceable), a battery recharging circuit compatible with industry standards, if applicable, on-board memory, communication module, analog/digital converter to convert sensor voltage inputs to digital signal etc.

In some embodiments, computer aided design (CAD) program are used where to put sensors and control module system during the design of the teeth trays with or without external detachable housing.

Communication

The presently disclosed sensors are in wireless communication with a base, transmitting the data they obtained. Various modes of wireless communication are well-known in the art. Currently, the most popular mode appears to be Bluetooth® communication. Other modes such as radio, infrared, magnetic, or the like can also be used. All modes of wireless communication now known or developed in the future are contemplated for use with the presently disclosed sensors.

In some embodiments, the base is a software contained in a physical cradle. The cradle is configured for wireless communication with the sensor embedded in the teeth tray with or without air passageways. In some embodiments, following the use, the patient places the teeth trays with or without air passageways in the cradle, which can optionally recharge the batteries of the sensor.

The battery can also be recharged directly using USB port.

In some embodiments, the cradle is configured to clean the teeth trays with or without air passageways, for example, by providing a bath into which the teeth trays can be placed, or by having a well-contained chamber for the teeth trays to be cleaned using cleansers or steam or the like. In other embodiments, the base is a software (including an app) on a smart phone (e.g., iPhone®, Galaxy®), smart tablet (e.g., iPad®, Surface®), or a laptop or desktop computer (collectively "a device").

In some embodiments, the base will sound an alarm audible enough to wake the patient up, if the physiological data, such as the blood oxygen level or air flow disturbance, indicate an unhealthy state for the patient to continue to be sleeping.

In other embodiments, the base relays a command to the teeth trays with or without air passage to release a repugnant chemical substance in the mouth, such as one with a bitter taste, to wake the patient up.

In some embodiments, the base is programmed to alert the emergency medical services if the physiological data is worsening and the patient shows no sign of waking up, for example, by turning the alarm off.

In some embodiments, the presently disclosed combination of teeth trays with or without air passageway and sensors is used to deliver medications to the patient in a controlled fashion.

In some of these embodiments, the teeth trays with or without air passageway comprises built-in refillable cavities that can be filled with a prescribed medication.

In other embodiments, the teeth trays with or without air passageway comprises a location for a prefilled container of medication to be placed. In any case, the design of the teeth trays with or without air passageway with the medication-dispensing components is such that the patient does not feel the bulk of the medication-dispensing components and the appliance is as comfortable to wear as if it did not have the medication-dispensing components.

In response to a time cue or input from an embedded sensor, the base relays a command to the teeth trays with or without air passage way and the medication-dispensing components to release a preset amount of the medication either between the cheek and the gum for a buccal administration or into the patient's mouth for the medication to be inhaled. Examples include stress reducing agents, calming agents, glucose, insulin, nitroglycerin or other heart medications for atrial fibrillation or unstable angina, and the like.

In some embodiments, the base is also in wireless communication with a software on a device operated by a health care provider (HCP). In these embodiments, the base communicates the collected data directly to the HCP device, where the HCP can monitor the progress of the patient without the need for the patient to make office visits. This feature is quite useful for individuals who travel constantly, such as salespersons, long distance drivers, airline pilots, and the like. By taking advantage of this feature, the HCP can continually monitor the patient and intervene with a recommendation if that is in the best interest of the patient. This way, problems are detected and corrected as they happen.

In some embodiments, the base communicates with the HCP software through the internet, phone lines, satellite, radio, microwave, or other forms of long distance communication now known or later developed.

In some embodiments, multiple sensors are connected to the same control module system, whereas in other embodiments, each sensor has its own control module system.

In the foregoing description, the invention has been described with reference to specific exemplary embodiments thereof. It will be apparent to those skilled in the art that a person understanding this invention may conceive of changes or other embodiments or variations, which utilize the principles of this invention without departing from the broader spirit and scope of the invention. The specification and drawings are, therefore, to be regarded in an illustrative rather than a restrictive sense.

The invention claimed is:

1. A dual-purpose orthodontic appliance engageable with a patient's teeth; comprising:

a bite retainer having a tooth tray;

a control module configured with wireless communication protocols, the control module mounted on the tooth tray of the dual-purpose orthodontic appliance;

at least one sensor mounted on the tooth tray, the at least one sensor in wired or wireless communication with the control module;

an electrode mounted on the teeth tray and positioned to electrically stimulate with a pulsed current only a tongue or only in proximity of a hypoglossal nerve when the dual-purpose orthodontic appliance engages with a patient's teeth;

the dual-purpose orthodontic appliance, including the control module and the at least one sensor, to move teeth of the patient into a straightened alignment while treating one of a sleep apnea condition or a snoring condition and without mandibular advancement.

2. The dual-purpose orthodontic appliance of claim 1, wherein the at least one sensor measures a body temperature, a respiration rate, a heart rate, a vibration in a respiration of the patient, an airflow rate, an oxygen concentration, a carbon dioxide concentration, an atmospheric pressure, an intraoral air pressure, or a noise.

3. The dual-purpose orthodontic appliance device of claim 1, further comprising micro-holes in air passageways to stimulate a tongue of the patient with an airflow for reducing the sleep apnea condition or the snoring condition.

4. The dual-purpose orthodontic appliance device of claim 1, further comprising a machine learning module mounted on the tooth tray to learn a pattern of tongue retraction and apply an electric current to counteract the tongue retraction based on the pattern.

5. The dual-purpose orthodontic appliance of claim 1, wherein the control module applies an electrical stimulation to the tongue of the patient via the electrode.

6. The dual-purpose orthodontic appliance of claim 5, wherein the control module applies both the electrical stimulation and an airflow to the tongue of the patient.

7. The dual-purpose orthodontic appliance of claim 5, wherein the electrical stimulation is applied via leads under the tongue of the patient near a hypoglossal nerve of the patient and/or via an electric shock to a lip of the patient.

8. The dual-purpose orthodontic appliance of claim 1, further comprising an air passageway adapted to extend outside a mouth of the patient, the control module and the at least one sensor, the air passageway connecting to the tooth tray.

* * * * *